United States Patent
Rajamani et al.

(10) Patent No.: US 11,396,531 B2
(45) Date of Patent: Jul. 26, 2022

(54) ANTIMICROBIAL PEPTIDES COMPRISING EPSILON LYSINE RESIDUES

(71) Applicants: SINGAPORE HEALTH SERVICES PTE LTD, Singapore (SG); NANYANG TECHNOLOGICAL UNIVERSITY, Singapore (SG)

(72) Inventors: Lakshminarayanan Rajamani, Singapore (SG); Venkatesh Mayandi, Singapore (SG); Tze Leng Eunice Goh, Singapore (SG); Roger Wilmer Beuerman, Singapore (SG); Navin Kumar Verma, Singapore (SG)

(73) Assignees: Singapore Health Services Pte Ltd, Singapore (SG); Nanyang Technological University, Singapore (SG)

( * ) Notice: Subject to any disclaimer, the term of this patent is extended or adjusted under 35 U.S.C. 154(b) by 0 days.

(21) Appl. No.: 16/346,808

(22) PCT Filed: Oct. 31, 2017

(86) PCT No.: PCT/SG2017/050548
§ 371 (c)(1),
(2) Date: May 1, 2019

(87) PCT Pub. No.: WO2018/084807
PCT Pub. Date: May 11, 2018

(65) Prior Publication Data
US 2019/0276505 A1 Sep. 12, 2019

(30) Foreign Application Priority Data
Nov. 1, 2016 (SG) .............. 10201609136R

(51) Int. Cl.
| | | |
|---|---|---|
| *C07K 14/00* | (2006.01) | |
| *C07K 14/02* | (2006.01) | |
| *A61K 38/08* | (2019.01) | |
| *A61P 31/04* | (2006.01) | |
| *C07K 14/435* | (2006.01) | |
| *C07K 7/08* | (2006.01) | |
| *A61K 38/00* | (2006.01) | |

(52) U.S. Cl.
CPC ........ *C07K 14/43568* (2013.01); *A61P 31/04* (2018.01); *C07K 7/08* (2013.01); *C07K 14/43572* (2013.01); *A61K 38/00* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 2002/0045736 A1 | 4/2002 | Yu et al. | |
| 2003/0144230 A1* | 7/2003 | Hawley-Nelson | .......................... A61K 47/6911 514/44 R |
| 2003/0166548 A1* | 9/2003 | Peterson | .......... C07K 14/43572 435/7.1 |
| 2010/0316643 A1 | 12/2010 | Eckert et al. | |

FOREIGN PATENT DOCUMENTS

| | | |
|---|---|---|
| JP | 2006055157 A | 3/2006 |
| WO | 2007/023509 | 3/2007 |
| WO | 2010/091294 | 8/2010 |

OTHER PUBLICATIONS

Yang et al., "Enhancing antimicrobial activity of mastoparan-B by amino acid substitutions," Journal of Asia-Pacific entomology 16: 349-355 (2013) (Year: 2013).*
Achouri et al., "recent advances in ocular drug delivery," drug development and industrial pharmacy 39: 1599-1617 (2012) (Year: 2012).*
McDonnell et al. "Antiseptics and Disinfectants: Activity, Action, and Resistance" Clinical Microbiology Reviews12(1):147-179 (1999).
Percival et al. "Antiseptics for treating infected wounds: Efficacy on biofilms and effect of pH", Critical Reviews in Microbiology 42(2):293-309 (2016).
Fry "Topical Antimicrobials and the Open Surgical Wound", Surgical Infections 17(5):520-524 (2016).
Lachapelle et al. "Antiseptics in the era of bacterial resistance: a focus on povidone iodine", Clin. Pract. 10(5):579-592 (2013).

(Continued)

*Primary Examiner* — Julie Ha
*Assistant Examiner* — Kristina M Hellman
(74) *Attorney, Agent, or Firm* — Myers Bigel, P.A.

(57) ABSTRACT

The present disclosure relates to a peptide comprising at least five amino acid residues, wherein at least one amino acid residue is modified to an epsilon-lysine, delta-ornithine, gamma-2,4-diaminobutyric acid, beta-2,3-diaminopropionic acid, with the peptide also comprising at least one non-epsilon lysine, non-delta-ornithine, non-gamma-2,4-diaminobutyric acid or non-beta-2,3-diaminopropionic acid, and wherein the peptide displays a reduced or no cytotoxicity when compared to an equivalent non-modified peptide. In a preferred embodiment, the modifications are to the melittin or mastoparan B peptides, and comprise the substitution of at least one a-lysine residue for an ε-lysine residue, and the modified peptides display antimicrobial activity. The present disclosure is also directed to pharmaceutical compositions, kits, ophthalmic preparations comprising the modified antimicrobial peptides and use of the modified antimicrobial peptides in methods of inhibiting growth of microorganisms, methods of managing microbial colonization, methods of treating proliferative disease, and methods of treating inflammation. The present disclosure also relates to a method of improving the therapeutic index (safety) of an isolated peptide comprising the aforementioned modification.

12 Claims, 29 Drawing Sheets

Specification includes a Sequence Listing.

(56) References Cited

OTHER PUBLICATIONS

Wilson et al. "A Toxicity Index of Skin and Wound Cleansers Used on In Vitro Fibroblasts and Keratinocytes", Advances in Skin & Wound Care 18(7):373-378 (2005).
Drosou et al. "Antiseptics on Wounds: An Area of Controversy (Part One)", Wounds Research 15(6):1-12 (2003).
Thomas et al. "Mechanisms of Delayed Wound Healing by Commonly Used Antiseptics", J. Trauma. 66:82-91 (2009).
Safety and Effectiveness of Consumer Antiseptics; Topical Antimicrobial Drug Products for Over-the-Counter Human Use, Federal Register 81(172):61106-61130 (2016).
Müller et al. "Biocompatibility index of antiseptic agents by parallel assessment of antimicrobial activity and cellular cytotoxicity", J. Antimicrobial Chemotherapy 61:1281-1287 (2008).
Gilbert et al. "Cationic antiseptics: diversity of action under a common epithet", J. Applied Microbiology 99:703-715 (2005).
Hübner et al. "Octenidine Dihydrochloride, a Modern Antiseptic for Skin, Mucous Membranes and Wounds", Skin Pharmacol Physiol 23:244-258 (2010).
Lachapelle "A comparison of the irritant and allergenic properties of antiseptics", Eur J. Dermatol 24(1):3-9 (2014).
Kramer et al. "Efficacy and Tolerance of Selected Antiseptic Substances in Respect of Suitability for Use on the Eye", Antiseptic Prophylaxis and Therapy in Ocular Infections. Dev Ophthalmol. 33:117-144 (2002).
Qu et al. "Searching for new strategies against-polymicrobial biofilm infections: guanylated polymethacrylates kill mixed fungal/bacterial biofilms", J. Antimicrob Chemother 71:413-421 (2016).
Beyth et al. "Antibacterial activity of bone cement containing quaternary ammonium polyethyleneimine nanoparticles", J. Antimicrob Chemother pp. 854-855 (2014).
Siedenbiedel et al. "Antimicrobial Polymers in Solution and on Surfaces: Overview and Functional Principles", Polymers 4:46-71 (2012).
Zhou et al. "A photopolymerized antimicrobial hydrogel coating derived from epsilon-poly-L-lysine", Biomaterials 32:2704-2712 (2011).
Santos et al. "Recent Developments in Antimicrobial Polymers:A Review", Materials 9(599): 1-33 (2016).
Huang et al. "Recent Advances in Antimicroblal Polymers: A Mini-Review", Int. J. Mol. Sci. 17(1578):1-14 (2016).
Li et al. "Safe and efficient, membrane permeabilizing polymers based on PLLA for antibacterial applications", RSC Adv. 6:28947-28955 (2016).
Lam et al. "Combating multidrug-resistant Gram-negative bacteria with structurally nanoengineered antimicrobial peptide polymers", Nature Microbiology 1:1-11 (2016).
Fox et al. "Insight into membrane selectivity of linear and branched polyethylenimines and their potential as biocides for advanced wound dressings", Acta Biomaterialia 37:155-164 (2016).
Lohner "Membrane-active Antimicrobial Peptides as Template Structures for Novel Antibiotic Agents", Current Topics in Medicinal Chemistry 17:508-519 (2017).
Sudheendra et al. "Membrane disruptive antimicrobial activities of human beta-defensin-3 analogs", Eur. J. Medicinal Chemistry 91:91-99 (2015).
Aung et al. "Biofilms of Pathogenic Nontuberculous Mycobacteria Targeted by New Therapeutic Approaches", Antimicrobial Agents and Chemotherapy 60(1):24-35 (2016).
Ventola "The Antibiotic Resistance Crisis, Part 1: Causes and Threats", P&T 40(4):277-283 (2015).
Ventola "The Antibiotic Resistance Crisis, Part 2: Management Strategies and New Agents", P&T 40(5):344-352 (2015).
Lakshminarayanan et al. "Synthetic Multivalent Antifungal Peptides Effective against Fungi", PLoS One 9(2):e87730 (2014) (18 pages).
Bruinsma et al. "Resistance to a polyquaternium-1 lens care solution and isoelectric points of Pseudomonas aeruginosa strains", J. Antimicrob Chemother 57:764-766 (2006).
Soon et al. "Different surface charge of colistin-susceptible and -resistant Acinetobacter baumannii cells measured with zeta potential as a function of growth phase and colistin treatment", J Antimicrob Chemother 66:126-133 (2011).
Michalová et al., "Povidone-Iodine (Betadine) in the Treatment of Experimental Psuedomonas aeruginosa Keratitis", Cornea 15(5):533-536 (1996).
Melki et al. "Effect of topical povidone-iodine versus topical ofloxacin on experimental *Staphylococcus keratitis*", Graefe's Arch Clin Exp Ophthalmol 238:459-462 (2000).
Bu et al. "A Comparison of Topical Chlorhexidine, Ciprofloxacin, and Fortified Tobramycin/Cefazolin in Rabbit Models of *Staphylococcus* and Pseudomonas keratitis", J. Ocular Pharmacology and Therapeutics 23(3):213-220 (2007).
Hamill et al. "Experimental Evaluation of Chlorhexidine Gluconate for Ocular Antisepsis", Antimicrobial Agents and Chemother 26(6):793-796 (1984).
Green et al. "Chlorhexidine Effects on Corneal Epithelium and Endothelium", Arch Ophthalmol 98:1273-1278 (1980).
Berditsch et al. "Synergistic Effect of Membrane-Active Peptides Polymyxin B and Gramicidin S on Multidrug-Resistant Strains and Biofilms of Pseudomonas aeruginosa", Antimicrobial Agents and Chemotherapy 59(9):5288-5296 (2015).
Gasparri et al. "Quantification of the Proliferation Index of Human Dermal Fibroblast Cultures with the ArrayScan™ High-Content Screening Reader", Journal of Biomolecular Screening pp. 232-243 (2004).
Mohamed et al. "Activation of stress-related signalling pathway in human cells upon SiO2 nanoparticles exposure as an early indicator of cytotoxicity", Journal of Nanobiotechnology 9(29):1-14 (2011).
Riau et al. "Collagen-Based Artificial Corneal Scaffold with Anti-Infective Capability for Prevention of Perioperative Bacterial Infections", ACS Biomater. Sci. Eng. 1:1324-1334 (2015).
Konstantopoulos et al. "Prophylactic Vancomycin Drops Reduce the Severity of Early Bacterial Keratitis in Keratoprosthesis", PLoS One (2015) (13 pages).
Konstantopoulos et al. "In Vivo Quantification of Bacterial Keratitis with Optical Coherence Tomography", Investigative Ophthalmology & Visual Science 52(2):1093-1097 (2011).
Cockerill et al. "Methods for Dilution Antimicrobial Susceptibility Tests for Bacteria That Grow Aerobically; Approved Standard—Ninth Edition", 32(2) (2012) (88 pages).
Venkatesh et al. "Antimicrobial Activity and Cell Selectivity of Synthetic and Biosynthetic Cationic Polymers", Antimicrobial Agents and Chemotherapy 61(10):e00469-17 (2017) (15 pages).
Wade st al. "All-D amino acid-containing channel-forming antibiotic peptides", Proc. Natl. Acad. Sci. USA 87:4761-4765 (1990).
Oren et al. "Selective Lysis of Bacteria but Not Mammalian Cells by Diastereomers of Melittin:Structure-Function Study", Biochemistry 36:1823-1835 (1997).
Zhu et al. "Substitution of the leucine zipper sequence in melittin with peptoid residues affects self-association, cell selectivity, and mode of action", Biochimica et Biophysica Acta 1768:1506-1517 (2007).
Unger et al. "The Effect of Cyclization of Magainin 2 and Melittin Analogues on Structure, Function, and Model Membrane Interactions: Implication to Their Mode of Action", Biochemistry 40:6388-6397 (2001).
Jamasbi et al. "Melittin peptides exhibit different activity on different cells and model membranes", Amino Acids 43:2759-2766 (2014).
Tam et al. "Antimicrobial dendrimeric peptides", Eur. J. Biochem. 269:923-932 (2002).
Hyldgaard et al. "The Antimicrobial Mechanism of Action of Epsilon-Poly-L-Lysine", Applied and Environmental Microbiology 80(24):7758-7770 (2014).
Shima et al. "Antimicrobial Action of episilon-Poly-L-Lysine", The Journal of Antibiotics 37(11):1449-1455 (1984).
Fernández-Reyes et al. "Lysine N episilon-Trimethylation, a tool for Improving the Selectivity of Antimicrobial Peptides", J. Med. Chem. 53:5587-5596 (2010).

(56) References Cited

OTHER PUBLICATIONS

Yang et al. "Long Hydrophilic-Cationic Polymers: A Different Pathway toward Preferential Activity against Bacterial over Mammalian Membranes", Biamacromolecules 15:3267-3277 (2014).

Kini et al. "A common cytolytic region in myotoxins, hemolysins, cardiotoxins and antibacterial peptides", Int. J. Peptide Protein Res. 34:277-286 (1989).

"Extended European Search Report corresponding to European Application No. 17868131.8 dated Apr. 9, 2020".

"Office Action corresponding to Japanese Application No. 2019-523802 dated Jul. 6, 2021".

"Written Opinion corresponding to Singapore Application No. 11201903961R dated Jul. 29, 2020".

De Souza, Bibiana Monson, et al., "Structure-activity relationship of mastoparan analogs: Effects of the number and positioning of Lys residues on secondary structure, interaction with membrane-mimetic systems and biological activity", Peptides 75:164-174 (Oct. 1, 2015).

Mayandi, Venkatesh, et al., "Rational Substitution of [epsilon]-Lysine for [alpha]-Lysine Enhances the Cell and Membrane Selectivity of Pore-Forming Melittin", Journal of Medicinal Chemistry 63(7):3522-3537 (Mar. 16, 2020).

Ruggeri, Zaverio M, et al., "Inhibition of platelet function with synthetic peptides designed to be high-affinity antagonists of fibrinogen binding to platelets", Proc. Natl. Acad. Sci. USA 83:5708-5712 (Aug. 1986).

Werkmeister, Jerome A, et al., "The effect of sequence variations and structure on the cytolytic activity of melittin peptides", Biochimica et Biophysica Acta (BBA)—General Subjects 1157(1):50-54 (May 7, 1993).

\* cited by examiner

| Structure | Sequence |
|---|---|
| 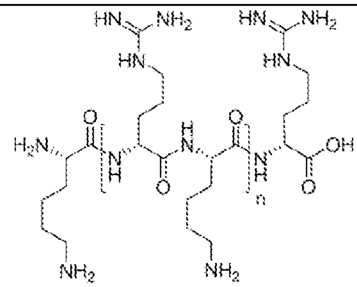 | KRKRKRKRKRKR (HC 1; SEQ ID NO: 3), where K and R are natural α-L-lysyl and α-L-arginine residues |
| 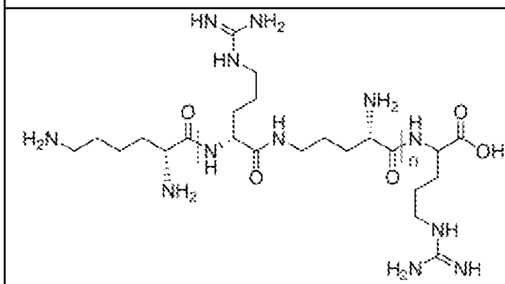 | _K_R_K_R_K_R_K_R_K_R_K_R (HC 2; SEQ ID NO: 17), where _K_ is ε-L-lysyl residue |
| 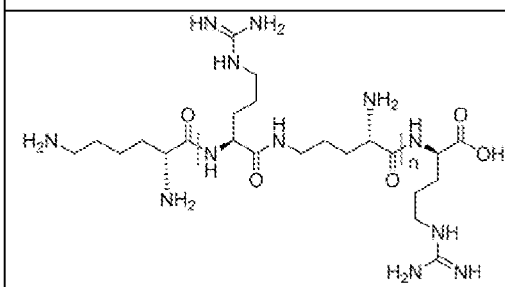 | _K_r_K_r_K_r_K_r_K_r_K_r (HC 4; SEQ ID NO: 18), where _K_ is ε-L-lysyl residue and r is D-arginyl residue |
| 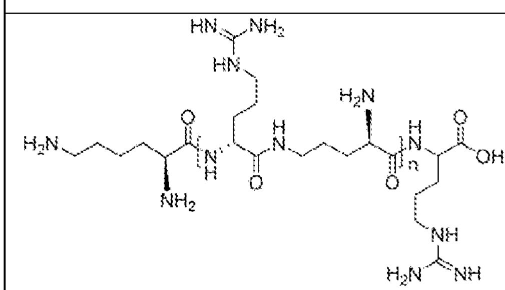 | _k_R_k_R_k_R_k_R_k_R_k_R (HC 6; SEQ ID NO: 19) where _k_ is ε-D-lysyl residue and R is L-arginyl residue |

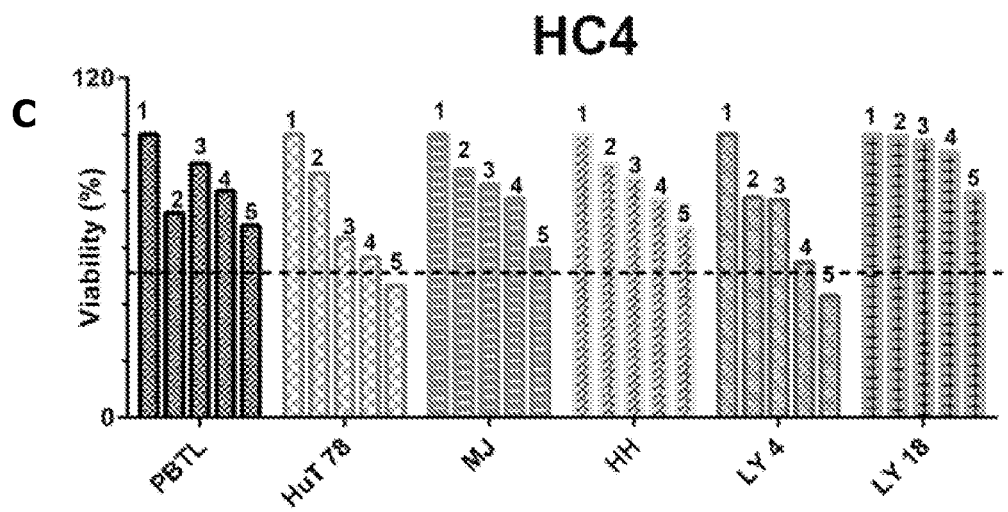
Figure 22 (Continued)
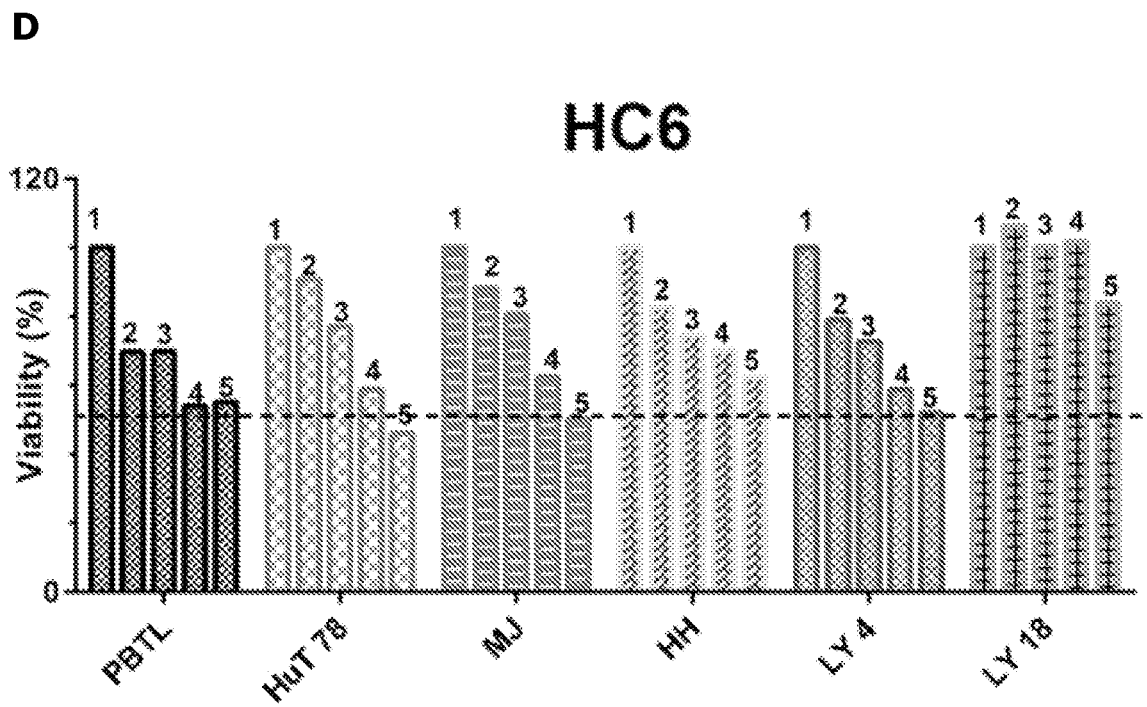

SEQUENCE LISTING

<160> NUMBER OF SEQ ID NOS: 25

<210> SEQ ID NO 1
<211> LENGTH: 14
<212> TYPE: PRT
<213> ORGANISM: Artificial Sequence
<220> FEATURE:
<223> OTHER INFORMATION: Mastoparan

<400> SEQUENCE: 1

Leu Lys Leu Lys Ser Ile Val Ser Trp Ala Lys Lys Val Leu
1               5                   10

<210> SEQ ID NO 2
<211> LENGTH: 26
<212> TYPE: PRT
<213> ORGANISM: Artificial Sequence
<220> FEATURE:
<223> OTHER INFORMATION: Melittin

```
<400> SEQUENCE: 2

Gly Ile Gly Ala Val Leu Lys Val Leu Thr Thr Gly Leu Pro Ala Leu
1               5                   10                  15

Ile Ser Trp Ile Lys Arg Lys Arg Gln Gln
                20                  25

<210> SEQ ID NO 3
<211> LENGTH: 12
<212> TYPE: PRT
<213> ORGANISM: Artificial Sequence
<220> FEATURE:
<223> OTHER INFORMATION: HC1

<400> SEQUENCE: 3

Lys Arg Lys Arg Lys Arg Lys Arg Lys Arg Lys Arg
1               5                   10

<210> SEQ ID NO 4
<211> LENGTH: 23
<212> TYPE: PRT
<213> ORGANISM: Artificial Sequence
<220> FEATURE:
<223> OTHER INFORMATION: Magainin

<400> SEQUENCE: 4

Gly Ile Gly Lys Phe Leu His Ser Ala Lys Lys Phe Gly Lys Ala Phe
1               5                   10                  15

Val Gly Glu Ile Met Asn Ser
                20

<210> SEQ ID NO 5
<211> LENGTH: 24
<212> TYPE: PRT
<213> ORGANISM: Artificial Sequence
<220> FEATURE:
<223> OTHER INFORMATION: Pandinin

<400> SEQUENCE: 5

Phe Trp Gly Ala Leu Ala Lys Gly Ala Leu Lys Leu Ile Pro Ser Leu
1               5                   10                  15

Phe Ser Ser Phe Ser Lys Lys Asp
                20

<210> SEQ ID NO 6
<211> LENGTH: 37
<212> TYPE: PRT
<213> ORGANISM: Artificial Sequence
<220> FEATURE:
<223> OTHER INFORMATION: Cecropin A

<400> SEQUENCE: 6

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
                20                  25                  30

Thr Gln Ile Ala Lys
        35

<210> SEQ ID NO 7
<211> LENGTH: 14
<212> TYPE: PRT
<213> ORGANISM: Artificial Sequence
<220> FEATURE:
<223> OTHER INFORMATION: Mastoparan; MB1
```

```
<220> FEATURE:
<221> NAME/KEY: MISC_FEATURE
<222> LOCATION: (2)..(2)
<223> OTHER INFORMATION: Epsilon Lysine

<400> SEQUENCE: 7

Leu Lys Leu Lys Ser Ile Val Ser Trp Ala Lys Lys Val Leu
 1               5                  10

<210> SEQ ID NO 8
<211> LENGTH: 14
<212> TYPE: PRT
<213> ORGANISM: Artificial Sequence
<220> FEATURE:
<223> OTHER INFORMATION: Mastoparan; MB2
<220> FEATURE:
<221> NAME/KEY: MISC_FEATURE
<222> LOCATION: (4)..(4)
<223> OTHER INFORMATION: Epsilon Lysine

<400> SEQUENCE: 8

Leu Lys Leu Lys Ser Ile Val Ser Trp Ala Lys Lys Val Leu
 1               5                  10

<210> SEQ ID NO 9
<211> LENGTH: 14
<212> TYPE: PRT
<213> ORGANISM: Artificial Sequence
<220> FEATURE:
<223> OTHER INFORMATION: Mastoparan; MB3
<220> FEATURE:
<221> NAME/KEY: MISC_FEATURE
<222> LOCATION: (11)..(11)
<223> OTHER INFORMATION: Epsilon Lysine

<400> SEQUENCE: 9

Leu Lys Leu Lys Ser Ile Val Ser Trp Ala Lys Lys Val Leu
 1               5                  10

<210> SEQ ID NO 10
<211> LENGTH: 14
<212> TYPE: PRT
<213> ORGANISM: Artificial Sequence
<220> FEATURE:
<223> OTHER INFORMATION: Mastoparan; MB4
<220> FEATURE:
<221> NAME/KEY: MISC_FEATURE
<222> LOCATION: (12)..(12)
<223> OTHER INFORMATION: Epsilon Lysine

<400> SEQUENCE: 10

Leu Lys Leu Lys Ser Ile Val Ser Trp Ala Lys Lys Val Leu
 1               5                  10

<210> SEQ ID NO 11
<211> LENGTH: 26
<212> TYPE: PRT
<213> ORGANISM: Artificial Sequence
<220> FEATURE:
<223> OTHER INFORMATION: Melittin; Peptide 1
<220> FEATURE:
<221> NAME/KEY: MISC_FEATURE
<222> LOCATION: (23)..(23)
<223> OTHER INFORMATION: Epsilon Lysine
```

```
<400> SEQUENCE: 11

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 12
<211> LENGTH: 26
<212> TYPE: PRT
<213> ORGANISM: Artificial Sequence
<220> FEATURE:
<223> OTHER INFORMATION: Melittin; Peptide 2
<220> FEATURE:
<221> NAME/KEY: MISC_FEATURE
<222> LOCATION: (21)..(21)
<223> OTHER INFORMATION: Epsilon Lysine

<400> SEQUENCE: 12

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 13
<211> LENGTH: 26
<212> TYPE: PRT
<213> ORGANISM: Artificial Sequence
<220> FEATURE:
<223> OTHER INFORMATION: Melittin; Peptide 3
<220> FEATURE:
<221> NAME/KEY: MISC_FEATURE
<222> LOCATION: (7)..(7)
<223> OTHER INFORMATION: Epsilon Lysine

<400> SEQUENCE: 13

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 14
<211> LENGTH: 26
<212> TYPE: PRT
<213> ORGANISM: Artificial Sequence
<220> FEATURE:
<223> OTHER INFORMATION: Melittin; Peptide 4
<220> FEATURE:
<221> NAME/KEY: MISC_FEATURE
<222> LOCATION: (7)..(7)
<223> OTHER INFORMATION: Epsilon Lysine
<220> FEATURE:
<221> NAME/KEY: MISC_FEATURE
<222> LOCATION: (21)..(21)
<223> OTHER INFORMATION: Epsilon Lysine
<220> FEATURE:
<221> NAME/KEY: MISC_FEATURE
<222> LOCATION: (23)..(23)
<223> OTHER INFORMATION: Epsilon Lysine

<400> SEQUENCE: 14

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25
```

```
<210> SEQ ID NO 15
<211> LENGTH: 26
<212> TYPE: PRT
<213> ORGANISM: Artificial Sequence
<220> FEATURE:
<223> OTHER INFORMATION: Melittin; Peptide 5
<220> FEATURE:
<221> NAME/KEY: MISC_FEATURE
<222> LOCATION: (7)..(7)
<223> OTHER INFORMATION: Epsilon Lysine
<220> FEATURE:
<221> NAME/KEY: MISC_FEATURE
<222> LOCATION: (21)..(21)
<223> OTHER INFORMATION: Epsilon Lysine

<400> SEQUENCE: 15

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 16
<211> LENGTH: 26
<212> TYPE: PRT
<213> ORGANISM: Artificial Sequence
<220> FEATURE:
<223> OTHER INFORMATION: Melittin; Peptide 6
<220> FEATURE:
<221> NAME/KEY: MISC_FEATURE
<222> LOCATION: (7)..(7)
<223> OTHER INFORMATION: Epsilon Lysine
<220> FEATURE:
<221> NAME/KEY: MISC_FEATURE
<222> LOCATION: (23)..(23)
<223> OTHER INFORMATION: Epsilon Lysine

<400> SEQUENCE: 16

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 17
<211> LENGTH: 12
<212> TYPE: PRT
<213> ORGANISM: Artificial Sequence
<220> FEATURE:
<223> OTHER INFORMATION: HC2
<220> FEATURE:
<221> NAME/KEY: MISC_FEATURE
<222> LOCATION: (1)..(1)
<223> OTHER INFORMATION: Epsilon Lysine
<220> FEATURE:
<221> NAME/KEY: MISC_FEATURE
<222> LOCATION: (3)..(3)
<223> OTHER INFORMATION: Epsilon Lysine
<220> FEATURE:
<221> NAME/KEY: MISC_FEATURE
<222> LOCATION: (5)..(5)
<223> OTHER INFORMATION: Epsilon Lysine
<220> FEATURE:
<221> NAME/KEY: MISC_FEATURE
<222> LOCATION: (7)..(7)
<223> OTHER INFORMATION: Epsilon Lysine
<220> FEATURE:
<221> NAME/KEY: MISC_FEATURE
<222> LOCATION: (9)..(9)
<223> OTHER INFORMATION: Epsilon Lysine
<220> FEATURE:
<221> NAME/KEY: MISC_FEATURE
<222> LOCATION: (11)..(11)
<223> OTHER INFORMATION: Epsilon Lysine
```

-continued

```
<400> SEQUENCE: 17

Lys Arg Lys Arg Lys Arg Lys Arg Lys Arg Lys Arg
1               5                   10

<210> SEQ ID NO 18
<211> LENGTH: 12
<212> TYPE: PRT
<213> ORGANISM: Artificial Sequence
<220> FEATURE:
<223> OTHER INFORMATION: HC4
<220> FEATURE:
<221> NAME/KEY: MISC_FEATURE
<222> LOCATION: (1)..(1)
<223> OTHER INFORMATION: Epsilon Lysine
<220> FEATURE:
<221> NAME/KEY: MISC_FEATURE
<222> LOCATION: (2)..(2)
<223> OTHER INFORMATION: D-Arginine or D-Arginyl
<220> FEATURE:
<221> NAME/KEY: MISC_FEATURE
<222> LOCATION: (3)..(3)
<223> OTHER INFORMATION: Epsilon Lysine
<220> FEATURE:
<221> NAME/KEY: MISC_FEATURE
<222> LOCATION: (4)..(4)
<223> OTHER INFORMATION: D-Arginine or D-Arginyl
<220> FEATURE:
<221> NAME/KEY: MISC_FEATURE
<222> LOCATION: (5)..(5)
<223> OTHER INFORMATION: Epsilon Lysine
<220> FEATURE:
<221> NAME/KEY: MISC_FEATURE
<222> LOCATION: (6)..(6)
<223> OTHER INFORMATION: D-Arginine or D-Arginyl
<220> FEATURE:
<221> NAME/KEY: MISC_FEATURE
<222> LOCATION: (7)..(7)
<223> OTHER INFORMATION: Epsilon Lysine
<220> FEATURE:
<221> NAME/KEY: MISC_FEATURE
<222> LOCATION: (8)..(8)
<223> OTHER INFORMATION: D-Arginine or D-Arginyl
<220> FEATURE:
<221> NAME/KEY: MISC_FEATURE
<222> LOCATION: (9)..(9)
<223> OTHER INFORMATION: Epsilon Lysine
<220> FEATURE:
<221> NAME/KEY: MISC_FEATURE
<222> LOCATION: (10)..(10)
<223> OTHER INFORMATION: D-Arginine or D-Arginyl
<220> FEATURE:
<221> NAME/KEY: MISC_FEATURE
<222> LOCATION: (11)..(11)
<223> OTHER INFORMATION: Epsilon Lysine
<220> FEATURE:
<221> NAME/KEY: MISC_FEATURE
<222> LOCATION: (12)..(12)
<223> OTHER INFORMATION: D-Arginine or D-Arginyl

<400> SEQUENCE: 18

Lys Arg Lys Arg Lys Arg Lys Arg Lys Arg Lys Arg
1               5                   10

<210> SEQ ID NO 19
<211> LENGTH: 12
<212> TYPE: PRT
<213> ORGANISM: Artificial Sequence
<220> FEATURE:
<223> OTHER INFORMATION: HC6
<220> FEATURE:
<221> NAME/KEY: MISC_FEATURE
<222> LOCATION: (1)..(1)
<223> OTHER INFORMATION: Epsilon-D-Lysine
```

```
<220> FEATURE:
<221> NAME/KEY: MISC_FEATURE
<222> LOCATION: (3)..(3)
<223> OTHER INFORMATION: Epsilon-D-Lysine
<220> FEATURE:
<221> NAME/KEY: MISC_FEATURE
<222> LOCATION: (5)..(5)
<223> OTHER INFORMATION: Epsilon-D-Lysine
<220> FEATURE:
<221> NAME/KEY: MISC_FEATURE
<222> LOCATION: (7)..(7)
<223> OTHER INFORMATION: Epsilon-D-Lysine
<220> FEATURE:
<221> NAME/KEY: MISC_FEATURE
<222> LOCATION: (9)..(9)
<223> OTHER INFORMATION: Epsilon-D-Lysine
<220> FEATURE:
<221> NAME/KEY: MISC_FEATURE
<222> LOCATION: (11)..(11)
<223> OTHER INFORMATION: Epsilon-D-Lysine

<400> SEQUENCE: 19

Lys Arg Lys Arg Lys Arg Lys Arg Lys Arg Lys Arg
1               5                   10

<210> SEQ ID NO 20
<211> LENGTH: 26
<212> TYPE: PRT
<213> ORGANISM: Artificial sequence
<220> FEATURE:
<223> OTHER INFORMATION: modified peptide; Table 4
<220> FEATURE:
<221> NAME/KEY: Misc
<222> LOCATION: (1)..(26)
<223> OTHER INFORMATION: D-amino acids

<400> SEQUENCE: 20

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 21
<211> LENGTH: 26
<212> TYPE: PRT
<213> ORGANISM: Artificial sequence
<220> FEATURE:
<223> OTHER INFORMATION: modified peptide; Table 4
<220> FEATURE:
<221> NAME/KEY: misc_feature
<222> LOCATION: (5)..(5)
<223> OTHER INFORMATION: D-Valine
<220> FEATURE:
<221> NAME/KEY: misc_feature
<222> LOCATION: (8)..(8)
<223> OTHER INFORMATION: D-Valine
<220> FEATURE:
<221> NAME/KEY: misc_feature
<222> LOCATION: (17)..(17)
<223> OTHER INFORMATION: D-Isoleucine
<220> FEATURE:
<221> NAME/KEY: misc_feature
<222> LOCATION: (21)..(21)
<223> OTHER INFORMATION: D-lysine

<400> SEQUENCE: 21

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25
```

```
<210> SEQ ID NO 22
<211> LENGTH: 26
<212> TYPE: PRT
<213> ORGANISM: Artificial sequence
<220> FEATURE:
<223> OTHER INFORMATION: modified peptide; Table 4
<220> FEATURE:
<221> NAME/KEY: misc
<222> LOCATION: (6)..(6)
<223> OTHER INFORMATION: peptoid residue
<220> FEATURE:
<221> NAME/KEY: misc
<222> LOCATION: (13)..(13)
<223> OTHER INFORMATION: peptoid residue
<220> FEATURE:
<221> NAME/KEY: misc
<222> LOCATION: (20)..(20)
<223> OTHER INFORMATION: peptoid residue

<400> SEQUENCE: 22

Gly Ile Gly Ala Val Lys Lys Val Leu Thr Thr Gly Lys Pro Ala Leu
1               5                   10                  15

Ile Ser Trp Lys Lys Arg Lys Arg Gln Gln
            20                  25

<210> SEQ ID NO 23
<211> LENGTH: 28
<212> TYPE: PRT
<213> ORGANISM: Artificial sequence
<220> FEATURE:
<223> OTHER INFORMATION: linear peptide; Table 4

<400> SEQUENCE: 23

Cys Gly Ile Gly Ala Val Leu Lys Val Leu Thr Thr Gly Leu Pro Ala
1               5                   10                  15

Leu Ile Ser Trp Ile Lys Arg Lys Arg Gln Gln Cys
            20                  25

<210> SEQ ID NO 24
<211> LENGTH: 26
<212> TYPE: PRT
<213> ORGANISM: Artificial sequence
<220> FEATURE:
<223> OTHER INFORMATION: modified peptide; Table 4

<400> SEQUENCE: 24

Gly Ile Gly Ala Val Leu Lys Val Leu Thr Thr Gly Leu Cys Ala Leu
1               5                   10                  15

Ile Ser Trp Ile Lys Arg Lys Arg Gln Gln
            20                  25

<210> SEQ ID NO 25
<211> LENGTH: 26
<212> TYPE: PRT
<213> ORGANISM: Artificial sequence
<220> FEATURE:
<223> OTHER INFORMATION: modified peptide; Table 4
<220> FEATURE:
<221> NAME/KEY: Misc
<222> LOCATION: (7)..(7)
<223> OTHER INFORMATION: Succinylation
<220> FEATURE:
<221> NAME/KEY: Misc
<222> LOCATION: (21)..(21)
<223> OTHER INFORMATION: Succinylation
<220> FEATURE:
<221> NAME/KEY: Misc
<222> LOCATION: (23)..(23)
<223> OTHER INFORMATION: Succinylation
```

-continued

```
<400> SEQUENCE: 25

Gly Ile Gly Ala Val Leu Lys Val Leu Thr Thr Gly Leu Pro Ala Leu
1               5                   10                  15

Ile Ser Trp Ile Lys Arg Lys Arg Gln Gln
                20                  25
```

ANTIMICROBIAL PEPTIDES COMPRISING EPSILON LYSINE RESIDUES

CROSS-REFERENCE TO RELATED APPLICATIONS

This application is a 35 U.S.C. § 372 national phase application of PCT Application PCT/SG2017/050548, filed Oct. 31, 2017, which claims the benefit of priority of Singapore provisional application No. 10201609136R, filed 1 Nov. 2016, the entire contents of each of which are incorporated herein by reference in its entirety for all purposes.

STATEMENT REGARDING ELECTRONIC FILING OF A SEQUENCE LISTING

A Sequence Listing in ASCII text format, submitted under 37 C.F.R. § 1.821, entitled 9875-16_ST25.txt, 8,613 bytes in size, generated on Apr. 30, 2019 and filed via EFS-Web, is provided in lieu of a paper copy. This Sequence Listing is hereby incorporated by reference into the specification for its disclosures.

FIELD OF THE INVENTION

The present invention generally relates to design of peptides and methods for their use.

BACKGROUND OF THE INVENTION

The widespread evolution of antibiotic-resistant bacteria/fungi poses considerable threat to the public health and undermines the decades of benefits achieved with antibiotic development. Owing to unfavorable economic returns and regulatory challenges in gaining approvals, there has been a marked decline in the discovery and the development of new antibiotics. A number of cationic polymers or biocides have been used over the past 50 years in both medical and non-medical applications.

In view of the widespread evolution of bacteria, there is a need to provide an alternative antimicrobial peptide.

SUMMARY OF THE INVENTION

In one aspect, there is provided an isolated peptide. The peptide comprising at least five amino acid residues of which there is: at least one amino acid residue selected from the group consisting of D-epsilon-lysine, L-epsilon-lysine, D-delta-ornithine, L-delta-ornithine, D-gamma-2,4-diaminobutyric acid, L-gamma-2,4-diaminobutyric acid, D-beta-2,3-diaminopropionic acid, and L-beta-2,3-diaminopropionic acid amino acid residues; and at least one other amino acid residue selected from the group consisting of non-epsilon-lysine, non-delta-ornithine, non-gamma-2,4-diaminobutyric acid, and non-beta-2,3-diaminopropionic acid amino acid residue; wherein the peptide has reduced or no cytotoxicity when compared to an equivalent peptide without the at least one amino acid residue selected from the group consisting of epsilon-lysine, delta-ornithine, gamma-2,4-diaminobutyric acid, and beta-2,3-diaminopropionic acid residue. In one embodiment, the peptide does not comprise epsilon-polylysine. In another embodiment, with respect to the lysine residues in the peptide, the peptide comprises either epsilon-lysine amino acid residues and alpha-lysine amino acid residues or only epsilon-lysine amino acid residues. In yet another embodiment, the peptide comprises from 5 to 100 amino acids.

In yet another embodiment, the peptide has the amino acid sequence of LKLKSIVSWAKKVL (SEQ ID NO: 1), wherein at least one of the lysine residues (K) is an epsilon-lysine residue. In yet another embodiment, when the peptide comprises one epsilon-lysine residue, the epsilon-lysine residue is located at position 2 (SEQ ID NO: 7), or position 4 (SEQ ID NO: 8), or position 11 (SEQ ID NO: 9), or position 12 (SEQ ID NO: 10).

In yet another embodiment, the peptide has the amino acid sequence of GIGAVLKVLTTGLPALISWIKRKRQQ (SEQ ID NO: 2), wherein at least one of the lysine residues is an epsilon-lysine residue. In yet another embodiment, when the peptide comprises (i) one epsilon-lysine residue, the epsilon-lysine residue is located at position 7 (SEQ ID NO: 13), or at position 21 (SEQ ID NO: 12), or at position 23 (SEQ ID NO: 11); or (ii) two epsilon-lysine residues, the epsilon-lysine residues are located at position 7 and position 21 (SEQ ID NO: 15), or at position 7 and position 23 (SEQ ID NO: 16); or (iii) three epsilon-lysine residues, the three epsilon-lysine residues are located at position 7, position 21, and position 23 (SEQ ID NO: 14).

In yet another embodiment, the peptide has the amino acid sequence of KRKRKRKRKRKR (SEQ ID NO: 3), wherein at least one of the lysine residues is an epsilon-lysine residue. In yet another embodiment, the peptide comprises six epsilon-lysine residues, the six epsilon-lysine residues are located at position 1, position 3, position 5, position 7, position 9, and position 11 (SEQ ID NO: 17, or SEQ ID NO: 18, or SEQ ID NO: 19).

In another aspect, there is provided a peptide as described herein for use in therapy or medicine.

In yet another aspect, there is provided a pharmaceutical composition comprising one or more peptide(s) as described herein.

In yet another aspect, there is provided a kit comprising one or more peptide(s) as described herein and/or a composition as described herein.

In yet another aspect, there is provided an ophthalmic preparation comprising one or more peptide(s) as described herein and/or a composition as described herein.

In yet another aspect, there is provided a method of inhibiting the growth of a microorganism or managing microbial colonization comprising administration of a pharmaceutically effective amount of a peptide as described herein and/or a composition as described herein. In yet another embodiment, inhibiting the growth of a microorganism treats a microbial infection. In yet another embodiment, the microorganism is a bacterium, a fungus, a drug resistant bacterium, or a drug resistant fungus. In yet another embodiment, the bacterium is selected from the group consisting of *Acinetobacter baumannii, Enterobacter cloacae, Escherichia coli, Klebsiella pneumoniae, Pseudomonas aeruginosa, Staphylococcus aureus*, MRSA, *Enterococcus faecalis* and *Enterococcus faecium*. In yet another embodiment, the drug resistant bacterium is selected from the group consisting of carbapenam-resistant *Enterobacter* strains (CRE), Methicillin-resistant *Staphylococcus aureus* (MRSA), Vancomycin-resistant Enterococci (VRE), polymixin B-resistant *Enterobacter cloacae*, drug-resistant *Acinetobacter baumannii*, and prolific biofilm forming *P. aeruginosa* and *S. epidermidis* strains. In yet another embodiment, the fungus is selected from the group consisting of *Candida albicans, Candida parpsilosis, Candida tropicalis, Fusarium solani, Fusarium oxysporum*, and *Aspergillus fumigatus*. In yet another embodiment, the drug resistant fungus is selected from the group consisting of *Fusarium solani*, *Fusarium oxysporum*, and *Aspergillus fumigatus*. In yet another embodiment, the microbial infection is selected from the group consisting of *Staphylococcus aureus* keratitis, *Pseudomonas aeruginosa* keratitis, fungal keratitis, *Candida* keratitis, and *Fusarium* keratitis.

In another aspect, there is provided a method of improving the therapeutic index (safety) of an isolated peptide, the peptide comprising at least five amino acid residues, comprising at least one amino acid residue selected from the group consisting of D-epsilon-lysine, L-epsilon-lysine, D-delta-ornithine, L-delta-ornithine, D-gamma-2,4-diaminobutyric acid, L-gamma-2,4-diaminobutyric acid, D-beta-2,3-diaminopropionic acid, and L-beta-2,3-diaminopropionic acid amino acid residue and at least one other selected from the group consisting of non-epsilon-lysine, non-delta-ornithine, non-gamma-2,4-diaminobutyric acid, and non-beta-2,3-diaminopropionic acid amino acid residue, and wherein the peptide has reduced cytotoxicity when compared to equivalent peptide without the at least one selected from the group consisting of epsilon-lysine, delta-ornithine, gamma-2,4-diaminobutyric acid, and beta-2,3-diaminopropionic acid residue, the method comprising modifying at least one of the lysine residues to at least one selected from the group consisting of epsilon-lysine, delta-ornithine, gamma-2,4-diaminobutyric acid, and beta-2,3-diaminopropionic acid.

In another aspect, there is provided a method of treating proliferative disease and/or inflammation comprising administration of a pharmaceutically effective amount of a peptide as described herein and/or a composition as described herein.

BRIEF DESCRIPTION OF THE DRAWINGS

The invention will be better understood with reference to the detailed description when considered in conjunction with the non-limiting examples and the accompanying drawings, in which:

FIG. 1A shows a graphical representation of the chemical structure of an alpha-polylysine. FIG. 1B shows a graphical representation of the chemical structure of an epsilon-polylysine. FIG. 1C shows a scatter plot correlating the grand-mean MIC (Minimum Inhibitory Concentration) values of alpha-polylysine and epsilon-polylysine against 5 different strains each of *S. aureus*, *P. aeruginosa* and *C. albicans*. Thus, FIG. 1 illustrates that grand mean MIC (GM-MIC) of both the polymers was similar against Gram-positive and Gram-negative strains whereas εPL displayed lower MIC than αPL against *C. albicans* strains.

FIG. 2A shows a scatter plot representing the cytotoxicity of alpha-polylysine for primary human dermal fibroblasts (HDF) cells assessed by MTS cell proliferation assay. FIG. 2B shows a scatter plot representing the cytotoxicity of epsilon-polylysine for primary human dermal fibroblasts (HDF) cells assessed by MTS cell proliferation assay. Thus, FIG. 2 illustrates that alpha-polylysine is less cytotoxic than epsilon-polylysine for primary human dermal fibroblasts (HDF) cells.

FIG. 3A shows a set of High Content Analysis (HCA) images showing the cytotoxicity of alpha-polylysine and epsilon-polylysine for primary human dermal fibroblasts (HDFs) at various concentrations. FIG. 3B shows a set of images representing heat map showing the concentration-dependent changes in cell health of primary human dermal fibroblasts (HDFs) after exposure to various concentration of alpha-polylysine and epsilon-polylysine. Nocodazole (5 µg/ml), a cytotoxic drug is used as the negative control. Thus, FIG. 3 illustrates that primary human dermal fibroblasts (HDFs) exposed to alpha-polylysine displayed considerable abnormalities in cellular morphology whereas cells exposed to epsilon-polylysine remained similar as untreated control thereby further showing that epsilon-polylysine is less cytotoxic than alpha-polylysine.

FIG. 4 shows a bar graph representing the quantitative estimation of live/dead cells ratio after exposure to epsilon-polylysine. Prolific biofilm-forming PA01 strains were used. MIC of epsilon-polylysine against PA01 was 16 mg/ml. For comparison, the biofilm eradicating properties of cationic peptide antibiotic polymyxin B is also shown. Thus, FIG. 4 illustrates that epsilon-polylysine is more effective in reducing biofilm when compared to cationic cyclic lipopeptide, polymyxin B.

FIG. 5A shows a line graph representing quantitative estimation of fungal hyphal survival (determined by MTT assay) after 16 hours of exposure to various concentrations of epsilon-polylysine. FIG. 5B shows a line graph representing quantitative estimation of fungal hyphal survival (determined by MTT assay) after 16 hours of exposure to various concentrations of natamycin. Thus, FIG. 5 illustrates that epsilon-polylysine is more effective in reducing fungal hyphal survival when compared to FDA approved ophthalmic antifungal, natamycin.

FIG. 6 illustrates the potent bactericidal properties of epsilon-polylysine against diverse disease causing and drug-resistant pathogens.

FIG. 7 illustrates that eyes treated with epsilon-polylysine displayed significant decrease in chemosis and discharge, corneal haze and conjunctival redness in comparison to other groups.

FIG. 8A shows a set of images representing the result of Anterior Segment Optical Coherence Tomography (AS-OCT) examination of infected and treated rabbit cornea. FIG. 8B shows a graph representing the progressive changes in central corneal thickness after application of PBS, epsilon-polylysine, and zymar. A total of 6 rabbits were included for each application. FIG. 8C shows a graph representing the microbiological enumeration of bacterial viability in the excised cornea at 72 hours post treatment (p.t.) of epsilon-polylysine and zymar. Thus, FIG. 8 illustrates that epsilon-polylysine treated eyes displayed significant decrease in edema at 24 h post treatment in comparison to Zymar® or PBS treated eyes. Additionally, both epsilon-polylysine and Zymar treated cornea did not show the presence of viable bacteria whereas PBS treated cornea contained 4.1±0.13 $\log_{10}$ CFU/ml of bacteria.

FIG. 9A shows a set of slit lamp biomicroscopy images comparing the efficacy of 0.3% (w/v) epsilon-polylysine in a rabbit model of *Pseudomonas* keratitis. *P. aeruginosa* ATCC 9027 strain was used to infect the cornea. An initial inoculum of $5\times10^6$ CFU/ml (50 µl) was applied to the wounded cornea and the image was taken at 24 hours post infection (p.i.). Treatment was started at this point by applying 50 µl of epsilon-polylysine or Tobrex (0.3% Tobramcyin) was applied to the infected eye at 4 times/day for 3 days. Images were taken at 24, 48, 72 hours post treatment (p.t.). Vehicle alone (10 mM PBS) served as the control. A total of 10 rabbits were used for epsilon-polylysine treatment and 4 each for PBS and Tobrex. FIG. 9B shows a graph representing progressive changes in corneal thickness before and after infection/treatment. FIG. 9C shows a graph representing microbiological enumeration of bacterial viability in the infected cornea at 72 hours post treatment (p.t.). Thus, FIG. 9 illustrates that epsilon-polylysine is effective in clearing *P. aeruginosa* infections and that epsilon-polylysine possesses antimicrobial properties that are suitable for topical applications.

FIG. 10A shows a line graph representing change in Minimum Inhibitory Concentration (MIC) values with increasing number of epsilon-lysines. Data for the graph was taken from Shima. et al. (J Antibiot (Tokyo). 1984 November; 37(11):1449-55.) FIG. 10B shows a bar graph representing antimicrobial activity of HC1 and HC2 peptides after incubation with trypsin for 1 hour. A complete loss of activity for HC1 was observed while HC2 elicited 6 $\log_{10}$ decrease (99.9999%) in the bacterial viability. Thus, FIG. 10 illustrates that peptide HC2 (i.e. a peptide having 12 residues (6 lysine and arginine pairs) and wherein the lysine residues are connected via epsilon linkage) has antimicrobial activity that is retained even after 1 hour incubation with trypsin.

FIG. 11A shows the cytotoxicity of melittin and melittin analogues (Peptide 1, 2, and 3) wherein the three alpha-lysyl residues are replaced with epsilon-lysyl residues. FIG. 11B shows the cytotoxicity of melittin and melittin analogues (Peptide 4, 5, and 6) carrying more than one ε-lysyl residues. Thus, FIG. 11 illustrates that epsilon-lysinylation of alpha-lysines in mellitin may amiolerate the selectivity of pore forming melittin, thereby enhancing the therapeutic potential.

FIG. 12 illustrates that no apparent induction of cytokine production from human primary blood T-cell lymphocytes (PBTLs), thus confirming non-immunogenic nature of the peptides.

FIGS. 13A & B shows a line graph representing amount of fluorescent calcein dye leakage from microbial model large unilamellar vesicles (LUVs) upon addition of peptides to the LUVs. FIGS. 13C & D shows a line graph representing amount of fluorescent calcein dye leakage from mammalian model large unilamellar vesicles (LUVs) upon addition of peptides to the LUVs. Thus, FIG. 13 illustrates that epsilon-lysylation of melittin attenuated the interaction of the peptides with mammalian membrane.

FIG. 14 illustrates that epsilon-lysine substitution at various position in mastoparan B peptide reduces the cytotoxicity of mastoparan B.

FIG. 15A shows a confocal image of untreated hDFs showing the intact cytoskeleton and nuclear morphology. FIG. 15B shows a confocal image of hDFs infected with PAO1 gfp strains (multiplicity of infection, MOI=25) showing the deformed cell morphology. Note the significant presence of PAO1 cells (indicated by white arrows) proximal to the actin filaments of hDFs. FIG. 15C shows a confocal image depicting the effect of epsilon-polylysine (1 mg/ml) in a prevention mode (i.e., prior to microbial infection). FIG. 15D shows a confocal image depicting the effect of εPL (1 mg/ml) in a regression mode (i.e., 2 h post infection of the host cells). Note the absence of any bacterial cells under both the conditions (as shown on FIGS. 15C and 15D), indicating potent antimicrobial activity of the polymer. The magnified area is indicated in white box. Thus, FIG. 15 illustrates that epsilon-polylysine, which are applied prior to infection (prevention) or after infection (regression), attenuates the adverse effect of *Pseudomonas aeruginosa* and *Staphylococcus aureus* on human Dermal Fibroblasts (hDFs).

FIG. 16 illustrates that epsilon-polylysine binding to lipopolysaccharide (LPS), which is a key component of the outer membrane of the bacteria, attenuates adverse effect of the endotoxin.

FIG. 17A is a set of photographs showing the effect of 1 mg/ml epsilon-polylysine on cell migration of human Dermal Fibroblasts (hDFs) at two different time points. Note the presence of a higher density of cells at the scratched area after epsilon-polylysine addition compared to no treatment at 14 h. FIG. 17B is a line graph showing epsilon-polylysine concentration-dependent temporal changes in cell migration in comparison to untreated or fibroblast growth factors. FIG. 17C is a line graph showing inhibitory effect of bacterial secretomes collected from *S. aureus* ATCC 29213 strains is abrogated by epsilon-polylysine (1 mg/ml). At 25% (v/v), the *S. aureus* secretomes inhibited the cell migration. All the results are an average of 2 independent duplicate experiments. Thus, FIG. 17 illustrates that epsilon-polylysine is biocompatible, promotes human Dermal Fibroblasts (hDFs) migration in vitro and averts the adverse effects of bacterial secreted products.

FIG. 18A shows a set of photographs showing slit lamp examination result of injured cornea after treatment with epsilon-polylysine and vehicle. The wound area was determined by fluorescein staining. FIG. 18B is a line graph showing the average wound closure at each time points of measurements is expressed as mean±standard error of the mean. Thus, FIG. 18 illustrates that epsilon-polylysine did not impair the wound closure of the injured cornea and thus epsilon-polylysine is biocompatible.

FIG. 19 illustrates that epsilon-polylysine displayed potent anticancer activity against T-cell lymphoma, B-cell lymphoma and retinoblastoma cell lines.

FIG. 20A shows a line graph showing representative Sytox Green (SG) uptake assay of VRE 1002 bacterial cells upon exposure to various concentrations of melittin. The concentration of melittin is expressed in terms of MIC values. Note the substantial SG uptake was observed at and above MIC values. FIGS. 20B and 20C are a pair of bar graphs showing the comparison of SG uptake values of VRE (as shown on FIG. 20B) and *A. baumanni* (as shown on FIG. 20C) strains exposed to lethal concentrations of melittin and Peptide 5 and Peptide 6. FIG. 20D is a scatter plot depicting the relationship between SG uptake and bacterial lethality for various peptides. Note that substantial bactericidal properties (90-99% reduction in bacterial viability) were observed in spite of low the SG uptake values. Thus, FIG. 20 illustrates that even though the modified melittin peptides have poorer pore-forming properties than melittin, their bacterial lethality was similar to melittin.

FIG. 22 illustrates that the hypercharged peptides (HC1, HC2, HC4, and HC6) displayed varying degrees of cell killing in lymphoma cell lines in a dose dependent manner. Interestingly, PBL T-cells (PBTL) were less sensitive to these peptides compared to the lymphoma cell lines (HuT78, MJ, HH, Ly-4, and Ly-18).

BRIEF DESCRIPTION OF THE TABLES

Figure 1:
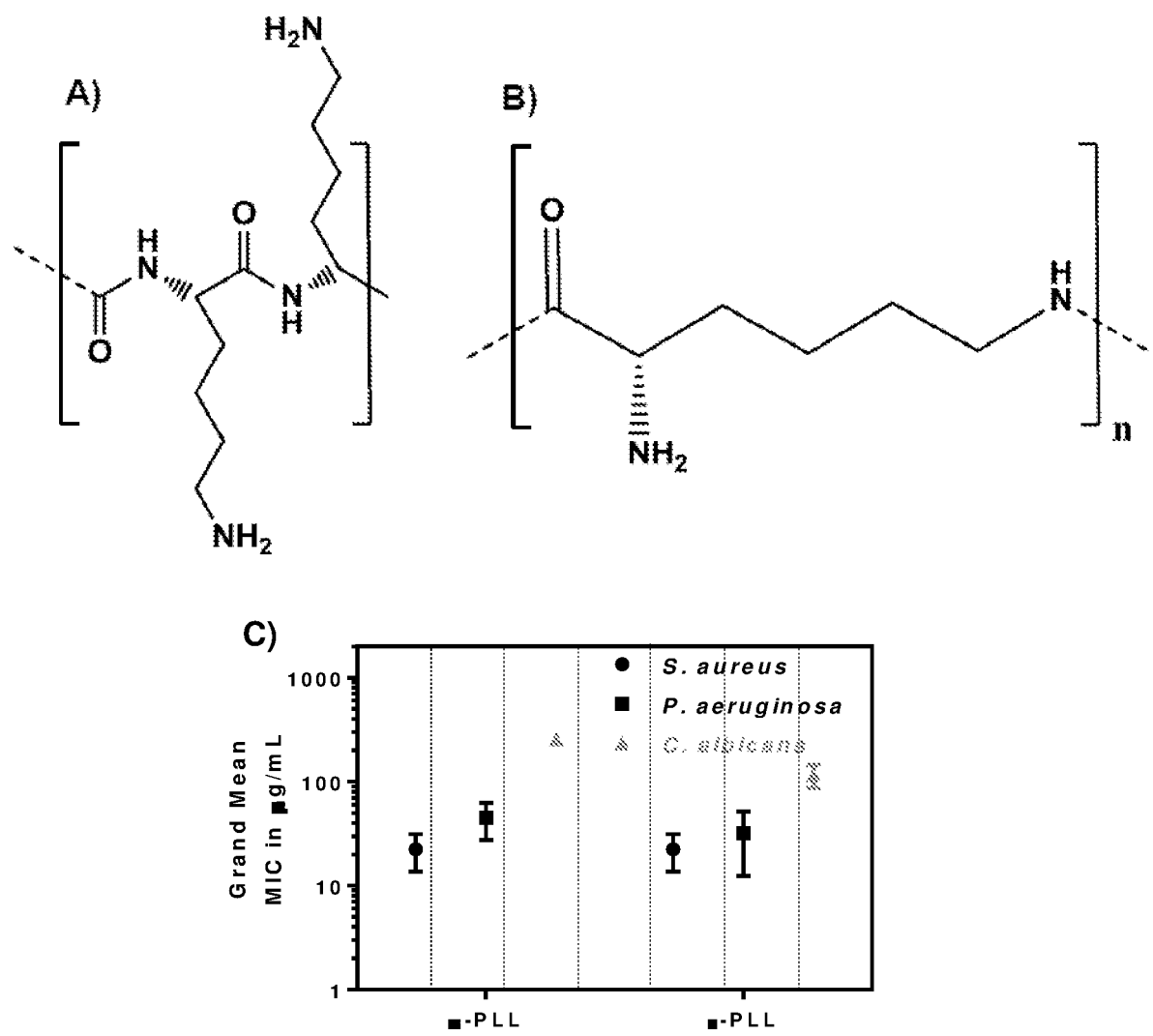
FIG. 1 shows comparison of alpha-polylysine and epsilon-polylysine.

Table 1 shows Minimum Inhibitory Concentration (MIC) of alpha-polylysine and epsilon-polylysine against a panel of bacteria and yeasts strains.

Table 2 shows Minimum Inhibitory Concentration (MIC) of epsilon-polylysine against a panel of drug resistant bacteria and fungi. The number of strains used is indicated in parenthesis.

Table 3 shows Minimum Inhibitory Concentration (MIC) of epsilon-polylysine mimetic peptides against panel of pathogens. The number of strains used is indicated in parenthesis.

Table 4 shows amino acid sequence and Minimum Inhibitory Concentration (MIC) and average therapeutic index values of melittin and modified peptides 1 to 4 against bacteria and yeast strains. Epsilon-lysine residue is indicated in italics and underlined.

Table 5 shows Minimum Inhibitory Concentration (MIC) of melittin, peptide 3, peptide 4, peptide 5 and peptide 6 against a panel of drug-resistant bacteria and against other pathogenic yeast strains.

Table 6 shows comparison of various chemical modifications of melittin peptide to improve membrane selectivity.

Table 7 shows Minimum Inhibitory Concentration (MIC) of mastoparans peptides against Vancomycin-resistant *Enterococcus* (VREs), Carbapenem-resistant enterobacteriaceae (CREs), *A. baumannii* and other bacterial and fungal strains. MIC values are given in ranges. $MIC_{50}$ indicates concentration at which 50% of the strains are susceptible. ε-lysyl residue is indicated in italics and underlined.

DETAILED DESCRIPTION OF THE PRESENT INVENTION

The ineffectiveness of available antibiotics combined with continuous decline in the number of new antibacterial drugs form a strong demand to develop alternative therapeutic strategies against multi-drug and pan-drug resistant microbial pathogens. Repurposing of antimicrobials used in human consumption is an alternative but less time-consuming and cost-effective approach for combating antibiotics-resistant microbial pathogens. Thus, there is an urgent need to provide alternative antimicrobial peptide.

It is known in the art that Epsilon-polylysine (εPL) is a naturally occurring homopolyamide in which the backbone amide group is formed between alpha-carboxyl and epsilon-amino group of the amino acid lysine and contains 25-35 L-lysine residues (FIG. 1). Epsilon-polylysine is a generally regarded as the safe materials (GRAS) approved by the United States Food and Drug Administration (US FDA) for food consumption.

Without wishing to be bound by theory, it is believed that the antimicrobial properties and the biosafety of epsilon-polylysine have stemmed from a combination of two characteristics, which are (1) the stretch of repeated lysine residues and (2) the epsilon linkages that connect one lysine residue to the next. The inventors of the present disclosure have surprisingly found that an isolated peptide does not necessarily need to have those two characteristics above in order to have antimicrobial and/or anticancer properties.

In light of the finding above, the inventors of the present disclosure have provided alternative antimicrobial peptides. The inventors of the present disclosure have found that there are peptides that have antimicrobial properties but that are also cytotoxic or toxic toward mammalian cells. In order to reduce the cytotoxic property of the peptide while maintaining its antimicrobial property, the inventors of the present disclosure have replaced at least one lysine residue in the peptide using an epsilon lysine residue and/or a delta-ornithine residue and/or a gamma-2,4-diaminobutyric acid residue and/or a beta-2,3 diaminopropionic acid residue. Without wishing to be bound by theory, such replacement also surprisingly (1) enhances the cell selectivity of an antimicrobial peptide, (2) provides peptides that have good antimicrobial properties and are proteolytic-resistant, (3)

improves therapeutic potential of pore-forming peptides while retaining the efficacy against drug-resistant pathogens, (4) enhances the therapeutic potential of pore forming cytotoxic peptides without compromising the antimicrobial properties. Therefore, the approach (i.e. the replacement of lysine residue in a peptide) also will expand the repertoire of applications of the modified peptides for the design of anticancer, and anti-inflammatory drugs.

Thus, in a one aspect the present disclosure refers to an isolated peptide comprising at least five amino acid residues of which there is: at least one D-epsilon-lysine amino acid residue; and at least one other amino acid residue selected from the group consisting of non-epsilon-lysine, non-delta-ornithine, non-gamma-2,4-diaminobutyric acid, and non-beta-2,3-diaminopropionic acid amino acid residue; wherein the peptide has reduced or no cytotoxicity when compared to an equivalent peptide without the at least one amino acid residue selected from the group consisting of epsilon-lysine, delta-ornithine, gamma-2,4-diaminobutyric acid, and beta-2,3-diaminopropionic acid residue. In some example the peptide may comprise at least five, at least six, at least seven, at least eight, at least nine, at least 10, at least 11, at least 12, at least 13, at least 14, at least 15, at least 16, at least 17, at least 18, at least 19, or at least 20, at least 30, at least 40, at least 50, at least 60, at least 70, at least 80, at least 90 amino acid residues; at least one, at least two, at least three, at least four, at least five, at least six, at least seven, at least eight, at least nine, at least 10 D-epsilon-lysine amino acid residues; and at least one, at least two, at least three, at least four, at least five, at least six, at least seven, at least eight, at least nine, at least 10, at least 11, at least 12, at least 13, at least 14, at least 15, at least 16, at least 17, at least 18, at least 19, or at least 20, at least 30, at least 40, at least 50, at least 60, at least 70, at least 80, at least 90 other amino acid residue selected from the group consisting of non-epsilon-lysine, non-delta-ornithine, non-gamma-2,4-diaminobutyric acid, and non-beta-2,3-diaminopropionic acid amino acid residue; wherein the peptide may has reduced or may has no cytotoxicity when compared to an equivalent peptide without the at least one amino acid residue selected from the group consisting of epsilon-lysine, delta-ornithine, gamma-2,4-diaminobutyric acid, and beta-2,3-diaminopropionic acid residue.

In another aspect the present disclosure refers to an isolated peptide comprising at least five amino acid residues of which there is: at least one L-epsilon-lysine amino acid residue; and at least one other amino acid residue selected from the group consisting of non-epsilon-lysine, non-delta-ornithine, non-gamma-2,4-diaminobutyric acid, and non-beta-2,3-diaminopropionic acid amino acid residue; wherein the peptide has reduced or no cytotoxicity when compared to an equivalent peptide without the at least one amino acid residue selected from the group consisting of epsilon-lysine, delta-ornithine, gamma-2,4-diaminobutyric acid, and beta-2,3-diaminopropionic acid residue. In some example the peptide may comprise at least five, at least six, at least seven, at least eight, at least nine, at least 10, at least 11, at least 12, at least 13, at least 14, at least 15, at least 16, at least 17, at least 18, at least 19, or at least 20, at least 30, at least 40, at least 50, at least 60, at least 70, at least 80, at least 90 amino acid residues; at least one, at least two, at least three, at least four, at least five, at least six, at least seven, at least eight, at least nine, at least 10 L-epsilon-lysine amino acid residues; and at least one, at least two, at least three, at least four, at least five, at least six, at least seven, at least eight, at least nine, at least 10, at least 11, at least 12, at least 13, at least 14, at least 15, at least 16, at least 17, at least 18, at least 19, or at least 20, at least 30, at least 40, at least 50, at least 60, at least 70, at least 80, at least 90 other amino acid residue selected from the group consisting of non-epsilon-lysine, non-delta-ornithine, non-gamma-2,4-diaminobutyric acid, and non-beta-2,3-diaminopropionic acid amino acid residue; wherein the peptide may has reduced or may has no cytotoxicity when compared to an equivalent peptide without the at least one amino acid residue selected from the group consisting of epsilon-lysine, delta-ornithine, gamma-2,4-diaminobutyric acid, and beta-2,3-diaminopropionic acid residue.

In another aspect the present disclosure refers to an isolated peptide comprising at least five amino acid residues of which there is: at least one D-delta-ornithine amino acid residue; and at least one other amino acid residue selected from the group consisting of non-epsilon-lysine, non-delta-ornithine, non-gamma-2,4-diaminobutyric acid, and non-beta-2,3-diaminopropionic acid amino acid residue; wherein the peptide has reduced or no cytotoxicity when compared to an equivalent peptide without the at least one amino acid residue selected from the group consisting of epsilon-lysine, delta-ornithine, gamma-2,4-diaminobutyric acid, and beta-2,3-diaminopropionic acid residue. In some example the peptide may comprise at least five, at least six, at least seven, at least eight, at least nine, at least 10, at least 11, at least 12, at least 13, at least 14, at least 15, at least 16, at least 17, at least 18, at least 19, or at least 20, at least 30, at least 40, at least 50, at least 60, at least 70, at least 80, at least 90 amino acid residues; at least one, at least two, at least three, at least four, at least five, at least six, at least seven, at least eight, at least nine, at least 10 D-delta-ornithine amino acid residues; and at least one, at least two, at least three, at least four, at least five, at least six, at least seven, at least eight, at least nine, at least 10, at least 11, at least 12, at least 13, at least 14, at least 15, at least 16, at least 17, at least 18, at least 19, or at least 20, at least 30, at least 40, at least 50, at least 60, at least 70, at least 80, at least 90 other amino acid residue selected from the group consisting of non-epsilon-lysine, non-delta-ornithine, non-gamma-2,4-diaminobutyric acid, and non-beta-2,3-diaminopropionic acid amino acid residue; wherein the peptide may has reduced or may has no cytotoxicity when compared to an equivalent peptide without the at least one amino acid residue selected from the group consisting of epsilon-lysine, delta-ornithine, gamma-2,4-diaminobutyric acid, and beta-2,3-diaminopropionic acid residue.

In another aspect the present disclosure refers to an isolated peptide comprising at least five amino acid residues of which there is: at least one L-delta-ornithine amino acid residue; and at least one other amino acid residue selected from the group consisting of non-epsilon-lysine, non-delta-ornithine, non-gamma-2,4-diaminobutyric acid, and non-beta-2,3-diaminopropionic acid amino acid residue; wherein the peptide has reduced or no cytotoxicity when compared to an equivalent peptide without the at least one amino acid residue selected from the group consisting of epsilon-lysine, delta-ornithine, gamma-2,4-diaminobutyric acid, and beta-2,3-diaminopropionic acid residue. In some example the peptide may comprise at least five, at least six, at least seven, at least eight, at least nine, at least 10, at least 11, at least 12, at least 13, at least 14, at least 15, at least 16, at least 17, at least 18, at least 19, or at least 20, at least 30, at least 40, at least 50, at least 60, at least 70, at least 80, at least 90 amino acid residues; at least one, at least two, at least three, at least four, at least five, at least six, at least seven, at least eight, at least nine, at least 10 L-delta-ornithine amino acid residues; and at least one, at least two, at least three, at least four, at least five, at least six, at least seven, at least eight, at least nine, at least 10, at least 11, at least 12, at least 13, at least 14, at least 15, at least 16, at least 17, at least 18, at least 19, or at least 20, at least 30, at least 40, at least 50, at least 60, at least 70, at least 80, at least 90 other amino acid residue selected from the group consisting of non-epsilon-lysine, non-delta-ornithine, non-gamma-2,4-diaminobutyric acid, and non-beta-2,3-diaminopropionic acid amino acid residue; wherein the peptide may has reduced or may has no cytotoxicity when compared to an equivalent peptide without the at least one amino acid residue selected from the group consisting of epsilon-lysine, delta-ornithine, gamma-2,4-diaminobutyric acid, and beta-2,3-diaminopropionic acid residue.

In a another aspect the present disclosure refers to an isolated peptide comprising at least five amino acid residues of which there is: at least one D-gamma-2,4-diaminobutyric acid amino acid residue; and at least one other amino acid residue selected from the group consisting of non-epsilon-lysine, non-delta-ornithine, non-gamma-2,4-diaminobutyric acid, and non-beta-2,3-diaminopropionic acid amino acid residue; wherein the peptide has reduced or no cytotoxicity when compared to an equivalent peptide without the at least one amino acid residue selected from the group consisting of epsilon-lysine, delta-ornithine, gamma-2,4-diaminobutyric acid, and beta-2,3-diaminopropionic acid residue. In some example the peptide may comprise at least five, at least six, at least seven, at least eight, at least nine, at least 10, at least 11, at least 12, at least 13, at least 14, at least 15, at least 16, at least 17, at least 18, at least 19, or at least 20, at least 30, at least 40, at least 50, at least 60, at least 70, at least 80, at least 90 amino acid residues; at least one, at least two, at least three, at least four, at least five, at least six, at least seven, at least eight, at least nine, at least 10 D-gamma-2,4-diaminobutyric acid amino acid residues; and at least one, at least two, at least three, at least four, at least five, at least six, at least seven, at least eight, at least nine, at least 10, at least 11, at least 12, at least 13, at least 14, at least 15, at least 16, at least 17, at least 18, at least 19, or at least 20, at least 30, at least 40, at least 50, at least 60, at least 70, at least 80, at least 90 other amino acid residue selected from the group consisting of non-epsilon-lysine, non-delta-ornithine, non-gamma-2,4-diaminobutyric acid, and non-beta-2,3-diaminopropionic acid amino acid residue; wherein the peptide may has reduced or may has no cytotoxicity when compared to an equivalent peptide without the at least one amino acid residue selected from the group consisting of epsilon-lysine, delta-ornithine, gamma-2,4-diaminobutyric acid, and beta-2,3-diaminopropionic acid residue.

In another aspect the present disclosure refers to an isolated peptide comprising at least five amino acid residues of which there is: at least one L-gamma-2,4-diaminobutyric acid amino acid residue; and at least one other amino acid residue selected from the group consisting of non-epsilon-lysine, non-delta-ornithine, non-gamma-2,4-diaminobutyric acid, and non-beta-2,3-diaminopropionic acid amino acid residue; wherein the peptide has reduced or no cytotoxicity when compared to an equivalent peptide without the at least one amino acid residue selected from the group consisting of epsilon-lysine, delta-ornithine, gamma-2,4-diaminobutyric acid, and beta-2,3-diaminopropionic acid residue. In some example the peptide may comprise at least five, at least six, at least seven, at least eight, at least nine, at least 10, at least 11, at least 12, at least 13, at least 14, at least 15, at least 16, at least 17, at least 18, at least 19, or at least 20, at least 30, at least 40, at least 50, at least 60, at least 70, at least 80, at least 90 amino acid residues; at least one, at least two, at least three, at least four, at least five, at least six, at least seven, at least eight, at least nine, at least 10 L-gamma-2,4-diaminobutyric acid amino acid residues; and at least one, at least two, at least three, at least four, at least five, at least six, at least seven, at least eight, at least nine, at least 10, at least 11, at least 12, at least 13, at least 14, at least 15, at least 16, at least 17, at least 18, at least 19, or at least 20, at least 30, at least 40, at least 50, at least 60, at least 70, at least 80, at least 90 other amino acid residue selected from the group consisting of non-epsilon-lysine, non-delta-ornithine, non-gamma-2,4-diaminobutyric acid, and non-beta-2,3-diaminopropionic acid amino acid residue; wherein the peptide may has reduced or may has no cytotoxicity when compared to an equivalent peptide without the at least one amino acid residue selected from the group consisting of epsilon-lysine, delta-ornithine, gamma-2,4-diaminobutyric acid, and beta-2,3-diaminopropionic acid residue.

In another aspect the present disclosure refers to an isolated peptide comprising at least five amino acid residues of which there is: at least one D-beta-2,3-diaminopropionic acid amino acid residue; and at least one other amino acid residue selected from the group consisting of non-epsilon-lysine, non-delta-ornithine, non-gamma-2,4-diaminobutyric acid, and non-beta-2,3-diaminopropionic acid amino acid residue; wherein the peptide has reduced or no cytotoxicity when compared to an equivalent peptide without the at least one amino acid residue selected from the group consisting of epsilon-lysine, delta-ornithine, gamma-2,4-diaminobutyric acid, and beta-2,3-diaminopropionic acid residue. In some example the peptide may comprise at least five, at least six, at least seven, at least eight, at least nine, at least 10, at least 11, at least 12, at least 13, at least 14, at least 15, at least 16, at least 17, at least 18, at least 19, or at least 20, at least 30, at least 40, at least 50, at least 60, at least 70, at least 80, at least 90 amino acid residues; at least one, at least two, at least three, at least four, at least five, at least six, at least seven, at least eight, at least nine, at least 10 D-beta-2,3-diaminopropionic acid amino acid residues; and at least one, at least two, at least three, at least four, at least five, at least six, at least seven, at least eight, at least nine, at least 10, at least 11, at least 12, at least 13, at least 14, at least 15, at least 16, at least 17, at least 18, at least 19, or at least 20, at least 30, at least 40, at least 50, at least 60, at least 70, at least 80, at least 90 other amino acid residue selected from the group consisting of non-epsilon-lysine, non-delta-ornithine, non-gamma-2,4-diaminobutyric acid, and non-beta-2,3-diaminopropionic acid amino acid residue; wherein the peptide may has reduced or may has no cytotoxicity when compared to an equivalent peptide without the at least one amino acid residue selected from the group consisting of epsilon-lysine, delta-ornithine, gamma-2,4-diaminobutyric acid, and beta-2,3-diaminopropionic acid residue.

In another aspect the present disclosure refers to an isolated peptide comprising at least five amino acid residues of which there is: at least one L-beta-2,3-diaminopropionic acid amino acid residue; and at least one other amino acid residue selected from the group consisting of non-epsilon-lysine, non-delta-ornithine, non-gamma-2,4-diaminobutyric acid, and non-beta-2,3-diaminopropionic acid amino acid residue; wherein the peptide has reduced or no cytotoxicity when compared to an equivalent peptide without the at least one amino acid residue selected from the group consisting of epsilon-lysine, delta-ornithine, gamma-2,4-diaminobutyric acid, and beta-2,3-diaminopropionic acid residue. In some example the peptide may comprise at least five, at least six, at least seven, at least eight, at least nine, at least 10, at least 11, at least 12, at least 13, at least 14, at least 15, at least 16, at least 17, at least 18, at least 19, or at least 20, at least 30, at least 40, at least 50, at least 60, at least 70, at least 80, at least 90 amino acid residues; at least one, at least two, at least three, at least four, at least five, at least six, at least seven, at least eight, at least nine, at least 10 L-beta-2,3-diaminopropionic acid amino acid residues; and at least one, at least two, at least three, at least four, at least five, at least six, at least seven, at least eight, at least nine, at least 10, at least 11, at least 12, at least 13, at least 14, at least 15, at least 16, at least 17, at least 18, at least 19, or at least 20, at least 30, at least 40, at least 50, at least 60, at least 70, at least 80, at least 90 other amino acid residue selected from the group consisting of non-epsilon-lysine, non-delta-ornithine, non-gamma-2,4-diaminobutyric acid, and non-beta-2,3-diaminopropionic acid amino acid residue; wherein the peptide may has reduced or may has no cytotoxicity when compared to an equivalent peptide without the at least one amino acid residue selected from the group consisting of epsilon-lysine, delta-ornithine, gamma-2,4-diaminobutyric acid, and beta-2,3-diaminopropionic acid residue.

In another aspect the present disclosure refers to an isolated peptide comprising at least five amino acid residues of which there is: at least one D-epsilon-lysine amino acid residue and/or at least one L-epsilon-lysine amino acid residue and/or at least one D-delta-ornithine amino acid residue and/or at least one L-delta-ornithine amino acid residue and/or at least one D-gamma-2,4-diaminobutyric acid amino acid residue and/or at least one L-gamma-2,4-diaminobutyric acid amino acid residue and/or at least one D-beta-2,3-diaminopropionic acid amino acid residue and/or at least one L-beta-2,3-diaminopropionic acid amino acid residue; and at least one other amino acid residue selected from the group consisting of non-epsilon-lysine, non-delta-ornithine, non-gamma-2,4-diaminobutyric acid, and non-beta-2,3-diaminopropionic acid amino acid residue; wherein the peptide has reduced or no cytotoxicity when compared to an equivalent peptide without the at least one amino acid residue selected from the group consisting of epsilon-lysine, delta-ornithine, gamma-2,4-diaminobutyric acid, and beta-2,3-diaminopropionic acid residue. In some example the peptide may comprise at least five, at least six, at least seven, at least eight, at least nine, at least 10, at least 11, at least 12, at least 13, at least 14, at least 15, at least 16, at least 17, at least 18, at least 19, or at least 20, at least 30, at least 40, at least 50, at least 60, at least 70, at least 80, at least 90 amino acid residues; at least one, at least two, at least three, at least four, at least five, at least six, at least seven, at least eight, at least nine, at least 10 D-epsilon-lysine amino acid residues and/or at least one, at least two, at least three, at least four, at least five, at least six, at least seven, at least eight, at least nine, at least 10 L-epsilon-lysine amino acid residues and/or at least one, at least two, at least three, at least four, at least five, at least six, at least seven, at least eight, at least nine, at least 10 D-delta-ornithine amino acid residues and/or at least one, at least two, at least three, at least four, at least five, at least six, at least seven, at least eight, at least nine, at least 10 L-delta-ornithine amino acid residues and/or at least one, at least two, at least three, at least four, at least five, at least six, at least seven, at least eight, at least nine, at least 10 D-gamma-2,4-diaminobutyric acid amino acid residues and/or at least one, at least two, at least three, at least four, at least five, at least six, at least seven, at least eight, at least nine, at least 10 L-gamma-2,4-diaminobutyric acid amino acid residues and/or at least one, at least two, at least three, at least four, at least five, at least six, at least seven, at least eight, at least nine, at least 10 D-beta-2,3-diaminopropionic acid amino acid residues and/or at least one, at least two, at least three, at least four, at least five, at least six, at least seven, at least eight, at least nine, at least 10 L-beta-2,3-diaminopropionic acid amino acid residues; and at least one, at least two, at least three, at least four, at least five, at least six, at least seven, at least eight, at least nine, at least 10, at least 11, at least 12, at least 13, at least 14, at least 15, at least 16, at least 17, at least 18, at least 19, or at least 20, at least 30, at least 40, at least 50, at least 60, at least 70, at least 80, at least 90 other amino acid residue selected from the group consisting of non-epsilon-lysine, non-delta-ornithine, non-gamma-2,4-diaminobutyric acid, and non-beta-2,3-diaminopropionic acid amino acid residue; wherein the peptide may has reduced or may has no cytotoxicity when compared to an equivalent peptide without the at least one amino acid residue selected from the group consisting of epsilon-lysine, delta-ornithine, gamma-2,4-diaminobutyric acid, and beta-2,3-diaminopropionic acid residue.

In one example, the peptide of the present disclosure has reduced cytotoxicity when compared to an equivalent peptide without the at least one amino acid residue selected from the group consisting of epsilon-lysine, delta-ornithine, gamma-2,4-diaminobutyric acid, and beta-2,3-diaminopropionic acid residue. As shown for example in Tables 4 and 5, the peptide of the present disclosure such as Peptide 3 (SEQ ID NO: 13), Peptide 4 (SEQ ID NO: 14), Peptide 5 (SEQ ID NO: 15), and Peptide 6 (SEQ ID NO: 16) becomes cytotoxic toward human dermal fibroblasts cell (HDF) only at high concentration (Peptide 3 at 250 μg/mL or 87.8 μM and Peptides 4 to 6 at 1000 μg/mL or 351.3 μM). Contrastingly, as shown for example in Table 6, other modified peptides known in the art causes breakdown of hemoglobin or red blood cells (i.e. have haemolytic activity) and becomes cytotoxic even at relatively low concentration. Thus, the inventors of the present disclosure have surprisingly found that the reduction of cytotoxicity in the peptide of the present disclosure is more apparent than the reduction of cytotoxicity in other modified peptides known in the art.

As used herein, the term "D-epsilon-lysine" refers to an amino acid residue having the following structure

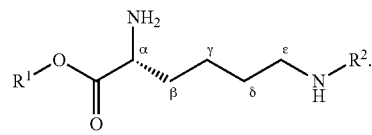

The term "$R^1$" and "$R^2$" on the chemical structure of "D-epsilon-lysine" refers for example to other amino acid residues in a peptide. In one example, when a peptide is said to comprise "D-epsilon-lysine", the epsilon amino group (or the amino group connected to the carbon labeled with "ε") participate in the peptide bond formation.

As used herein, the term "L-epsilon-lysine" refers to an amino acid residue having the following structure:

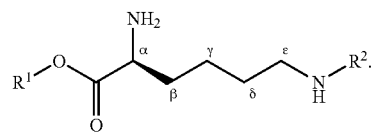

The term "$R^1$" and "$R^2$" on the chemical structure of "L-epsilon-lysine" refers for example to other amino acid residues in a peptide. In one example, when a peptide is said to comprise "L-epsilon-lysine", the epsilon amino group (or the amino group connected to the carbon labeled with "ε") participate in the peptide bond formation.

As used herein, the term "D-delta-ornithine" refers to an amino acid residue having the following structure:

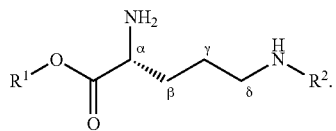

The term "R$^1$" and "R$^2$" on the chemical structure of "D-delta-ornithine" refers for example to other amino acid residues in a peptide. In one example, when a peptide is said to comprise "D-delta-ornithine", the delta amino group (or the amino group connected to the carbon labeled with "δ") participate in the peptide bond formation.

As used herein, the term "L-delta-ornithine" refers to an amino acid residue having the following structure:

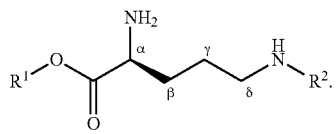

The term "R$^1$" and "R$^2$" on the chemical structure of "L-delta-ornithine" refers for example to other amino acid residues in a peptide. In one example, when a peptide is said to comprise "L-delta-ornithine", the delta amino group (or the amino group connected to the carbon labeled with "δ") participate in the peptide bond formation.

As used herein, the term "D-gamma-2,4-diaminobutyric acid" refers to an amino acid residue having the following structure:

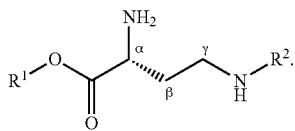

The term "R$^1$" and "R$^2$" on the chemical structure of "D-gamma-2,4-diaminobutyric acid" refers for example to other amino acid residues in a peptide. In one example, when a peptide is said to comprise "D-gamma-2,4-diaminobutyric acid", the gamma amino group (or the amino group connected to the carbon labeled with "γ") participate in the peptide bond formation.

As used herein, the term "L-gamma-2,4-diaminobutyric acid" refers to an amino acid residue having the following structure:

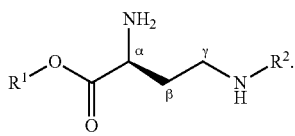

The term "R$^1$" and "R$^2$" on the chemical structure of "L-gamma-2,4-diaminobutyric acid" refers for example to other amino acid residues in a peptide. In one example, when a peptide is said to comprise "L-gamma-2,4-diaminobutyric acid", the gamma amino group (or the amino group connected to the carbon labeled with "γ") participate in the peptide bond formation.

As used herein, the term "D-beta-2,3-diaminopropionic acid" refers to an amino acid residue having the following structure:

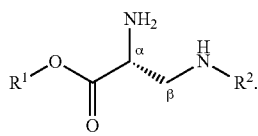

The term "R$^1$" and "R$^2$" on the chemical structure of "D-beta-2,3-diaminopropionic acid" refers for example to other amino acid residues in a peptide. In one example, when a peptide is said to comprise "D-beta-2,3-diaminopropionic acid", the beta amino group (or the amino group connected to the carbon labeled with "β") participate in the peptide bond formation.

As used herein, the term "L-beta-2,3-diaminopropionic acid" refers to an amino acid residue having the following structure:

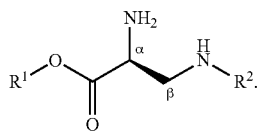

The term "R$^1$" and "R$^2$" on the chemical structure of "L-beta-2,3-diaminopropionic acid" refers for example to other amino acid residues in a peptide. In one example, when a peptide is said to comprise "L-beta-2,3-diaminopropionic acid", the beta amino group (or the amino group connected to the carbon labeled with "β") participate in the peptide bond formation.

As used herein, the term "peptide bond" refers to a chemical bond formed between two molecules when the carboxyl group (such as —COOH) of one molecule reacts with the amino group (such as —NH$_2$) of the other molecule, releasing a molecule of water (H$_2$O). This is a dehydration synthesis reaction (also known as a condensation reaction), and usually occurs between amino acids.

As used herein, the term "isolated" refers to a peptide free of or substantially free of proteins, lipids, nucleic acids, for example, with which the peptide is naturally associated. The term "isolated" is also used herein to refer to polypeptides and proteins that are isolated from other cellular proteins and is meant to encompass both purified and recombinant polypeptides. In other embodiments, the term "isolated" means separated from constituents, cellular and otherwise, in which the cell, tissue, polynucleotide, peptide, polypeptide, protein, antibody or fragment(s) thereof, which are normally associated in nature.

As used herein, the term "antimicrobial peptide" refers to oligo- or polypeptides that kill microorganisms or inhibit their growth. As used herein, the term "anticancer peptide" refers to oligo- or polypeptides that kill cancerous cells or inhibit their proliferation. As used herein, the term "anti-inflammatory peptide" refers to oligo- or polypeptides that prevents or stop inflammation. "Antimicrobial peptides"

may include peptides that result from the cleavage of larger proteins or peptides that are synthesized ribosomally or non-ribosomally. Generally, antimicrobial peptides are cationic molecules with spatially separated hydrophobic and charged regions. Exemplary antimicrobial peptides include linear peptides that form an alpha-helical structure in membranes or peptides that form beta-sheet structures optionally stabilized with disulfide bridges in membranes. Representative antimicrobial peptides include, but are not limited to cathelicidins, defensins, dermcidin, and more specifically magainin 2, protegrin, tachyplesin, protegrin-1, melittin, dermaseptin 01, cecropin, caerin, ovispirin, alamethicin, pandinin 1, pandinin 2, and mastoparans B.

It will be appreciated by person skilled in the art that peptides include peptides from vertebrates and non-vertebrates, including plants, humans, fungi, microbes, and insects. Peptides include those peptides that increase membrane permeability, for example by forming a pore in the membrane. In some example, the peptide is an antimicrobial peptide.

The terms "decrease", "reduce", "reduced", "reduction", "decrease", "removal", or "inhibit" are all used herein generally to mean a decrease by a statistically significant amount. However, for avoidance of doubt, "reduced", "reduce", "reduction", "decrease", "removal", or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level (e.g., in the absence of a peptide as described herein). As used herein, the term "cytotoxicity" is used in its broadest sense and it refers to the quality of being toxic to the cells of a subject who is treated using the peptide of the present disclosure. The criteria of "reduced cytotoxicity" may be based on relative increase in the peptide concentration that confers maximum cytotoxicity to the cells in comparison to the parent peptides. Peptides having reduced cytotoxicity are desired because such peptides can be administered to a subject at a concentration required to inhibit the growth of microorganism or to manage microbial colonization without harming the subject or negatively affecting the cells of the subject. The subject includes, but is not limited to, mammalian (such as human). As shown for example in Table 7 and Example 15, the isolated peptides of the present disclosure is surprisingly less cytotoxic than an equivalent peptide. In one non-limiting example, mastoparan B is cytotoxic at 125 µg/ml whereas exemplary peptides of the present disclosure (such as MB1 (SEQ ID NO: 7) and MB2 (SEQ ID NO: 8)) are cytotoxic at 250 and 1000 µg/ml.

As used herein, the term "equivalent peptide" refers to a peptide having identical amino acid sequence to the peptide of the disclosure, wherein the equivalent peptide does not comprise epsilon-lysine amino acid residue and wherein the peptide of the disclosure comprises epsilon-lysine amino acid residue.

In one example, the isolated peptide is not epsilon-polylysine. As used herein, the term "epsilon-polylysine" refers to a naturally occurring or synthetically produced homopolyamide in which the backbone amide group is formed between α-carboxyl and ε-amino group of the amino acid lysine. In some example, the epsilon-polylysine contains at least four consecutive epsilon-lysine residues.

In one example, the peptide of the present disclosure may comprise lysine residues, wherein with respect to the lysine residues in the peptide, the peptide may comprises epsilon-lysine amino acid residues and alpha-lysine amino acid residues. As shown for example in Table 4, modified melittin such as peptides 1 to 3 of Table 4 (SEQ ID NOs: 11, 12, and 13) each comprises one epsilon lysine residue and two alpha lysine residue. In another example, the peptide of the present disclosure may comprise lysine residues, wherein with respect to the lysine residues in the peptide, the peptide may comprise only epsilon-lysine amino acid residues. As shown for example in Table 4, a modified melittin such as peptide 4 of Table 4 (SEQ ID NOs: 14) comprises three lysine residues that are all epsilon-lysine. As used herein, the term "epsilon-lysine amino acid residues" refers to a lysine residue in a peptide in which the backbone amide group is formed between α-carboxyl and ε-amino group of the amino acid lysine.

In one example, the peptide of the present disclosure may comprise other amino acid residue selected from the group consisting of non-epsilon-lysine, non-delta-ornithine, non-gamma-2,4-diaminobutyric acid, and non-beta-2,3-diaminopropionic acid amino acid residue. In one example, the other amino acid residue selected from the group consisting of non-epsilon-lysine, non-delta-ornithine, non-gamma-2,4-diaminobutyric acid, and non-beta-2,3-diaminopropionic acid amino acid residue may be selected from canonical amino acid residues and non-canonical amino acid residues.

As used herein, the term "canonical amino acid residues" refers to twenty amino acid residues that may be generally incorporated into naturally occurring peptides and proteins and that may be encoded directly by the codons of the universal genetic code, which is common language for almost all organisms to translate nucleotide sequences of deoxyribonucleic acid (DNA) and ribonucleic acid (RNA) to amino acid sequences of proteins. In one example, the "canonical amino acid residues" include, but are not limited to, alanine (A), cysteine (C), aspartic acid (D), glutamic acid (E), phenylalanine (F), glycine (G), histidine (H), isoleucine (I), lysine (K) (such as alpha-lysine (alpha-K)), leucine (L), methionine (M), asparagine (N), proline (P), glutamine (Q), arginine (R), serine (S), threonine (T), valine (V), tryptophan (W), and tyrosine (Y).

As used herein, the term "non-canonical amino acid residue" refers to amino acid residues in D- or L-form that are not among the 20 canonical amino acids generally incorporated into naturally occurring proteins. Non-canonical amino acids include naturally rare (in peptides or proteins) amino acid residues or unnatural amino acid residues. Examples of non-canonical amino acids include, without limitation, β-amino acids, homoamino acids, cyclic amino acids, α-, α-disubstituted amino acids, N-alkyl amino acids, and amino acids with derivatized side chains. Other examples include (in the L-form or D-form): citrulline (Cit), homocitrulline (hCit), N-methylcitrulline (NMeCit), N-methylhomocitrulline (NMeHoCit), ornithine (Orn or O), N-Methylornithine (NMeOrn), sarcosine (Sar), homolysine (hK or Hlys), homoarginine (hR or hArg), homoglutamine (hQ), N-methylarginine (NMeR), N-methylleucine (NMeL), N-methylhomolysine (NMeHoK), N-methylglutamine (NMeQ), norleucine (Nle), norvaline (Nva), 1,2,3,4-tetrahydroisoquinoline (Tic), nitrophenylalanine (nitrophe), aminophenylalanine (aminophe), benzylphenylalanine (benzylphe), γ-carboxyglutamic acid (γ-carboxyglu), hydroxyproline (hydroxypro), p-carboxyl-phenylalanine (Cpa), α-aminoadipic acid (Aad), acetylarginine (acetylarg), α,β-diaminopropionoic acid (Dpr), α,γ-diaminobutyric acid (Dab), diaminopropionic acid (Dap), β-(1-Naphthyl)-alanine (1Na1), β-(2-Naphthyl)-alanine (2Na1), cyclohexylalanine (Cha), 4-methyl-phenylalanine (MePhe), β,β-diphenylalanine (BiPhA), aminobutyric acid (Abu), 4-phenyl-phenylalanine (4Bip), α-amino-isobutyric acid (Aib), beta-alanine, beta-aminopropionic acid, piperidinic acid, aminocaprioic acid, aminoheptanoic acid, aminopimelic acid, desmosine, diaminopimelic acid, N-ethylglycine, N-ethylaspargine, hyroxylysine, allo-hydroxylysine, isodesmosine, allo-isoleucine, N-methylglycine, N-methylisoleucine, N-methylvaline, 4-hydroxyproline, γ-carboxyglutamate, β-N,N,N-trimethyllysine, β-N-acetyllysine, O-phosphoserine, N-acetylserine, N-formylmethionine, 3-methylhistidine, 5-hydroxylysine, ω-methylarginine, and other similar amino acids, and derivatized forms of any of these.

In one example, the peptide of the present disclosure may comprise from 5 to 100 amino acids, or from 5 to 20 amino acids, or from 20 to 30 amino acids, or from 30 to 40 amino acids, or from 40 to 50 amino acids, or from 50 to 60 amino acids, or from 60 to 70 amino acids, or from 70 to 80 amino acids, or from 80 to 90 amino acids, or from 90 to 100 amino acids, or from 5 to 90 amino acids, or from 5 to 80 amino acids, or from 5 to 70 amino acids, or from 5 to 60 amino acids, or from 5 to 50 amino acids, or from 5 to 40 amino acids, or from 10 to 90 amino acids, or from 10 to 80 amino acids, or from 10 to 70 amino acids, or from 10 to 60 amino acids, or from 10 to 50 amino acids, or from 10 to 40 amino acids. In some example, the peptide of the present disclosure may comprise 5, or 6, or 7, or 8, or 9, or 10, or 11, or 12, or 13, or 14, or 15, or 16, or 17, or 18, or 19, or 20, or 21, or 22, or 23, or 24, or 25, or 26, or 27, or 28, or 29, or 30, or 31, or 32, or 33, or 34, or 35, or 36, or 37, or 38, or 39, or 40 amino acids. In some example, the peptide of the present disclosure may comprise from 12 to 37 amino acids. As shown for example in FIG. 21, the peptide of the present disclosure comprises 12 residues. As shown for example in Table 7, the peptide of the present disclosure comprises 14 residues. As shown for example in Table 4, the peptide of the present disclosure comprises 26 residues.

Figure 20:
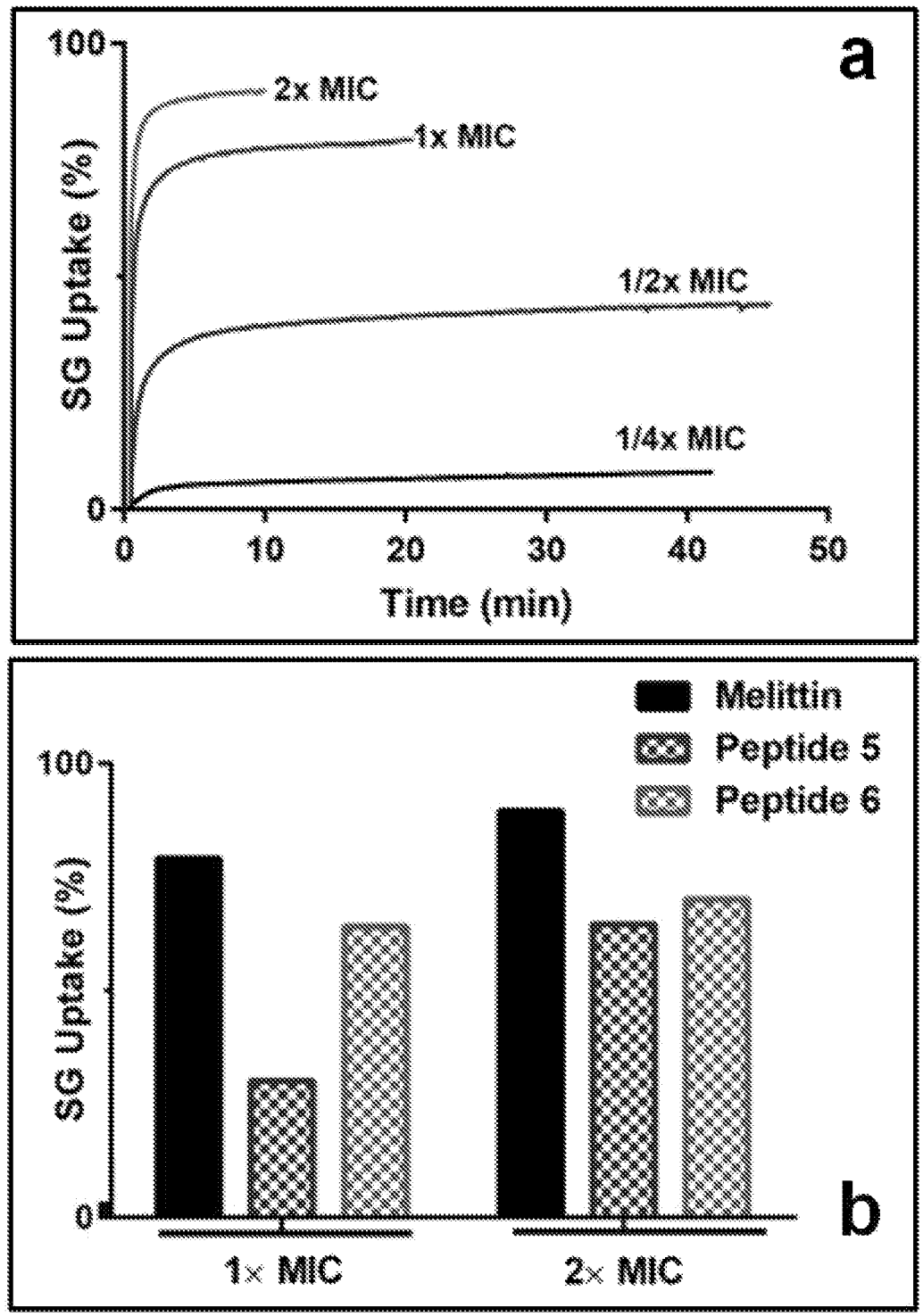
FIG. 20 shows a set data depicting the result of Sytox Green uptake assay.
Figure 20:
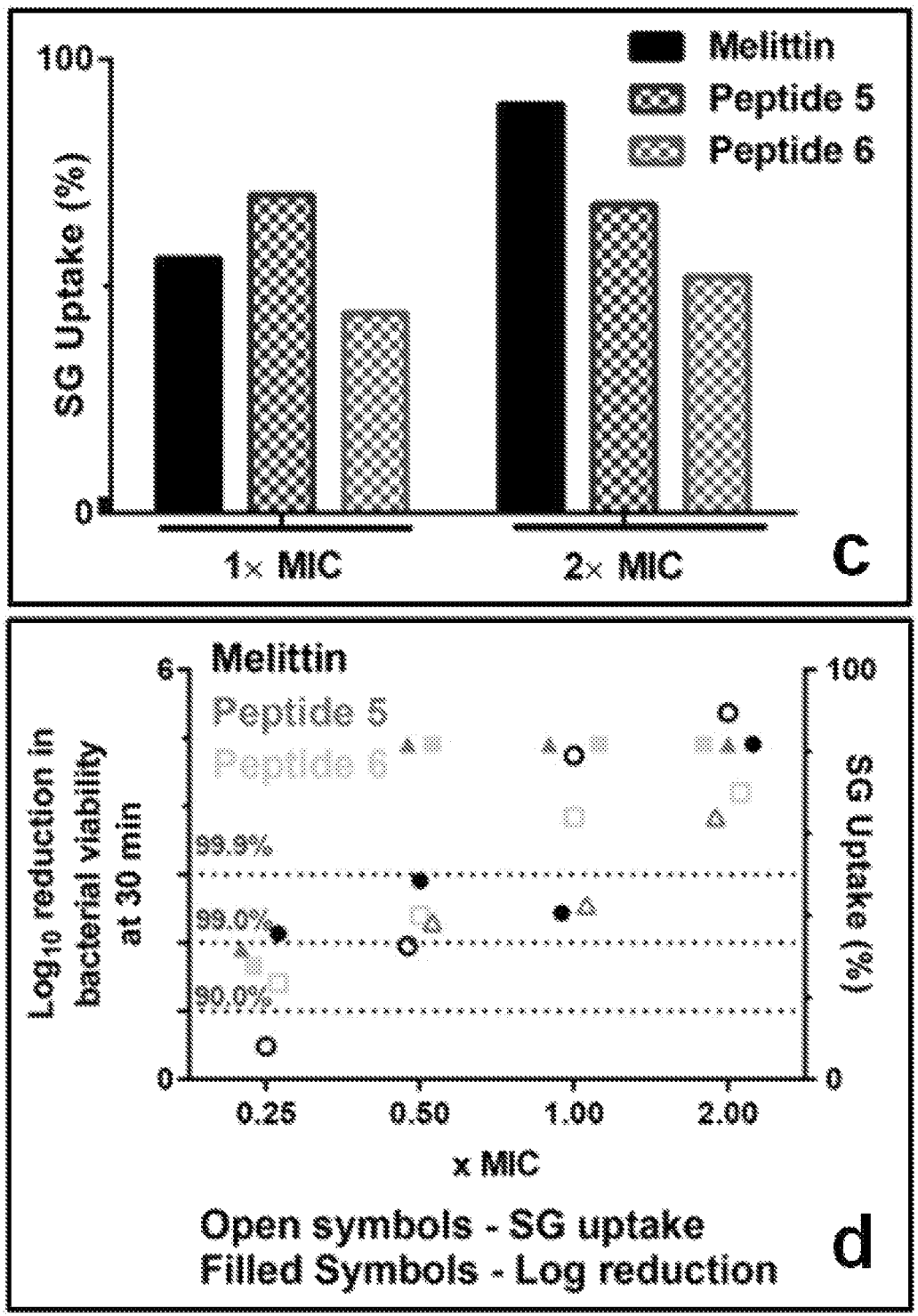

Without wishing to be bound by one theory, it is believed that the peptides provided herein increase membrane permeability of cell by forming a pore in the membrane or by disrupting the membrane. The pore may be formed by one peptide or by several peptides combining to form a multimeric complex. For example, one peptide can produce an alpha-helical structure to form a pore. Alternatively, the peptide can adopt a beta-pleated structure in the membrane and thereby increases membrane permeability. The pore can be of sufficient size to allow small organic molecules or proteins to translocate across the membrane. In one example, the peptide of the present disclosure may be capable of forming pores in a microorganism. Having said the above, as shown for example on FIG. 20, the inventors have also found that even when the epsilon-lysylation affects the poreforming properties of the peptides of the present disclosure, the bactericidal properties of the modified peptides are not affected.

Without wishing to be bound by one theory, the pores in the microorganism may be formed because of the structure of the peptide. For example, an amphipathic α-helical structure may be useful in creating pores. Thus, it is believed that the peptide of the present disclosure may form amphipathic alpha-helical structure. As used herein in reference to an antimicrobial peptide, the term "amphipathic α-helical structure" means an α-helix with a hydrophilic face containing several polar residues at physiological pH and a hydrophobic face containing nonpolar residues. A polar residue can be, for example, a lysine or arginine residue, while a nonpolar residue can be, for example, a leucine or alanine residue. An antimicrobial peptide having an amphipathic α-helical structure generally has an equivalent number of polar and nonpolar residues within the amphipathic domain and a sufficient number of basic residues to give the peptide an overall positive charge at neutral pH.

Figure 21:
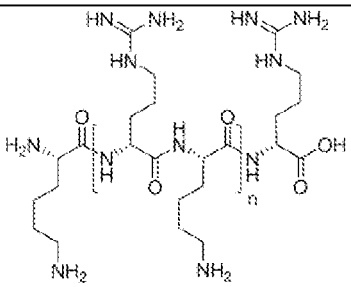
FIG. 21 shows a set of sequences of and graphical representations of the chemical structure of hypercharged peptides (i.e. peptides HC1, HC2, HC4, and HC6).
Figure 21:
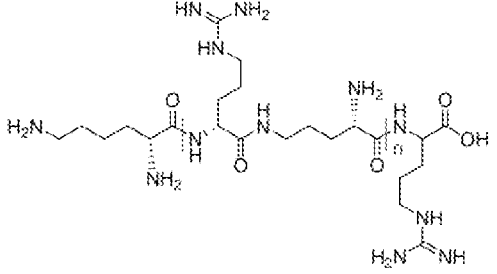
Figure 21:
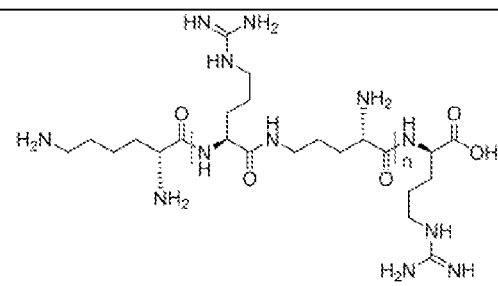
Figure 21:
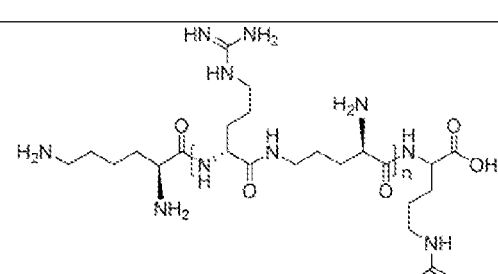

In some examples and as shown for example in FIG. 21, the peptide may comprise 12 amino acid residues (e.g. HC2). In some examples, the peptide may comprise one, or two, or three, or four, or five, or six lysine residues. In some examples, the peptide may comprise six lysine residues, wherein one lysine residue may be an epsilon-lysine residue. In some examples, the peptide may comprise six lysine residues, wherein two lysine residues may be an epsilon-lysine residue. In some examples, the peptide may comprise six lysine residues, wherein three lysine residues may be an epsilon-lysine residue. In some examples, the peptide may comprise six lysine residues, wherein four lysine residues may be an epsilon-lysine residue. In some examples, the peptide may comprise six lysine residues, wherein five lysine residues may be an epsilon-lysine residue. In some examples, the peptide may comprise six lysine residues, wherein six lysine residues may be an epsilon-lysine residue.

In some examples and as shown for example in Table 7, the peptide may comprise 14 amino acid residues (e.g. mastoparans B). In some examples, the peptide may comprise one, or two, or three, or four, or five, or six, or seven lysine residues. In some examples, the peptide may comprise four lysine residues, wherein one lysine residue may be an epsilon-lysine residue. In some examples, the peptide may comprise four lysine residues, wherein two lysine residues may be an epsilon-lysine residue. In some examples, the peptide may comprise four lysine residues, wherein three lysine residues may be an epsilon-lysine residue. In some examples, the peptide may comprise four lysine residues, wherein four lysine residues may be an epsilon-lysine residue.

In some examples and as shown for example in Table 4, the peptide may comprise 26 amino acid residues (e.g. melittin). In some examples, the peptide may comprise one, or two, or three, or four, or five, or six, or seven, or eight, or nine, or 10 lysine residues. In some examples, the peptide may comprise three lysine residues, wherein one lysine residue may be an epsilon-lysine residue. In some examples, the peptide may comprise three lysine residues, wherein two lysine residues may be an epsilon-lysine residue. In some examples, the peptide may comprise three lysine residues, wherein three lysine residues may be an epsilon-lysine residue.

In some examples, the peptide may comprise 23 amino acid residues (e.g. magainin2). In some examples, the peptide may comprise one, or two, or three, or four, or five, or six, or seven, or eight, or nine, or 10 lysine residues. In some examples, the peptide may comprise four lysine residues, wherein one lysine residue may be an epsilon-lysine residue. In some examples, the peptide may comprise four lysine residues, wherein two lysine residues may be an epsilon-lysine residue. In some examples, the peptide may comprise four lysine residues, wherein three lysine residues may be an epsilon-lysine residue. In some examples, the peptide may comprise four lysine residues, wherein four lysine residues may be an epsilon-lysine residue.

In some examples, the peptide may comprise 24 amino acid residues (e.g. pandinin2). In some examples, the peptide may comprise one, or two, or three, or four, or five, or six, or seven, or eight, or nine, or 10 lysine residues. In some examples, the peptide may comprise four lysine residues, wherein one lysine residue may be an epsilon-lysine residue. In some examples, the peptide may comprise four lysine residues, wherein two lysine residues may be an epsilon-lysine residue. In some examples, the peptide may comprise four lysine residues, wherein three lysine residues may be an epsilon-lysine residue. In some examples, the peptide may comprise four lysine residues, wherein four lysine residues may be an epsilon-lysine residue.

In some examples, the peptide may comprise 37 amino acid residues (e.g. cecropin A). In some examples, the peptide may comprise one, or two, or three, or four, or five, or six, or seven, or eight, or nine, or 10 lysine residues. In some examples, the peptide may comprise seven lysine residues, wherein one lysine residue may be an epsilon-lysine residue. In some examples, the peptide may comprise seven lysine residues, wherein two lysine residues may be an epsilon-lysine residue. In some examples, the peptide may comprise seven lysine residues, wherein three lysine residues may be an epsilon-lysine residue. In some examples, the peptide may comprise seven lysine residues, wherein four lysine residues may be an epsilon-lysine residue. In some examples, the peptide may comprise seven lysine residues, wherein five lysine residues may be an epsilon-lysine residue. In some examples, the peptide may comprise seven lysine residues, wherein six lysine residues may be an epsilon-lysine residue. In some examples, the peptide may comprise seven lysine residues, wherein seven lysine residues may be an epsilon-lysine residue.

In some examples and as shown for example in Table 7, the peptide may have the amino acid sequence of LKLKSIVSWAKKVL (SEQ ID NO: 1) (e.g. mastoparan B). In some examples, the peptide may comprise one, or two, or three, or four, or five, or six, or seven lysine residues. In some examples, the peptide may comprise one epsilon-lysine residue; the epsilon-lysine residue may be located at position 2, or at position 4, or at position 11, or at position 12. In some examples, the peptide may comprise two epsilon-lysine residues; the epsilon-lysine residue may be located at positions 2 and 4, or at positions 2 and 11, or at positions 2 and 12, or at positions 4 and 11, or at positions 4 and 12, or at positions 11 and 12. In some examples, the peptide may comprise three epsilon-lysine residues; the epsilon-lysine residue may be located at positions 2, 4, and 11, or at positions 2, 4, and 12, or at positions 2, 11, and 12, or at positions 4, 11, and 12. In some examples, the peptide may comprise four epsilon-lysine residues; the epsilon-lysine residue may be located at positions 2, 4, 11, and 12. In one example such as peptide MB1 in Table 7, the peptide has the amino acid sequence of LKLKSIVSWAKKVL (SEQ ID NO: 1), the peptide comprises one epsilon-lysine residue, and the epsilon-lysine residue is located at position 2 (SEQ ID NO: 7). In one example such as peptide MB2 in Table 7, the peptide has the amino acid sequence of LKLKSIVSWAKKVL (SEQ ID NO: 1), the peptide comprises one epsilon-lysine residue, and the epsilon-lysine residue is located at position 4 (SEQ ID NO: 8). In one example such as peptide MB3 in Table 7, the peptide has the amino acid sequence of LKLKSIVSWAKKVL (SEQ ID NO: 1), the peptide comprises one epsilon-lysine residue, and the epsilon-lysine residue is located at position 11 (SEQ ID NO: 9). In one example such as peptide MB4 in Table 7, the peptide has the amino acid sequence of LKLKSIVSWAKKVL (SEQ ID NO: 1), the peptide comprises one epsilon-lysine residue, and the epsilon-lysine residue is located at position 12 (SEQ ID NO: 10).

In some examples and as shown for example in Table 4, the peptide may have the amino acid sequence of GIGAVLKVLTTGLPALISWIKRKRQQ (SEQ ID NO: 2) (e.g. melittin). In some examples, the peptide may comprise one, or two, or three, or four, or five, or six, or seven or eight, or nine, or 10 lysine residues. In some examples, the peptide may comprise one epsilon-lysine residue; the epsilon-lysine residue may be located at position 7, or at position 21, or at position 23. In some examples, the peptide may comprise two epsilon-lysine residues; the epsilon-lysine residue may be located at positions 7 and 21, or at positions 7 and 23, or at positions 21 and 23. In some examples, the peptide may comprise three epsilon-lysine residues; the epsilon-lysine residue may be located at positions 7, 21, and 23. In one example such as peptide 1 in Table 4, the peptide has the amino acid sequence of GIGAVLKVLTTGLPALISWIKRKRQQ (SEQ ID NO: 2), the peptide comprises one epsilon-lysine residue, and the epsilon-lysine residue is located at position 23 (SEQ ID NO: 11). In one example such as peptide 2 in Table 4, the peptide has the amino acid sequence of GIGAVLKVLTTGLPALISWIKRKRQQ (SEQ ID NO: 2), the peptide comprises one epsilon-lysine residue, and the epsilon-lysine residue is located at position 21 (SEQ ID NO: 12). In one example such as peptide 3 in Table 4, the peptide has the amino acid sequence of GIGAVLKVLTTGLPALISWIKRKRQQ (SEQ ID NO: 2), the peptide comprises one epsilon-lysine residue, and the epsilon-lysine residues are located at position 7 (SEQ ID NO: 13). In one example such as peptide 4 in Table 4, the peptide has the amino acid sequence of GIGAVLKVLTTGLPALISWIKRKRQQ (SEQ ID NO: 2), the peptide comprises three epsilon-lysine residues, and the epsilon-lysine residue is located at positions 7, 21, and 23 (SEQ ID NO: 14). In one example such as peptide 5 in Table 5, the peptide has the amino acid sequence of GIGAVLKVLTTGLPALISWIKRKRQQ (SEQ ID NO: 2), the peptide comprises two epsilon-lysine residues, and the epsilon-lysine residues are located at positions 7 and 21 (SEQ ID NO: 15). In one example such as peptide 5 in Table 5, the peptide has the amino acid sequence of GIGAVLKVLTTGLPALISWIKRKRQQ (SEQ ID NO: 2), the peptide comprises two epsilon-lysine residues, and the epsilon-lysine residues are located at positions 7 and 23 (SEQ ID NO: 16).

In some examples and as shown for example in FIG. 21, the peptide may have the amino acid sequence of KRKRKRKRKRKR (SEQ ID NO: 3) (e.g. HC1). The peptide of SEQ ID NO: 3 can be represented by the following structure:

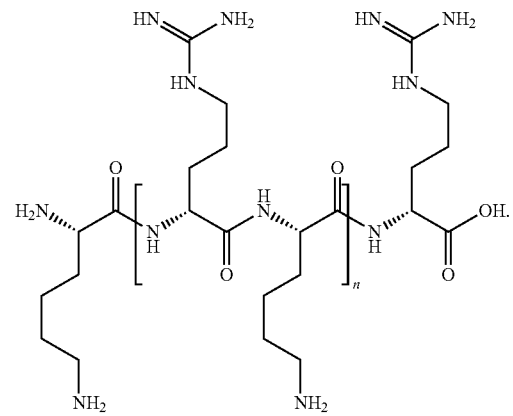

In some examples, the peptide may comprise one, or two, or three, or four, or five, or six, or seven or eight, or nine, or 10 lysine residues. In some examples, the peptide may comprise one epsilon-lysine residue; the epsilon-lysine residue may be located at position 1, or at position 3, or at position 5, or at position 7, or at position 9, or at position 11. In some examples, the peptide may comprise two epsilon-lysine residues; the epsilon-lysine residue may be located at positions 1 and 3, or at positions 1 and 5, or at positions 1 and 7, or at positions 1 and 9, or at positions 1 and 11, or at positions 3 and 5, or at positions 3 and 7, or at positions 3 and 9, or at positions 3 and 11, or at positions 5 and 7, or at positions 5 and 9, or at positions 5 and 11, or at positions 7 and 9, or at positions 7 and 11, or at positions 9 and 11. In some examples, the peptide may comprise three epsilon-lysine residues; the epsilon-lysine residue may be located at positions 1, 3, and 5, or at positions 1, 5, and 7, or at positions 1, 7, and 9, or at positions 1, 9, and 11, or at positions 3, 5, and 7, or at positions 3, 7, and 9, or at positions 3, 9, and 11, or at positions 5, 7, and 9, or at positions 5, 9, and 11, or at positions 7, 9, and 11, or at positions 1, 3, and 7, or at positions 1, 3, and 9, or at positions 1, 3, and 11, or at positions 1, 5, and 9, or at positions 1, 5, and 11, or at positions 1, 7, and 11, or at positions 3, 5, and 9, or at positions 3, 5, and 11, or at positions 3, 7, and 11, or at positions 5, 7, and 11. In some examples, the peptide may comprise four epsilon-lysine residues; the epsilon-lysine residue may be located at positions 1, 3, 5 and 7, or at positions 1, 3, 5 and 9, or at positions 1, 5, 7 and 9, or at positions 1, 7, 9 and 11, or at positions 1, 3, 7 and 9, or at positions 1, 3, 5 and 11, or at positions 1, 3, 7 and 11, or at positions 1, 3, 9 and 11, or at positions 1, 5, 9 and 11, or at positions 1, 5, 7 and 11, or at positions 3, 5, 7 and 11, or at positions 3, 5, 7 and 9, or at positions 3, 7, 9 and 11, or at positions 3, 5, 9 and 11, or at positions 5, 7, 9 and 11. In some examples, the peptide may comprise five epsilon-lysine residues; the epsilon-lysine residue may be located at positions 1, 3, 5, 7, and 9, or at positions 1, 5, 7, 9, and 11, or at positions 1, 3, 5, 7, and 11, or at positions 1, 3, 5, 9, and 11, or at positions 1, 3, 7, 9, and 11, or at positions 3, 5, 7, 9, and 11. In some examples, the peptide may comprise six epsilon-lysine residues; the epsilon-lysine residue may be located at positions 1, 3, 5, 7, 9, and 11. In one example such as peptide HC2 in FIG. 21, the peptide has the amino acid sequence of KRKRKRKRKRKR (SEQ ID NO: 3), the peptide comprises six epsilon-lysine residues, and the epsilon-lysine residues are located at positions 1, 3, 5, 7, 9, and 11 (SEQ ID NO: 17). The peptide of SEQ ID NO: 17 can be represented by the following structure:

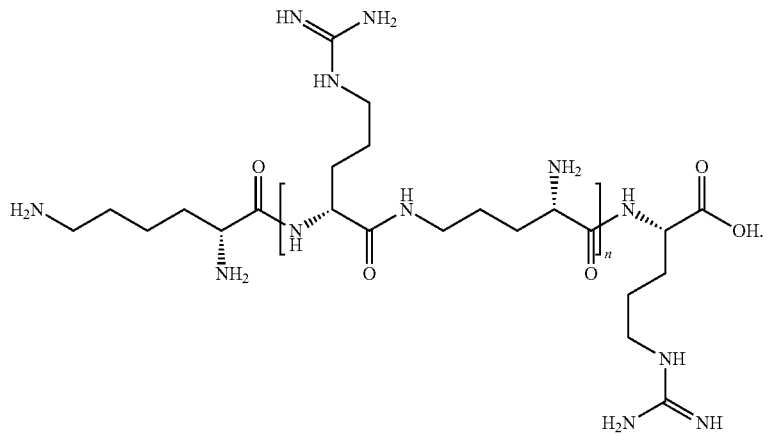

In one example such as peptide HC4 in FIG. 21, the peptide has the amino acid sequence of KrKrKrKrKrKr (SEQ ID NO: 3; wherein "r" represents D-arginyl or D-arginine residue), the peptide comprises six epsilon-lysine residues, and the epsilon-lysine residues are located at positions 1, 3, 5, 7, 9, and 11 (SEQ ID NO: 18). The peptide of SEQ ID NO: 18 can be represented by the following structure:

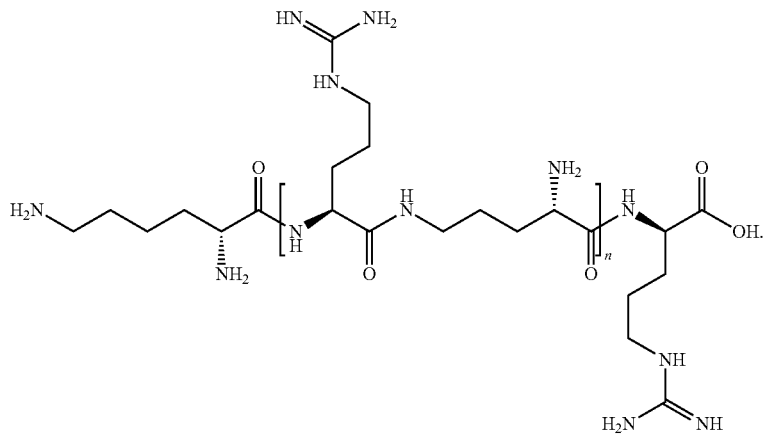

In one example such as peptide HC6 in FIG. 21, the peptide has the amino acid sequence of kRkRkRkRkRkR (SEQ ID NO: 3; wherein "k" represents D-lysyl or D-lysine residue), the peptide comprises six epsilon-lysine residues, and the epsilon-lysine residues are located at positions 1, 3, 5, 7, 9, and 11 (SEQ ID NO: 19). The peptide of SEQ ID NO: 19 can be represented by the following structure:

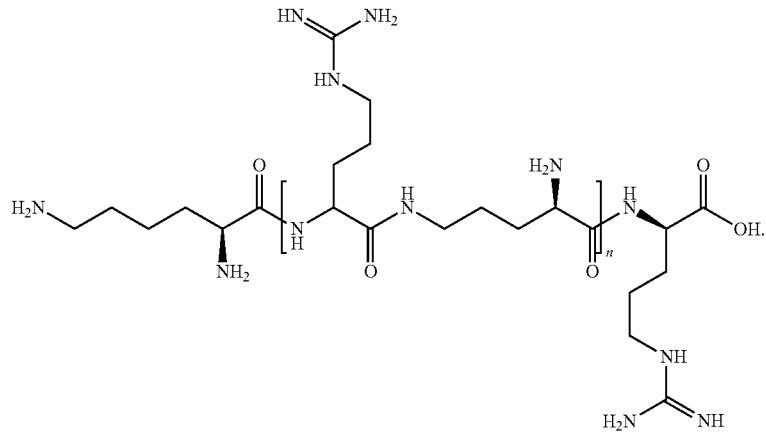

In some examples, the peptide may have the amino acid sequence of GIGKFLHSAKKFGKAFVGEIMNS (SEQ ID NO: 4) (e.g. magainin 2). In some examples, the peptide may comprise one, or two, or three, or four, or five, or six, or seven lysine residues. In some examples, the peptide may comprise one epsilon-lysine residue; the epsilon-lysine residue may be located at position 4, or at position 10, or at position 11, or at position 14. In some examples, the peptide may comprise two epsilon-lysine residues; the epsilon-lysine residue may be located at positions 4 and 10, or at positions 4 and 11, or at positions 4 and 14, or at positions 10 and 11, or at positions 10 and 14, or at positions 11 and 14. In some examples, the peptide may comprise three epsilon-lysine residues; the epsilon-lysine residue may be located at positions 4, 10, and 11, or at positions 4, 11, and 14, or at positions 10, 11, and 14, or at positions 4, 10, and 14. In some examples, the peptide may comprise four epsilon-lysine residues; the epsilon-lysine residue may be located at positions 4, 10, 11, and 14.

In some examples, the peptide may have the amino acid sequence of FWGALAKGALKLIPSLFSSFSKKD (SEQ ID NO: 5) (e.g. pandinin 2). In some examples, the peptide may comprise one, or two, or three, or four, or five, or six, or seven lysine residues. In some examples, the peptide may comprise one epsilon-lysine residue; the epsilon-lysine residue may be located at position 7, or at position 11, or at position 22, or at position 23. In some examples, the peptide may comprise two epsilon-lysine residues; the epsilon-lysine residue may be located at positions 7 and 11, or at positions 7 and 22, or at positions 7 and 23, or at positions 11 and 22, or at positions 11 and 23, or at positions 22 and 23. In some examples, the peptide may comprise three epsilon-lysine residues; the epsilon-lysine residue may be located at positions 7, 11, and 22, or at positions 7, 11, and 23, or at positions 11, 22, and 23, or at positions 7, 22, and 23. In some examples, the peptide may comprise four epsilon-lysine residues; the epsilon-lysine residue may be located at positions 7, 11, 22, and 23.

In some examples, the peptide may have the amino acid sequence of KWKLFKKIEKVGQNIRDGIIKAGPAVA-VVGQATQIAK-NH$_2$ (SEQ ID NO: 6) (e.g. cecropin A). In some examples, the peptide may comprise one, or two, or three, or four, or five, or six, or seven or eight, or nine, or 10 lysine residues. In some examples, the peptide may comprise one epsilon-lysine residue; the epsilon-lysine residue may be located at position 1, or at position 3, or at position 6, or at position 7, or at position 10, or at position 21, or at position 37. In some examples, the peptide may comprise two epsilon-lysine residues; the epsilon-lysine residue may be located at positions 1 and 3, or at positions 1 and 6, or at positions 1 and 7, or at positions 1 and 10, or at positions 1 and 21, or at positions 1 and 37, or at positions 3 and 6, or at positions 3 and 7, or at positions 3 and 10, or at positions 3 and 21, or at positions 3 and 37, or at positions 6 and 7, or at positions 6 and 10, or at positions 6 and 21, or at positions 6 and 37, or at positions 7 and 10, or at positions 7 and 21, or at positions 7 and 37, or at positions 10 and 21, or at positions 10 and 37, or at positions 21 and 37. In some examples, the peptide may comprise three epsilon-lysine residues; the epsilon-lysine residue may be located at positions 1, 3, and 6, or at positions 1, 3, and 7, or at positions 1, 3, and 10, or at positions 1, 3, and 21, or at positions 1, 3, and 37, or at positions 1, 6, and 7, or at positions 1, 6, and 10, or at positions 1, 6, and 21, or at positions 1, 6, and 37, or at positions 1, 7, and 10, or at positions 1, 7, and 21, or at positions 1, 7, and 37, or at positions 1, 10, and 21, or at positions 1, 10, and 37, or at positions 1, 21, and 37, or at positions 3, 6, and 7, or at positions 3, 6, and 10, or at positions 3, 6, and 21, or at positions 3, 6, and 37, or at positions 3, 7, and 10, or at positions 3, 7, and 21, or at positions 3, 7, and 37, or at positions 3, 10, and 21, or at positions 3, 10, and 37, or at positions 3, 21, and 37, or at positions 6, 7, and 10, or at positions 6, 7, and 21, or at positions 6, 7, and 37, or at positions 6, 10, and 21, or at positions 6, 10, and 37, or at positions 6, 21, and 37, or at positions 7, 10, and 21, or at positions 7, 10, and 37, or at positions 7, 21, and 37, or at positions 10, 21, and 37. In some examples, the peptide may comprise four epsilon-lysine residues; the epsilon-lysine residue may be located at positions 1, 3, 6 and 7, or at positions 1, 3, 6 and 10, or at positions 1, 3, 6 and 21, or at positions 1, 3, 6 and 37, or at positions 1, 3, 7 and 10, or at positions 1, 3, 7 and 21, or at positions 1, 3, 7 and 37, or at positions 1, 3, 10 and 21, or at positions 1, 3, 10 and 37, or at positions 1, 3, 21 and 37, or at positions 1, 6, 7 and 10, or at positions 1, 6, 7 and 21, or at positions 1, 6, 7 and 37, or at positions 1, 6, 10 and 21, or at positions 1, 6, 10 and 37, or at positions 1, 6, 21 and 37, or at positions 1, 7, 10 and 21, or at positions 1, 7, 10 and 37, or at positions 1, 7, 21 and 37, or at positions 1, 10, 21 and 37, or at positions 3, 6, 7 and 10, or at positions 3, 6, 7 and 21, or at positions 3, 6, 7 and 37, or at positions 3, 6, 10 and 21, or at positions 3, 6, 10 and 37, or at positions 3, 6, 21 and 37, or at positions 3, 7, 10 and 21, or at positions 3, 7, 10 and 37, or at positions 3, 7, 21 and 37, or at positions 3, 10, 21 and 37, or at positions 6, 7, 10 and 21, or at positions 6, 7, 10 and 37, or at positions 6, 7, 21 and 37, or at positions 6, 10, 21 and 37, or at positions 7, 10, 21 and 37. In some examples, the peptide may comprise five epsilon-lysine residues; the epsilon-lysine residue may be located at positions 1, 3, 6, 7, and 10, or at positions 1, 3, 6, 7, and 21, or at positions 1, 3, 6, 7, and 37, or at positions 1, 3, 6, 10, and 21, or at positions 1, 3, 6, 10, and 37, or at positions 1, 3, 6, 21, and 37, or at positions 1, 3, 7, 10, and 21, or at positions 1, 3, 7, 10, and 37, or at positions 1, 3, 7, 21, and 37, or at positions 1, 3, 10, 21, and 37, or at positions 1, 6, 7, 10, and 21, or at positions 1, 6, 7, 10, and 37, or at positions 1, 6, 7, 21, and 37, or at positions 1, 6, 10, 21, and 37, or at positions 1, 7, 10, 21, and 37, or at positions 3, 6, 7, 10, and 21, or at positions 3, 6, 7, 10, and 37, or at positions 3, 6, 7, 21, and 37, or at positions 3, 6, 10, 21, and 37, or at positions 3, 7, 10, 21, and 37, or at positions 6, 7, 10, 21, and 37. In some examples, the peptide may comprise six epsilon-lysine residues; the epsilon-lysine residue may be located at positions 1, 3, 6, 7, 10, and 21, or at positions 1, 3, 6, 7, 10, and 37, or at positions 1, 3, 6, 7, 21, and 37, or at positions 1, 3, 6, 10, 21, and 37, or at positions 1, 3, 7, 10, 21, and 37, or at positions 1, 6, 7, 10, 21, and 37, or at positions 3, 6, 7, 10, 21, and 37. In some examples, the peptide may comprise seven epsilon-lysine residues; the epsilon-lysine residue may be located at positions 1, 3, 6, 7, 10, 21, and 37.

Figure 6:
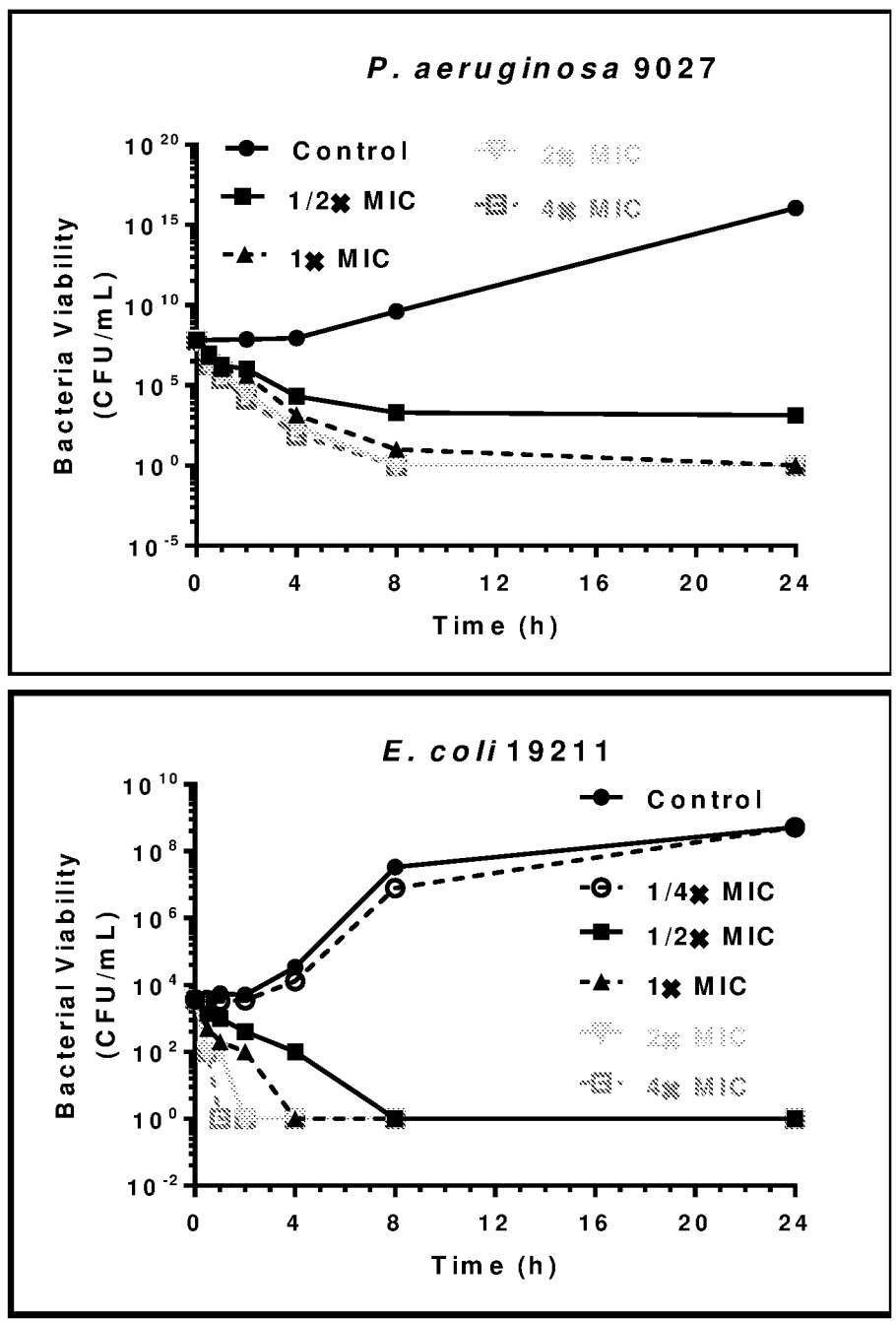
FIG. 6 shows a set of line graphs representing the result of time-kill kinetics experiment of epsilon-polylysine against a panel of Gram-negative and Gram-positive bacteria strains. Thus.
Figure 6:
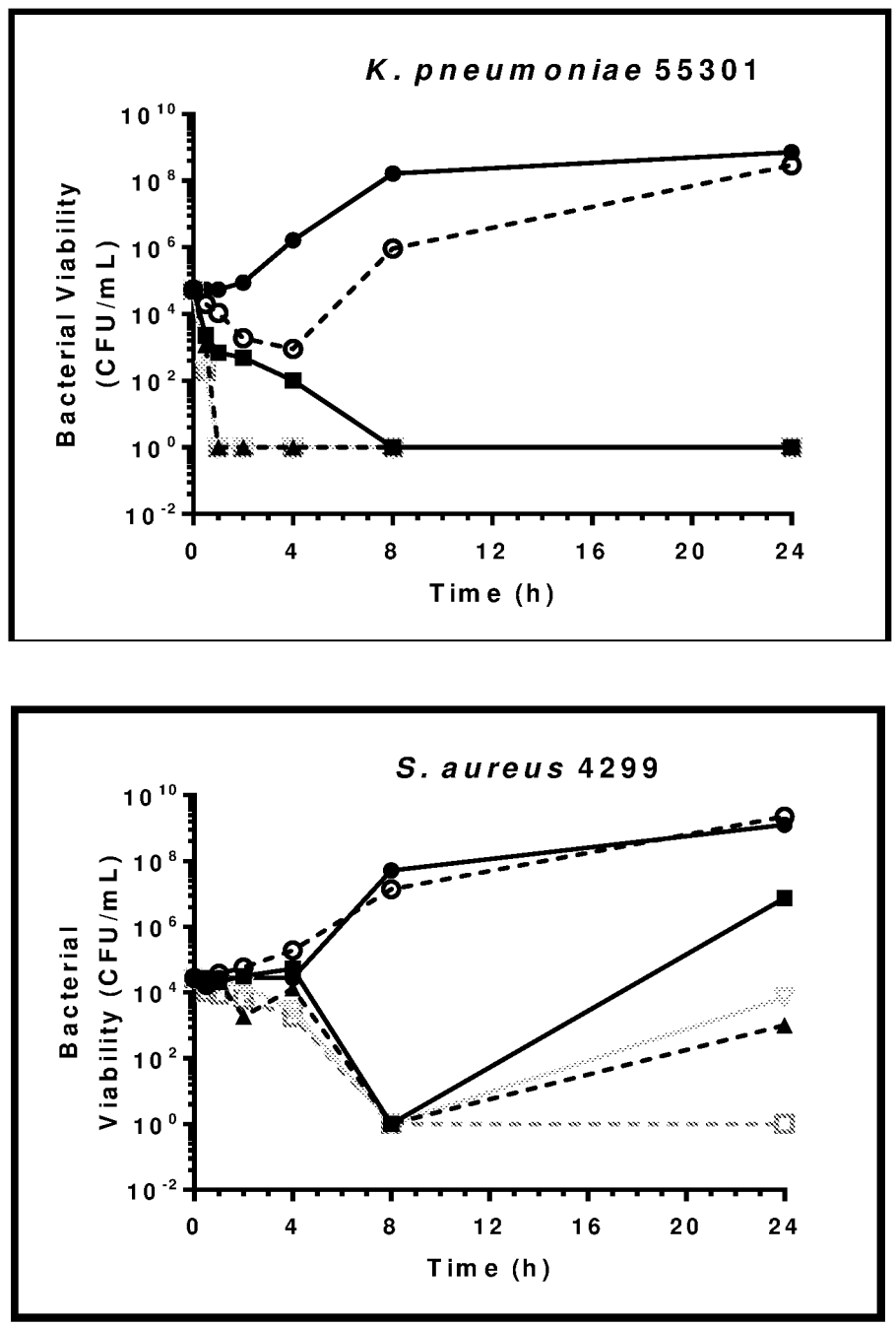
Figure 6:
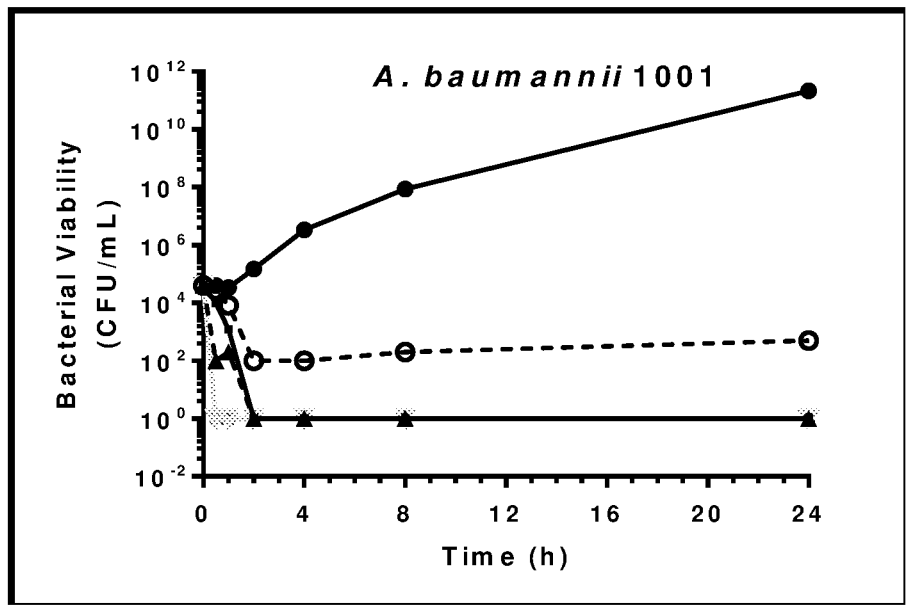
Figure 6:
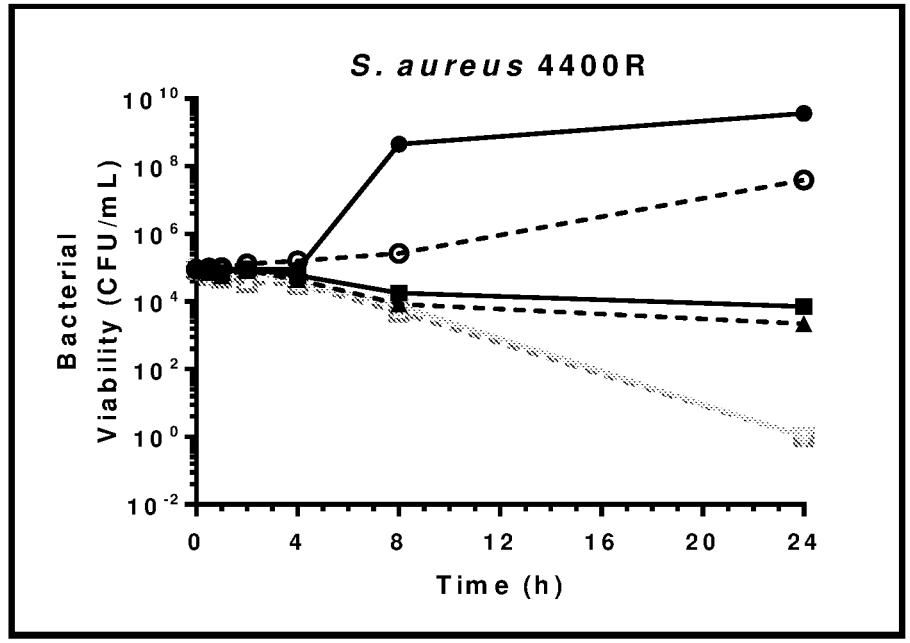
Figure 6:
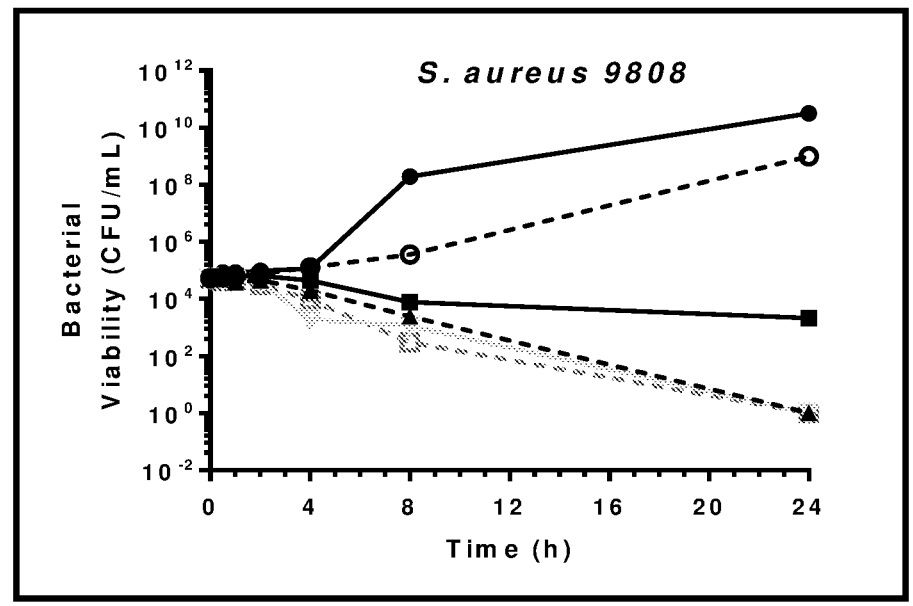
Figure 6:
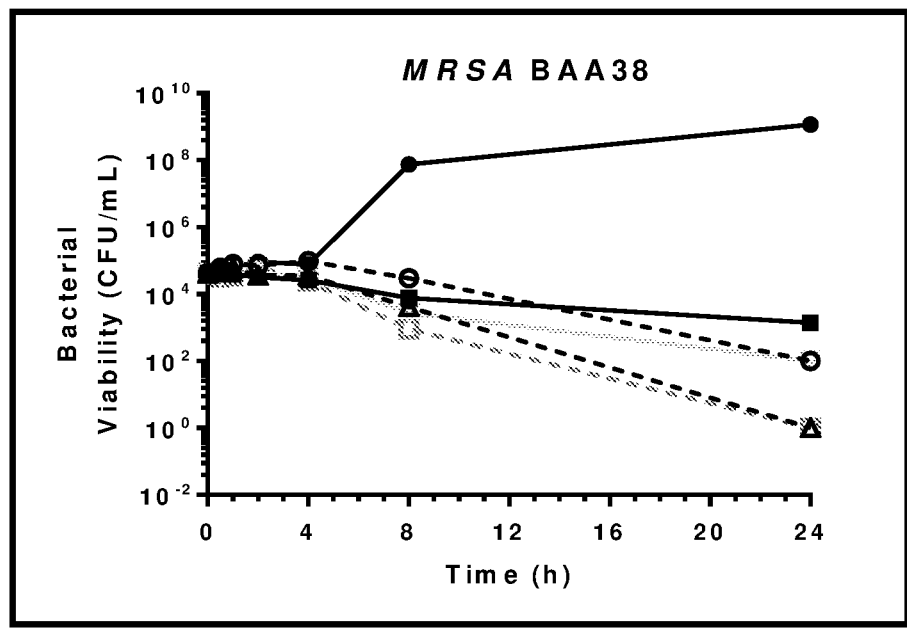

The in vitro antimicrobial efficacy of the peptides of the present disclosure was established by determining the minimum inhibitory concentration (MIC) against wide range of pathogens that include, but are not limited to, methicillin-resistant *Staphylococcus aureus* (MRSA), vancomycin-resistant enterococci (VREs), carbapenam resistant *Enterobacter* (CREs), polymyxin B-resistant *E. cloacae, C. albicans* and *Fusarium* strains. In vivo antimicrobial efficacy is demonstrated in a rabbit model of *Pseudomonas* and *Staphylococcus* keratitis. The disclosure also relates to rational design of peptides with enhanced proteoltyic stability and selectivity for targeting microbial cells over mammalian cells. Thus, as exemplified in the Experimental section (for example in FIG. 6 and FIG. 20), the peptide of the present disclosure may be used to inhibit growth. Therefore, it is also another aspect of the present disclosure to provide the peptide of the present disclosure for use in therapy or medicine. Furthermore, it is also another aspect of the present disclosure to provide a pharmaceutical composition comprising one or more peptide(s) as described herein.

Figure 15:
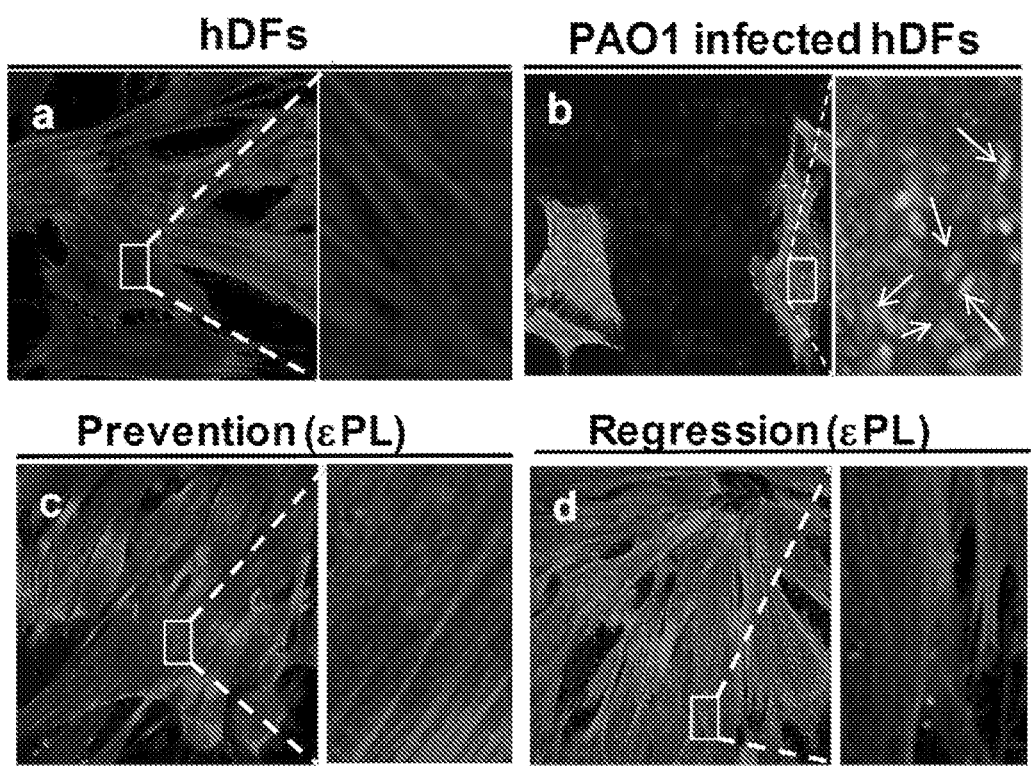
FIG. 15 shows a set of confocal images confirming the ability of epsilon-polylysine in preventing the adverse effects of *P. aeruginosa* infection to host cells.

Another aspect of the present disclosure is to provide a method of inhibiting the growth of a microorganism. In some example and as shown for example in FIG. 15, the method of inhibiting the growth of a microorganism may also treat microbial infection. In some example, the method may comprise administration of a pharmaceutically effective amount of a peptide as described herein and/or a composition as described herein. In some example, the method of inhibiting the growth of a microorganism described herein may inhibit the growth of a microorganism by treating a microbial infection.

As used herein, the terms "treat," "treatment," and grammatical variants thereof, refer to both therapeutic treatment and prophylactic or preventative measures, wherein the object is to prevent or slow down (lessen) an undesired physiological condition, disorder or disease or obtain beneficial or desired clinical results. Such beneficial or desired clinical results include, but are not limited to, alleviation of symptoms; diminishment of extent of condition, disorder or disease; stabilized (i.e. not worsening) state of condition, disorder or disease; delay or slowing of condition, disorder or disease progression; amelioration of the condition, disorder or disease state, remission (whether partial or total), whether detectable or undetectable; or enhancement or improvement of condition, disorder or disease. Treatment includes eliciting a cellular response that is clinically significant, without excessive levels of side effects. Treatment also includes prolonging survival as compared to expected survival if not receiving treatment.

As used herein, the term "microbes" or "microorganism" is used in its broadest sense and is therefore not limited in scope to prokaryotic organisms. Rather, the term "microorganism" includes within its scope bacteria, archaea, yeast, fungi, protozoa and algae. In one example, there is provided a method of treating a microbial infection or removing microorganism comprising administration of a pharmaceutically effective amount of a peptide of the present disclosure. In one example, the microorganism includes, but is not limited to, bacteria or fungi. Thus, in one example, microbial infection includes, but is not limited to, bacterial infection or fungal infection.

In one example, the bacteria may be gram positive bacteria or gram negative bacteria. As used herein, the term "gram positive bacteria" may refer to bacteria which retain the color of the crystal violet stain in the Gram stain. The bacteria may have a cell wall composed of a thick layer of peptidologlycan. As used herein, the term "gram negative bacteria" may refer to bacteria which may not retain the color of the crystal violet stain in the Gram stain. The bacteria may have a cell wall composed of a thin layer of peptidologlycan.

Thus, bacterial infections that may be treated include, but not limited to, those caused by bacteria from the genus of *Acetobacter, Acinetobacter, Actinomyces, Agrobacterium* spp., *Azorhizobium, Azotobacter, Anaplasma* spp., *Bacillus* spp., *Bacteroides* spp., *Bartonella* spp., *Bordetella* spp., *Borrelia, Brucella* spp., *Burkholderia* spp., *Calymmatobacterium, Campylobacter, Chlamydia* spp., *Chlamydophila* spp., *Clostridium* spp., *Corynebacterium* spp., *Coxiella, Ehrlichia, Enterobacter, Enterococcus* spp., *Escherichia, Francisella, Fusobacterium, Gardnerella, Haemophilus* spp., *Helicobacter, Klebsiella, Lactobacillus* spp., *Lactococcus, Legionella, Listeria, Methanobacterium extroquens, Microbacterium multiforme, Micrococcus luteus, Moraxella catarrhalis, Mycobacterium* spp., *Mycoplasma* spp., *Neisseria* spp., *Pasteurella* spp., *Peptostreptococcus, Porphyromonas, Pseudomonas, Rhizobium, Rickettsia* spp., *Rochalimaea, Rothia, Salmonella* spp., *Serratia, Shigella, Staphylococcus* spp., *Stenotrophomonas, Streptococcus* spp., *Treponema* spp., *Vibrio* spp., *Wolbachia,* and *Yersinia* spp. In one example, the bacteria include, but are not limited to, *Acetobacter aurantius, Acinetobacter baumannii, Actinomyces Israelii, Agrobacterium radiobacter, Agrobacterium tumefaciens, Azorhizobium caulinodans, Azotobacter vinelandii, Anaplasma phagocytophilum, Anaplasma marginale, Bacillus anthracis, Bacillus brevis, Bacillus cereus, Bacillus fusiformis, Bacillus licheniformis, Bacillus megaterium, Bacillus mycoides, Bacillus stearothermophilus,*

*Bacillus subtilis, Bacteroides fragilis, Bacteroides gingivalis, Bacteroides melaminogenicus* (*Prevotella melaminogenica*), *Bartonella henselae, Bartonella quintana, Bordetella bronchiseptica, Bordetella pertussis, Borrelia burgdorferi, Brucella abortus, Brucella melitensis, Brucella suis, Burkholderia mallei, Burkholderia pseudomallei, Burkholderia cepacia* complex, *Burkholderia cenocepacia, Calymmatobacterium granulomatis, Campylobacter coli, Campylobacter fetus, Campylobacter jejuni, Campylobacter pylori, Chlamydia trachomatis, Chlamydophila.* (such as *C. pneumoniae, Chlamydophila psittaci, Clostridium botulinum, Clostridium difficile, Clostridium perfringens, Clostridium tetani*), *Corynebacterium diphtheriae, Corynebacterium fusiforme, Coxiella burnetii, Ehrlichia chajfeensis, Enterobacter cloacae, Enterococcus avium, Enterococcus durans, Enterococcus faecalis, Enterococcus faecium, Enterococcus galllinarum, Enterococcus maloratus, Escherichia coli, Francisella tularensis, Fusobacterium nucleatum, Gardnerella vaginalis, Haemophilus ducreyi, Haemophilus influenzae, Haemophilus parainjluenzae, Haemophilus pertussis, Haemophilus vaginalis, Helicobacter pylori, Klebsiella pneumoniae, Lactobacillus acidophilus, Lactobacillus casei, Lactococcus lactis, Legionella pneumophila, Listeria monocytogenes, Methanobacterium extroquens, Microbacterium multiforme, Micrococcus luteus, Moraxella catarrhalis, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycoplasma fermentans, Mycoplasma genitalium, Mycoplasma hominis, Mycoplasma penetrans, Mycoplasma pneumoniae, Neisseria gonorrhoeae, Neisseria meningitidis, Pasteurella multocida, Pasteurella tularensis Peptostreptococcus, Porphyromonas gingivalis, Pseudomonas aeruginosa, Rhizobium Radiobacter, Rickettsia prowazekii, Rickettsia psittaci, Rickettsia quintana, Rickettsia rickettsia, Rickettsia trachomae, Rochalimaea henselae, Rochalimaea quintana, Rothia dentocariosa, Salmonella enteritidis, Salmonella typhi, Salmonella typhimurium, Serratia marcescens, Shigella dysenteriae, Staphylococcus aureus, Staphylococcus epidermidis, Stenotrophomonas maltophilia, Streptococcus agalactiae, Streptococcus, avium, Streptococcus bovis, Streptococcus cricetus, Streptococcus faceium, Streptococcus faecalis, Streptococcus fetus, Streptococcus gallinarum, Streptococcus lactis, Streptococcus mitior, Streptococcus mitis, Streptococcus mutans, Streptococcus oxalis, Streptococcus pneumoniae, Streptococcus pyogenes, Streptococcus rattus, Streptococcus salivarius, Streptococcus sanguis, Streptococcus sobrinus, Treponema pallidum, Treponema denticola, Vibrio cholerae, Vibrio comma, Vibrio parahaemolyticus, Vibrio vulnificus, Wolbachia, Yersinia enterocolitica, Yersinia pestis* and *Yersinia pseudotuberculosis*. In one example, the bacteria includes, but is not limited to, the genus of *Acinetobacter, Bacillus* spp., *Enterobacter, Enterococcus* spp., *Escherichia, Klebsiella, Pseudomonas*, and *Staphylococcus* spp. In one example and as shown for example in Table 5 and Table 7, the bacteria include, but are not limited to *Acinetobacter baumannii, Enterobacter cloacae, Escherichia coli, Klebsiella pneumoniae, Pseudomonas aeruginosa, Staphylococcus aureus*, MRSA, *Enterococcus faecalis* and *Enterococcus faecium.*

Figure 9:
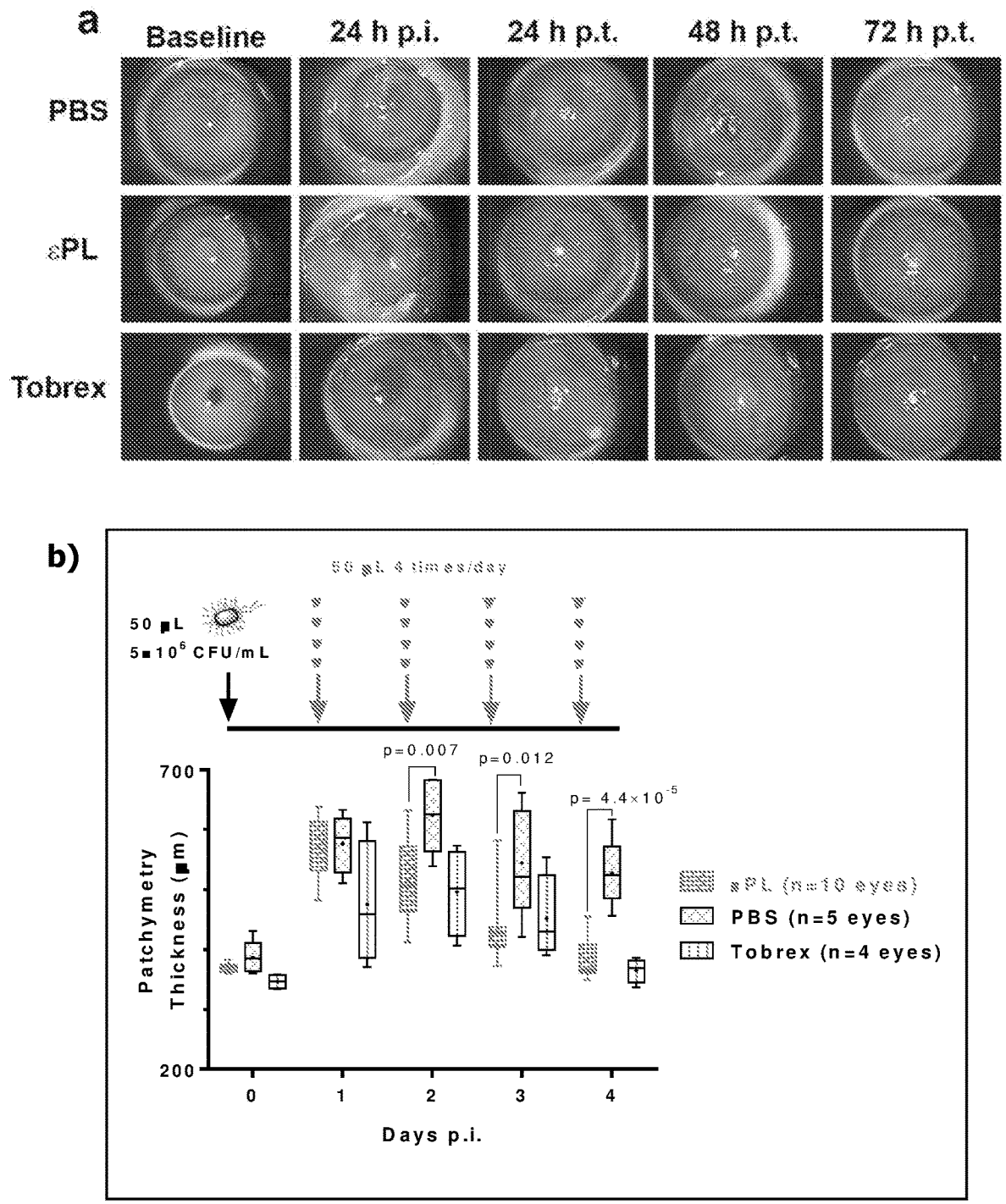
FIG. 9 shows comparison of epsilon-polylysine and zymar treatment on rabbit cornea infected with *Pseudomonas* keratitis. *P. aeruginosa* ATCC 9027 strain.
Figure 9:
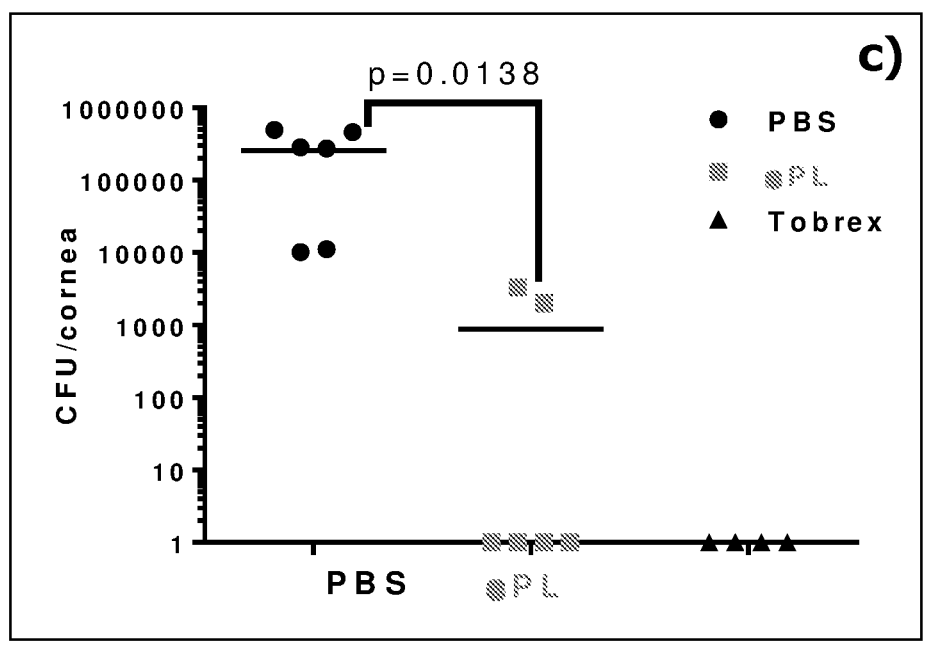

In one example, the bacterial infection may cause conditions such as, but are not limited to pneumonia, tuberculosis, meningitis, diarrhoeal diseases, formation of biofilm, sepsis, listeriosis, gastroenteritis, toxic shock syndrome, hemorrhagic colitis; hemolytic uremic-syndrome, Lyme Disease, gastric and duodenal ulcers, human ehrlichiosis, pseudomembranous colitis, cholera, salmonellosis, cat scratch fever, necrotizing fasciitis (GAS), streptococcal toxic shock syndrome, nosocomial and community associated infections, atherosclerosis, sudden infant death syndrome (SIDS), ear infections, respiratory tract infections, urinary tract infections, skin and soft tissue infections, nail bed infections, wound infection, septicemia, gastrointestinal disease, hospital-acquired endocarditis and blood stream infections. In one example, the bacterial infection may cause conditions such as, but are not limited to Blepharitis, Hordeolum, Preseptal Cellulitis, Dacryocystitis, Orbital Cellulitis, Erysipelas, Vernal Keratoconjunctivitis, Bacterial Conjunctivitis, Conjunctival Laceration, Superior Limbic Keratoconjunctivitis, Conjunctivitis with Pseudomembrane, Epidemic Keratoconjunctivitis, Bacterial Keratitis, Corneal Ulceration, Phlyctenulosis, Anterior Uveitis, Endophthalmitis, Bacterial Abscess, Acute Spetic Retinitis, Chronic Bacterial Retinitis, Papillitis, Optic Neuritis, and Orbital Cellulitis. In one example and as shown for example in FIG. 7 and FIG. 9, the bacterial infection causes conditions such as, but are not limited to *Staphylococcus aureus* keratitis, and *Pseudomonas aeruginosa* keratitis.

In one example, the bacteria may be drug resistant bacteria. In one example and as shown for example in Table 5 and Table 7, the drug resistant bacteria include, but is not limited to, carbapenam-resistant *Enterobacter* strains (CRE), Methicillin-resistant *Staphylococcus aureus* (MRSA), Vancomycin-resistant Enterococci (VRE), polymixin B-resistant *Enterobacter cloacae*, drug-resistant *Acinetobacter baumannii*, and prolific biofilm forming *P. aeruginosa* and *S. epidermidis* strains. Thus, as used herein, the term "drug resistant bacteria" refers to bacteria which may have the ability to grow in a chemical (drug) that generally may kill or limit the growth of the bacteria.

In one example, fungal infections that may be treated include, but not limited to, those caused by fungi from the genus of *Absidia, Ajellomyces, Arthroderma, Aspergillus, Blastomyces, Candida, Cladophialophora, Coccidioides, Cryptococcus, Cunninghamella, Epidermophyton, Exophiala, Filobasidiella, Fonsecaea, Fusarium, Geotrichum, Histoplasma, Hortaea, Issatschenkia, Madurella, Malassezia, Microsporum, Microsporidia, Mucor, Nectria, Paecilomyces, Paracoccidioides, Penicillium, Pichia, Pneumocystis, Pseudallescheria, Rhizopus, Rhodotorula, Scedosporium, Schizophyllum, Sporothrix, Trichophyton*, and *Trichosporon*. In one example, the fungi includes, but is not limited to, *Absidia corymbifera, Ajellomyces capsulatus, Ajellomyces dermatitidis, Arthroderma benhamiae, Arthroderma fulvum, Arthroderma gypseum, Arthroderma incurvatum, Arthroderma otae, Arthroderma vanbreuseghemii, Aspergillus flavus, Aspergillus fumigatus, Aspergillus niger, Blastomyces dermatitidis, Candida albicans, Candida glabrata, Candida guilliermondii, Candida krusei, Candida parapsilosis, Candida tropicalis, Candida pelliculosa, Cladophialophora carrionii, Coccidioides immitis, Coccidioides posadasii, Cryptococcus neoformans, Cunninghamella* Sp, *Epidermophyton floccosum, Exophiala dermatitidis, Filobasidiella neoformans, Fonsecaea pedrosoi, Fusarium solani, Geotrichum candidum, Histoplasma capsulatum, Hortaea werneckii, Issatschenkia orientalis, Madurella grisae, Malassezia furfur, Malassezia globosa, Malassezia obtusa, Malassezia pachydermatis, Malassezia restricta, Malassezia sloofiae, Malassezia sympodialis, Microsporum canis, Microsporum fulvum, Microsporum gypseum, Microsporidia, Mucor circinelloides, Nectria hae-*

*matococca, Paecilomyces variotii, Paracoccidioides brasiliensis, Penicillium marneffei, Pichia anomala, Pichia guilliermondii, Pneumocystis jiroveci, Pneumocystis carinii, Pseudallescheria boydii, Rhizopus oryzae, Rhodotorula rubra, Scedosporium apiospermum, Schizophyllum commune, Sporothnx schenckii, Trichophyton mentagrophytes, Trichophyton rubrum, Trichophyton verrucosum, Trichophyton violaceum, Trichosporon asahii, Trichosporon cutaneum, Trichosporon inkin* and *Trichosporon mucoides*. In one example, the fungi include, but are not limited to, the genus of *Candida, Fusarium*, and *Aspergillus*. In one example and as shown for example in Table 5 and Table 7, the fungi include, but are not limited to, *Candida albicans, Candida parpsilosis, Candica tropicalis, Fusarium solani, Fusarium oxysporum*, and *Aspergillus fumigatus*.

In one example, the fungal infection may cause conditions such as, but are not limited to Ringworm, Fungal Conjuctivitis, Keratomycosis, Uveitis, Abscess, *Candida* Retinitis, Fungal Papillitis and Optic Neuritis, Invasive Aspergillosis, Mucormycosis, Fungal keratitis, *Candida* keratitis, and *Fusarium* keratitis.

In one example, the fungi may be drug resistant fungi. In one example, the drug resistant fungi include, but are not limited to, *Fusarium solani, Fusarium oxysporum*, and *Aspergillus fumigatus*. Thus, as used herein, the term "drug resistant fungi" refers to fungi which may have the ability to grow in a chemical (drug) that generally may kill or limit the growth of the fungi.

In another aspect, there is provided a method of improving the therapeutic index (safety) of an isolated peptide, the peptide comprising at least five amino acid residues, comprising at least one amino acid residue selected from the group consisting of D-epsilon-lysine, L-epsilon-lysine, D-delta-ornithine, L-delta-ornithine, D-gamma-2,4-diaminobutyric acid, L-gamma-2,4-diaminobutyric acid, D-beta-2,3-diaminopropionic acid, and L-beta-2,3-diaminopropionic acid amino acid residue and at least one other selected from the group consisting of non-epsilon-lysine, non-delta-ornithine, non-gamma-2,4-diaminobutyric acid, and non-beta-2,3-diaminopropionic acid amino acid residue, and wherein the peptide has reduced cytotoxicity when compared to equivalent peptide without the at least one selected from the group consisting of epsilon-lysine, delta-ornithine, gamma-2,4-diaminobutyric acid, and beta-2,3-diaminopropionic acid residue, the method comprising modifying at least one of the lysine residues to at least one selected from the group consisting of epsilon-lysine, delta-ornithine, gamma-2,4-diaminobutyric acid, and beta-2,3-diaminopropionic acid residue. As shown for example in FIG. 11, the replacement of alpha-lysine residues in mellitin with epsilon-lysine residues may reduces the cytotoxicity of melittin and thereby increasing its therapeutic index or safety.

In another aspect, there is provided a method of treating proliferative disease comprising administration of a pharmaceutically effective amount of a peptide as described herein and/or a composition as described herein. In one example, the proliferative disease includes, but is not limited to cancer and tumor. As shown for example in FIG. 22, the peptide of the present disclosure reduces the viability of various T-cell and B-cell lymphoma cell lines.

Thus, as used herein, the term "cancer" refers to diseases in which abnormal cells divide without control and can invade nearby tissues. Cancer cells can also spread to other parts of the body through the blood and lymph systems. Main types of cancer include but are not limited to carcinoma, sarcoma, leukemia, lymphoma, multiple myeloma, and central nervous system cancers. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue, such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord. As used herein, the term "tumor" refers to a new growth of tissue in which cell multiplication is uncontrolled and progressive. The growth of tumorous tissue is faster than that of normal tissue, continues after cessation of the stimuli that evoked the growth, and serves no useful physiologic purpose. Tumors may be benign (not cancer), or malignant (cancer).

In another example, the proliferative diseases include but is not limited to colorectal cancer, fibrosarcoma, myxosarcoma, liposarcoma, chondrosarcoma, osteogenic sarcoma, chordoma, angiosarcoma, endotheliosarcoma, lymphangiosarcoma, lymphangio-endotheliosarcoma, synovioma, mesothelioma, Ewing's tumour, leiomyosarcoma, rhabdomyosarcoma, colon carcinoma, gastric cancer, pancreatic cancer, breast cancer, ovarian cancer, prostate cancer, squamous cell carcinoma of the head and neck, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, liver metastases, bile duct carcinoma, choriocarcinoma, seminoma, embryonal carcinoma, thyroid carcinoma such as anaplastic thyroid cancer, Wilms' tumour, cervical cancer, testicular tumour, lung cancer, small cell cancer of the lung, non-small cell cancer of the lung, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, T-Cell lymphoma and B-Cell lymphoma.

Figure 16:
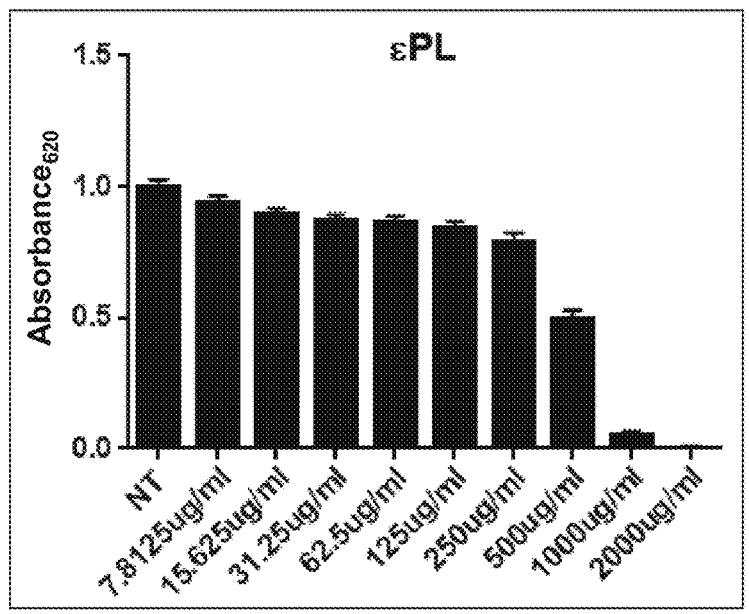
FIG. 16 shows a bar graph depicting anti-inflammatory properties of epsilon-polylysine. Epsilon-polylysine concentration-dependent attenuation of NF-κB activation by lipopolysaccharide (LPS) in THP-1 cells. Note a substantial decrease in NF-κB activation at concentrations above 1 mg/ml. Thus.

As shown for example in FIG. 16, the peptides of the present disclosure substantially inhibit the lippopolysaccharide induced inflammation of the cells. Thus, in another aspect, there is provided a method of treating inflammation comprising administration of a pharmaceutically effective amount of a peptide as described herein and/or a composition as described herein. In one example, the inflammation includes, but is not limited to Acne, neuroinflammation, atherosclerosis, endotoxemic shock, corneal inflammation, and conjunctival inflammation.

As used herein, the term "minimal inhibitory concentration" (MIC) refers to the lowest concentration of an antimicrobial agent (e.g., a peptide as described herein) required to prevent growth or otherwise modify a function of a microorganism under certain conditions, for example in liquid broth medium, and can be determined for a number of different microorganisms according to standard techniques well known in the art.

As used herein, the term "therapeutic index" refers to the ratio of minimum concentration of the peptides that caused complete loss of cellular metabolic activity or complete cytotoxicity over minimal inhibitory concentration (MIC) of a peptide described herein. The loss of cellular metabolic activity or cytotoxicity can be determined using any method known in the art. In one example, the loss of cellular metabolic activity or cytotoxicity can be determined by MTS cell proliferation assay.

As used herein, the term "minimum inhibitory concentration" refers to the minimum concentration of the peptides and/or polymers required for the complete inhibition of bacteria, yeast or fungal growth.

As used herein, the term "proteolytic stability" stability refers to the ability of the peptides to withstand enzyme-mediated processing. Typical enzymes include, but are not limited to, trypsin, chymotrypsin, and pepsin.

In another aspect, there is provided a method of managing microbial colonization comprising administration of an agent comprising one or more peptide(s) as described herein and/or a composition as described herein. In one example, the agent includes, but is not limited to, disinfectant, preservation agent, antiseptic agent, and biocides. In one example, the disinfectant includes, but is not limited to, clinical (hospital) disinfectant, home disinfectant, multipurpose disinfectants, and biocides for advanced wound dressings.

As used herein, the term "disinfectant" refers to agent that may sterilize or maintain microbe-free products. Essentially, any product where microbial growth is undesirable, such as substances which come into contact with animals and humans, can be treated with peptides provided herein to prevent microbial growth. Such products can include, for example, baby wipes, diapers, bandaids, towelettes, make-up products, surgical wares, wound dressings, eyewash and contact lens solutions. As used herein the term "preservation agent" or "preservatives" or "antiseptic" refers to peptide disclosed herein that may be added to products including but are not limited to food, beverages, pharmaceutical drugs, paints, biological samples, cosmetics, and wood to prevent decomposition by microbial growth or by undesirable chemical changes.

Figure 18:
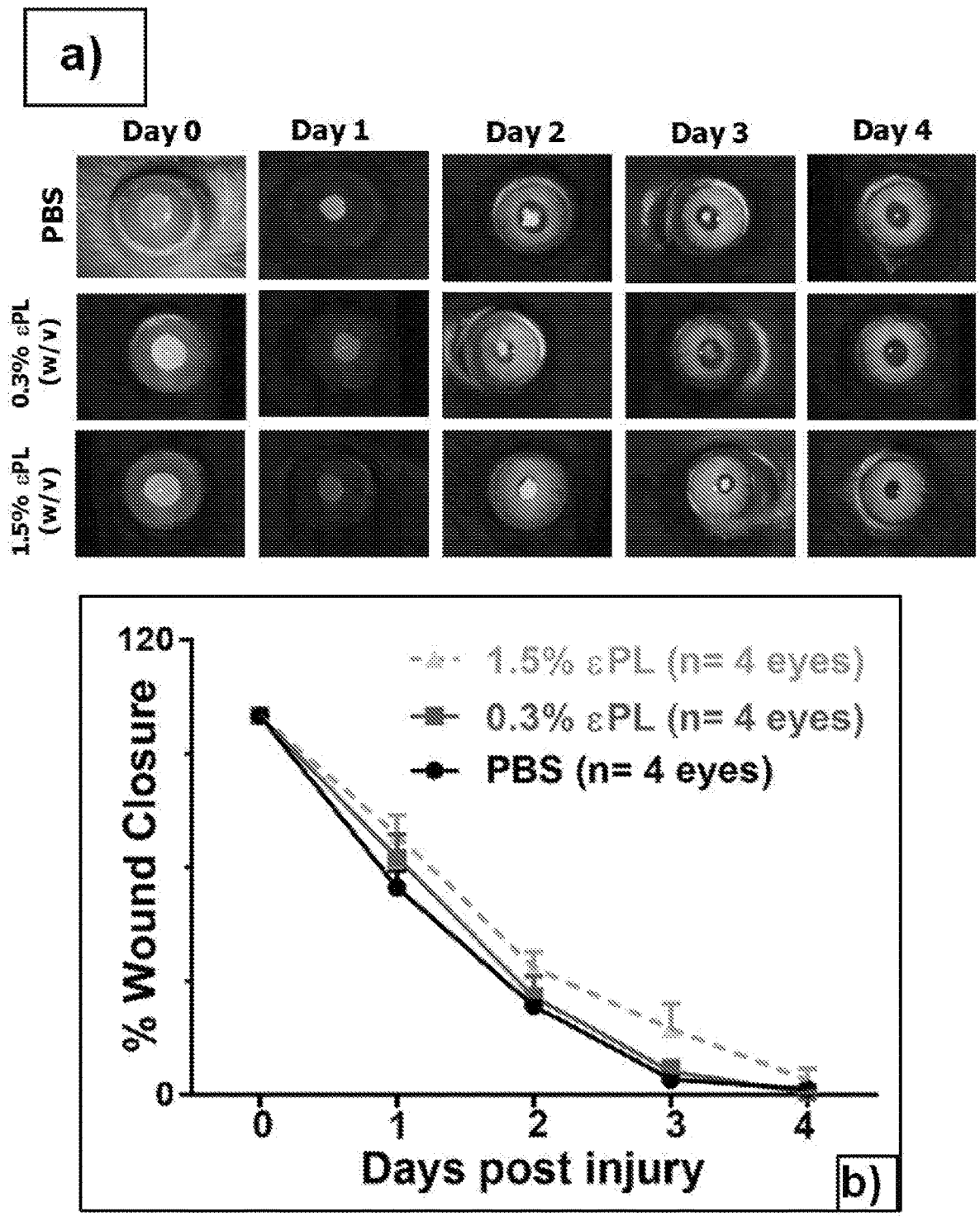
FIG. 18 shows effect of epsilon-polylysine solution (0.3% and 1.5%) on rabbit corneal wound closure after injury.

As shown for example in FIG. 18, the peptide of the present disclosure does not impair wound closure of injured cornea and thus the peptide of the present disclosure is biocompatible and suitable for ophthalmic preparation. Additionally, the current disclosure relates to certain compositions comprising cationic antimicrobial polymer as a broad spectrum ophthalmic eye drop formulations against Gram-positive, Gram-negative and fungal infections. The current disclosure also relates to the use of the peptide of the present disclosure as potent broad spectrum ophthalmic antibiotics for combating infections caused by P. aeruginosa, S. aureus and F. solani. The disclosure also relates to the rational design of peptides with enhanced proteolytic stability and high therapeutic index based on the structure of the polymer and their applications in the management of microbial colonization including but not limited to infectious diseases, multipurpose disinfectant solution, preservatives and antiseptic agents. Thus, in another aspect, there is provided an ophthalmic preparation comprising one or more peptide(s) as described herein and/or a composition as described herein. As used herein, "ophthalmic preparation" can be included in a form of an ophthalmic solution, an ophthalmic suspension, an ophthalmic gel, an ophthalmic ointment or an ophthalmic strip/insert. The ophthalmic solution is an aqueous or organic solution formulated to use as eye drops. The ophthalmic suspension is the addition of a small particle, e.g., microtine nano-particles, which contains the peptide, into an aqueous or organic solution. The ophthalmic gel is a special polymer that disperses in the tear film and forms an essentially transparent film across the ocular surface. The ophthalmic ointment is a mixture of a petrolatum base with wool fat. The ophthalmic strip/insert refers to a filter paper or insoluble contact lens-like object which can be impregnated with the peptide. The impregnated ophthalmic strip/insert can then be place onto the ocular surface or inserted into the lower cul-de-sac. In some examples the ophthalmic preparation described herein includes, but is not limited to, an ophthalmic solution, an eye drop, a lens care solution, multipurpose preservative, ophthalmic tissue preservatives, antiseptics for advanced wound dressings, and coating material for medical devices and surfaces.

Without wishing to be bound by one theory, the peptide of the present disclosure may be synthesized using any methods known in the art. The synthesis of the peptide of the present disclosure may be via Fmoc chemistry or via solid phase peptide synthesis.

In another aspect, there is provided a kit comprising one or more peptide(s) as described herein and/or a composition as described herein.

As used in this application, the singular form "a," "an," and "the" include plural references unless the context clearly dictates otherwise. For example, the term "an isolated peptide" includes a plurality of isolated peptides, including mixtures and combinations thereof.

As used herein, the terms "increase" and "decrease" refer to the relative alteration of a chosen trait or characteristic in a subset of a population in comparison to the same trait or characteristic as present in the whole population. An increase thus indicates a change on a positive scale, whereas a decrease indicates a change on a negative scale. The term "change", as used herein, also refers to the difference between a chosen trait or characteristic of an isolated population subset in comparison to the same trait or characteristic in the population as a whole. However, this term is without valuation of the difference seen.

As used herein, the term "about" in the context of certain stated values means+/−5% of the stated value, or +/−4% of the stated value, or +/−3% of the stated value, or +/−2% of the stated value, or +/−1% of the stated value, or +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Materials and Methods
Minimum Inhibitory Concentration (MIC) Determination.
MIC of cationic polymers and polypeptide were tested in accordance with the Clinical and Laboratory Standards Institute (CLSI) guidelines against a panel of antibiotic-susceptible/-resistant bacteria, yeasts and fungal strains. Bacterial and yeast strains were cultured on tryptic soy agar (TSA) and Sabaroud dextrose agar (SDA) plates (Neogen Corporation, MI, USA) overnight respectively. Inocula in Mueller-Hinton broth (MHB) for bacteria and SD broth for *C. albicans* (Beckton Dickinson, MD, USA) were prepared at 0.5 McFarland. The suspensions were then diluted to a final concentration of $10^5$ CFU/ml in a 96-well microtitre plate (SPL Life Sciences Co., Ltd, Korea). Polymers and polypeptides were added to the inoculum in 2-fold serial dilutions to give a range of concentrations from 2-1024 µg/ml. MIC of the polymers and polypeptides was determined after 24 h incubation at 35° C. by measuring the $OD_{600}$ using a TECAN Infinite M200 microplate reader (Tecan, Austria) as well as by visual observation. The antimicrobial activities were compared with topical antiseptic agents, BAK and CHX. A similar protocol was used to determine the MIC of εPL against antibiotic-resistant pathogens. MIC of the polymers and polypeptides against *Fusarium* strains was determined in full strength RPMI-1640 buffer. Fungal spores were recovered from a 5-day old culture on a potato dextrose agar and diluted to a concentration of $10^5$ spores/ml in 0.9% saline solution. A further 50-fold dilution was done in RPMI-1640 buffer and 100 µl of the inoculum was added to 96 well plates containing an equal volume of test peptides at 2-fold serial dilutions. 200 µl of inoculum without any additives and buffer alone served as positive and negative controls, respectively. The plate was then incubated at 30° C. for 48 h. The absorbance value was measured at 600 nm as before and the lowest concentration of the peptide which inhibited 90% growth was reported. All MIC determinations were performed in duplicates.

Cytocompatibility Assessment of Polymers and Polypeptides.
MTS ((3-(4,5-dimethylthiazol-2-yl)-5-(3-carboxymethoxyphenyl)-2-(4-sulfophenyl)-2H-tetrazolium)) assay and high content analysis (HCA) were performed to elucidate the effect of various polymers on metabolic activity and morphological parameters of cultured human dermal fibroblasts (hDF), respectively as described previously. The antineoplastic agent, nocodazole (5 µg/ml), served as the negative control whereas cells treated with PBS served as positive control. The average values from three independent triplicate experiments are reported. Cells were cultured in 96-well plates and scanned (16 randomly selected fields/well) using an automated microscope IN Cell Analyzer 2200 (GE Healthcare). The multi-parametric cytotoxicity bio-application module of the IN Cell Investigator software (GE Healthcare) was used in quantitative estimations and morphotypic analysis of acquired images, which were automatically converted into color-coded heatmaps using Spotrfire® software.

In Vivo Biocompatibility of εPL in a Rabbit Model of Corneal Epithelial Wound Healing.
All the animals used in this study were treated in accordance to the tenets of the Association for Research in Vision and Ophthalmology (ARVO) statement and the protocol was approved by SingHealth Institutional Animal Care and Use Committee (IACUC; AALAC accredited, Protocol #2012/SHS/775 for wound healing #2014/SHS/1010 for bacterial keratitis studies). Eight New Zealand white rabbits, aged 5 months (body weight 3-3.5 kg) were used for the study and divided into two groups. Prior to wound all the rabbit eyes were examined by slit-lamp photography for the absence of corneal aberrations such as vascularization or any other ocular surface defects. A 6-mm diameter circular region of the corneal surface was de-epithelialized with a sterile mini blade (BD Beaver, MA, USA) after anesthetizing the rabbits. The two groups of rabbits received 50 µl topical instillation of 0.3% εPL (w/v in PBS, pH 7.0) or PBS at 4 times a day until complete wound closure was observed. The corneal epithelial wound healing was visualized by the addition of a drop of 2% w/v sodium fluorescein (Bausch & Lomb) which revealed the epithelial defects upon illumination with a cobalt blue filter and photographed immediately after wounding as well as at 1, 2, 3, and 4 days after post injury. The area of the epithelial defects was then estimated by using Image J software.

In Vivo Efficacy of εPL in *P. aeruginosa* and *S. aureus* Models of Infectious Keratitis.
New Zealand white rabbits, weighing 2-2.5 kg were used for this study. The rabbits were anaesthetized and the corneal surface was de-epithelialized with sterile mini blade (BD Beaver, MA, USA). Corneal infection was induced by applying 50 µl of $5\times10^6$ CFU/ml *S. aureus* ATCC 29213 or *P. aeruginosa* ATCC 9027 strains to the scarified cornea. After 24 h post infection, 50 µL of the 0.3% εPL (w/v in PBS, pH 7.0) or PBS were applied topically to the infected eyes at 4 times/day. Tobrex® eye drops (Alcon, Belgium), which contain 0.3% tobramycin, served as the positive control for *P. aeruginosa* keratitis whereas Zymar® (Allergan, USA) eye drops was used as a positive control for *S. aureus* keratitis. Slit-lamp photographs and anterior segment-optical coherence tomography (AS-OCT) scans were taken before and after infection as well as during the course of the treatment. The pre-inoculation and post-inoculation corneal thickness (CT) was measured perpendicular to the anterior corneal surfaces and the average CT was reported.

Quantification of Viable Bacteria.
3 days after treatment with εPL or ophthalmic antibiotics eye drops or PBS, the rabbit corneas were removed by trephination and homogenized individually in sterile PBS using plastic pestles followed by finer homogenization with bead beating using sterile 2 mm diameter glass beads. Bacterial enumeration was carried out by spreading the homogenate ($10^1$-$10^2$ serial dilution) on TSA plates and incubated for 48 h at 37° C.

Result

Example 1: Antimicrobial Properties and Cytotoxicity of Alpha- (αPL) and Epsilon-Poly-L-Lysines (εPL)

εPL and poly-gamma-L-diaminobutanoic acid (γPAB) were the only naturally occurring and microbially produced cationic aminoacid homopolymers reported so far. Unlike alpha-poly(L-lysine) (PLL), εPL consisted of 25-35 L-lysine residues which are connected by α-carboxyl and ε-amino groups of the monomers, respectively (FIGS. 1A and B). εPL had been shown to display broad spectrum antimicrobial activity against Gram+, Gram−, yeasts and fungal pathogens and the activity was superior to γPAB. εPL was classified as the "generally regarded as safe" (GRAS) by the US FDA and used as food preservative in the US, Korea and Japan. However, the antimicrobial properties of this versatile US FDA approved polymer had not been explored in great details against drug-resistant pathogens. In view of the similar chemical composition, the minimum inhibitory concentrations (MICs) of αPL and εPL against 5 different strains of Gram-positive (*Staphylococcus aureus*), Gram-negative (*Pseudomonas aeruginosa*) and Yeasts (*C. albicans* strains, Table 1) was determined. As shown in FIG. 1, grand mean MIC (GM-MIC) of both the polymers was similar against Gram-positive and Gram-negative strains whereas εPL displayed lower MIC than αPL against *C. albicans* strains.

TABLE 1

Minimum inhibitory concentration of αPL and εPL against a panel of bacteria and yeasts strains

| | MIC in mg/ml of | |
| --- | --- | --- |
| Strains | αPL | εPL |
| *P. aeruginosa* ATCC 9027 | 64 | 32 |
| *P. aeruginosa* ATCC 27853 | 32 | 16 |
| *P. aeruginosa* M023376 | 32 | 32 |
| *P. aeruginosa* DM023257 | 32 | 16 |
| *P. aeruginosa* DM023155 | 64 | 64 |
| *S. aureus* ATCC 29213 | 16 | 16 |
| *S. aureus* ATCC29737 | 16 | 32 |
| *S. aureus* DM4001R | 32 | 16 |
| *S. aureus* DM4400R | 32 | 32 |
| *S. aureus* DM 4299 | 16 | 16 |
| *C. albicans* ATCC 10231 | 256 | 128 |
| *C. albicans* ATCC 24433 | 256 | 128 |
| *C. albicans* ATCC 2091 | 256 | 128 |
| *C. albicans* DF2672R | 256 | 128 |
| *C. albicans* DF 1976R | 256 | 64 |

Example 2: Cytotoxicity of αPL and εPL Assessed by MTT and High Content Analysis (HCA)

Figure 2:
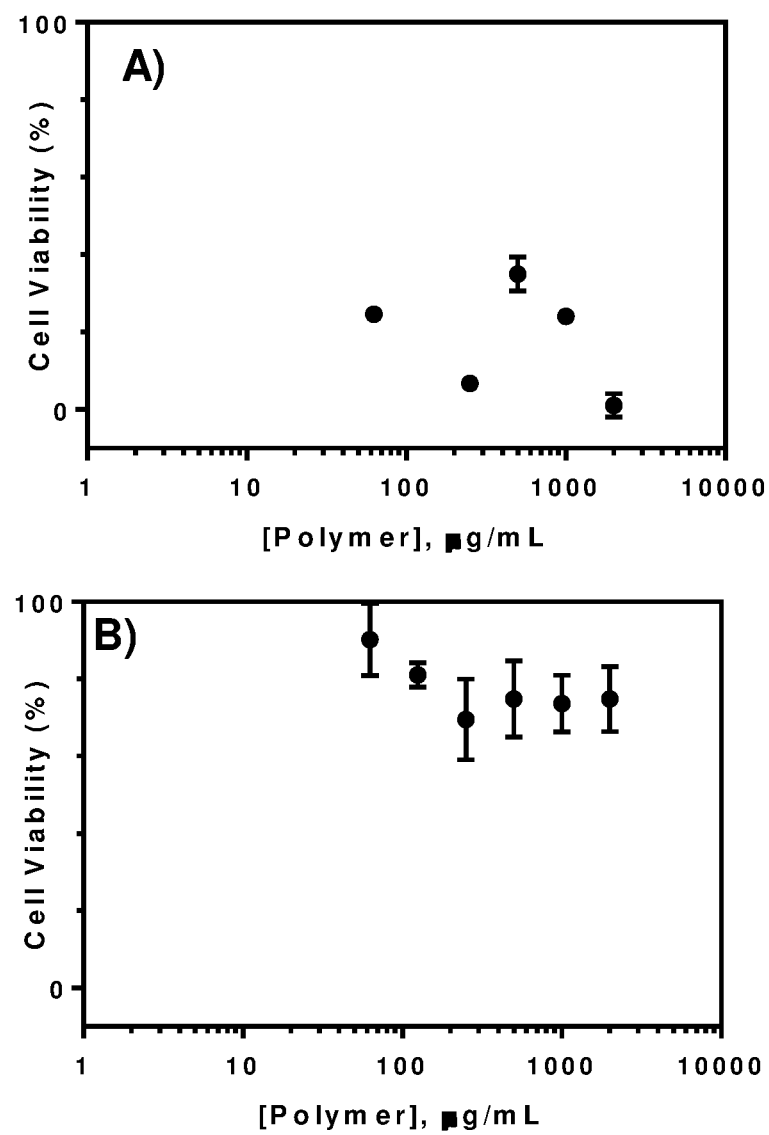
FIG. 2 shows comparison of the cytotoxicity of alpha-polylysine and epsilon-polylysine.
Figure 3:
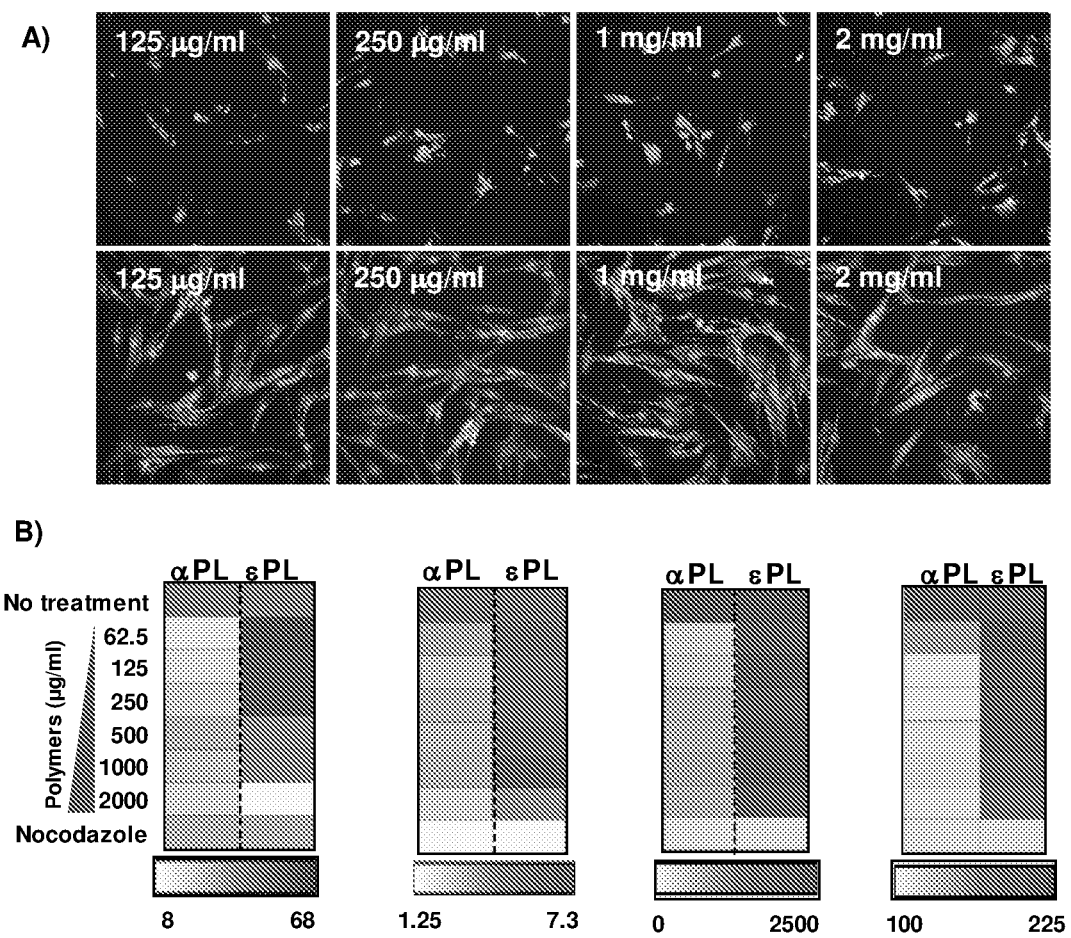
FIG. 3 shows comparison of the effect of alpha-polylysine and epsilon-polylysine on the primary human dermal fibroblasts (HDFs) cell health.

The cytotoxicity of cationic polymers for primary human dermal fibroblasts (HDFs) was assessed by MTT assay. FIGS. 2A and B compared the metabolic activity of HDFs treated with varying concentrations of αPL and εPL. At low concentrations, αPL inhibited the metabolic activity of HDFs whereas εPL did not alter the properties even at the highest concentrations (2 mg/mL) tested. Consistent with these results, HCA analysis indicated that HDFs exposed to αPL displayed considerable abnormalities in cellular morphology whereas cells exposed to εPL remained similar as untreated control (FIG. 3). Morphological analysis indicated that HDFs exposed to εPL did not show apparent change in 4 quantitative parameters: average cells/field, cell shape factor, cell area and nuclear area, which represented the status of cell health even at elevated polymer concentrations. Cells exposed to αPL, however, displayed profound changes in the cell morphology and lack of cytoskeletal components even at 125 µg/ml, thus suggesting cytotoxic effect of the polymers.

Example 3: Broad Spectrum Antimicrobial Properties of εPL

Figure 4:
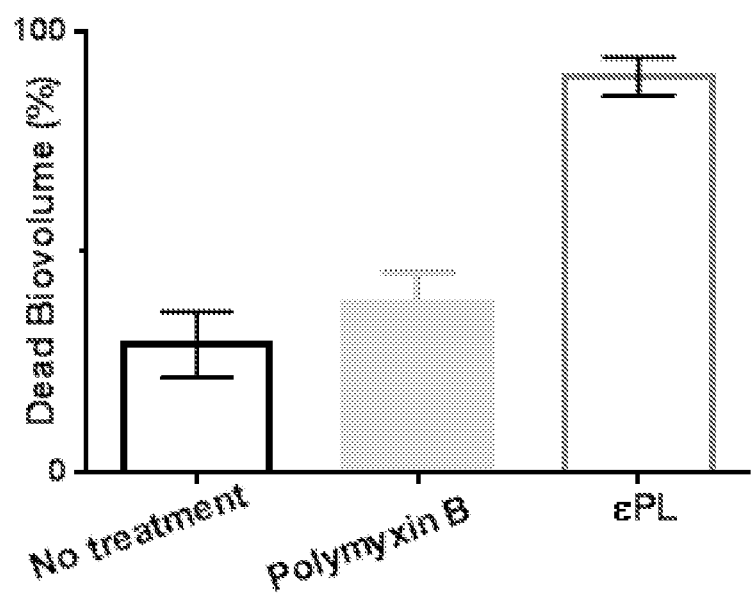
FIG. 4 shows the effect of the exposure of epsilon-polylysine to cells that are forming biofilm.
Figure 5:
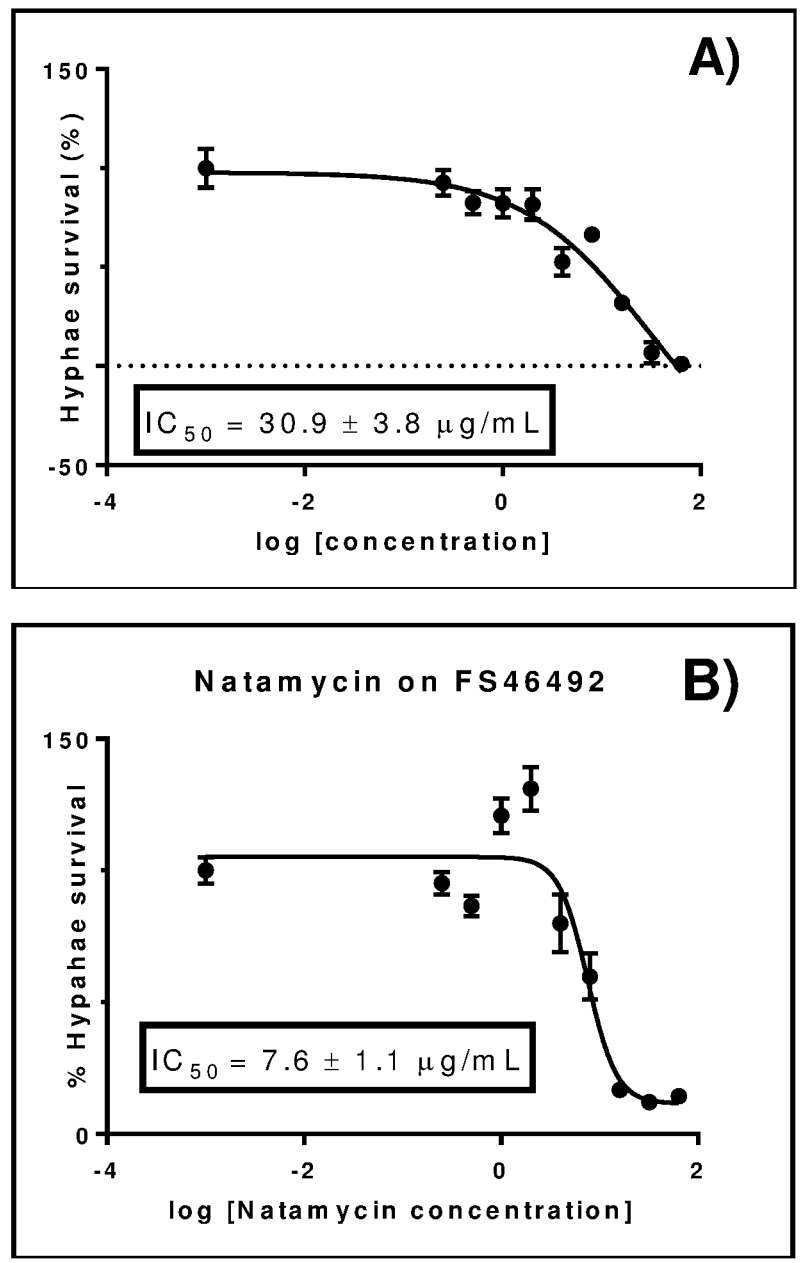
FIG. 5 shows the comparison of the effects of epsilon-polylysine and natamycin on fungal hyphal survival.

Encouraged by the lack of any cytotoxicity for the mammalian cells, the antimicrobial properties of εPL against a panel of antibiotic-resistant strains of Gram-positive and Gram-negative bacteria and filamentous fungi were examined. Table 2 listed the range of MIC values of εPL against a panel of pathogenic Gram-positive, Gram-negative and fungal strains. The values were compared with broad-spectrum ophthalmic antibacterial/antifungal drugs. The results indicated that the MIC of εPL did not shift significantly for various antibiotic-resistant strains whereas a number of strains displayed remarkable resistant to tobramycin. In a static biofilm model, εPL caused considerable decrease (>90%) in the biofilm burden of PA01 strains at 10×MIC (FIG. 4) and the activity was superior to cationic cyclic lipopeptide, polymyxin B. The polymer also decreased the viability of fungal hyphal cells with an $IC_{50}$ of 30.8±3.8 µg/ml (FIG. 5A) and the value was higher than FDA approved ophthalmic antifungal, natamycin (FIG. 5B).

TABLE 2

MIC of εPL against a panel of drug resistant bacteria and fungi.

| Microroganisms | MIC in mg/ml of | |
| --- | --- | --- |
| Bacteria | εPL | Tobramycin |
| *P. aeruginosa* (n = 22) | 8-32 | 0.5->100 |
| *K. pneumoniae* (n = 8) | 8-64 | 0.195-100 |
| *E. coli* (n = 8) | 8-32 | 0.195-100 |
| *E. clocae* complex (n = 4) | 16 | 1.56-100 |
| *A. baumanii* (n = 15) | 32-64 | 0.8-50 |
| Carbapenam-resistant *Enterobacter* strains (n = 20) | 16-32 | 0.8-50 |
| *S. aureus* (n = 9) | 4-16 | 0.5-1.0 |
| MRSA (n = 9) | 4-16 | 0.5->16 |
| VRE (n = 14) | 4-8 | — |
| Fungii | | Natamycin |
| *F. solani* and *F. oxysporum* (n = 6) | 0.5-8 | 8-16 |
| *C. tropicalis* (n = 10) | 1-128 | n.d. |
| *C. parapsilosis* (n = 10) | 4-64 | n.d. |

The number of strains used is indicated in parenthesis.

Example 4: Time-Kill Kinetics of εPL Against Gram-Positive and Gram-Negative Bacteria The dose-dependent kill kinetics of εPL for various Gram-negative species was shown in FIG. 6. The bactericidal activity of εPL was rapid against strains that showed enhanced resistance to aminoglycoside antibiotics. The CRE strains *E. coli* 19211 and *E. cloacae* 6780 displayed enhanced resistance to tobramycin at 100 µg/ml whereas rapidly killed upon exposure to εPL. A decrease in ≥3 $\log_{10}$ units in the viability could be achieved in 4 h at 2×MIC of the polymer. Similarly, a faster bactericidal effect was observed against *A. baumanii* 1001 strains that displayed enhanced resistance to gentamycin. When compared to Gram-negative strains, εPL displayed slower kinetics of bactericidal activity against all the *S. aureus* and MRSA strains. Overall, the microbiological studies established the potent antimicrobial properties of εPL against diverse disease causing and drug-resistant pathogens.

Figure 7:
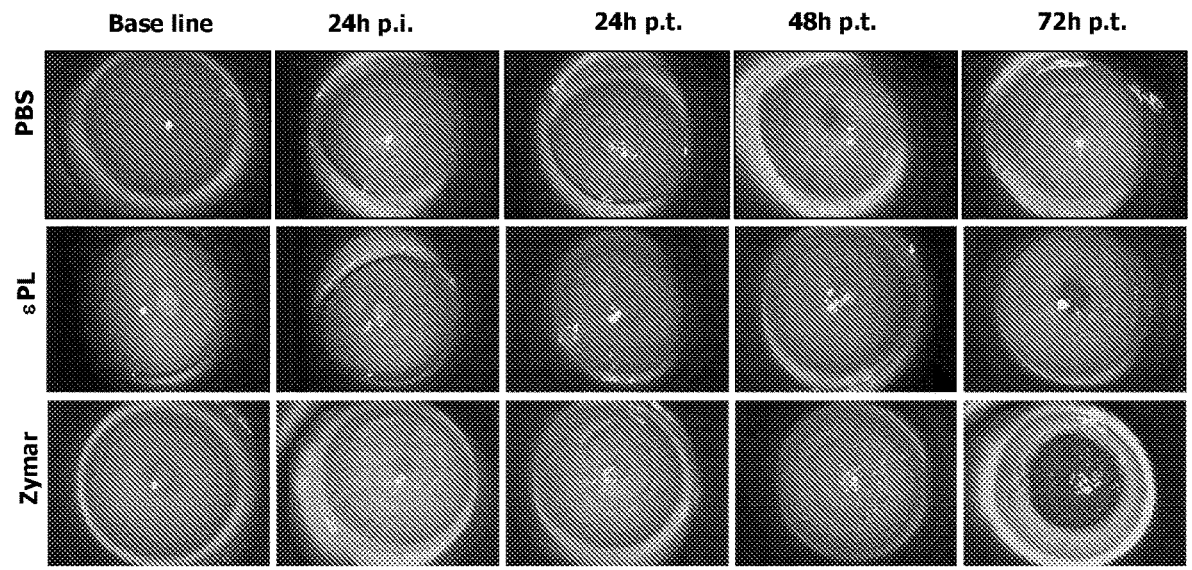
FIG. 7 shows a set of slit lamp biomicroscopy images comparing the efficacy of 0.3% (w/v) epsilon-polylysine in a rabbit model of infectious keratitis. An initial inoculum of $5 \times 10^6$ CFU/ml (50 µl) was applied to the wounded cornea and the image was taken at 24 hours post infection (p.i.). Treatment was started at this point by applying 50 µl of epsilon-polylysine or zymar (0.3% gatifloxacin) to the infected eye at 4 times/day for 3 days. Images were taken at 24, 48, 72 hours post treatment (p.t.). Vehicle alone (10 mM PBS) served as the control. Thus.
Figure 8:
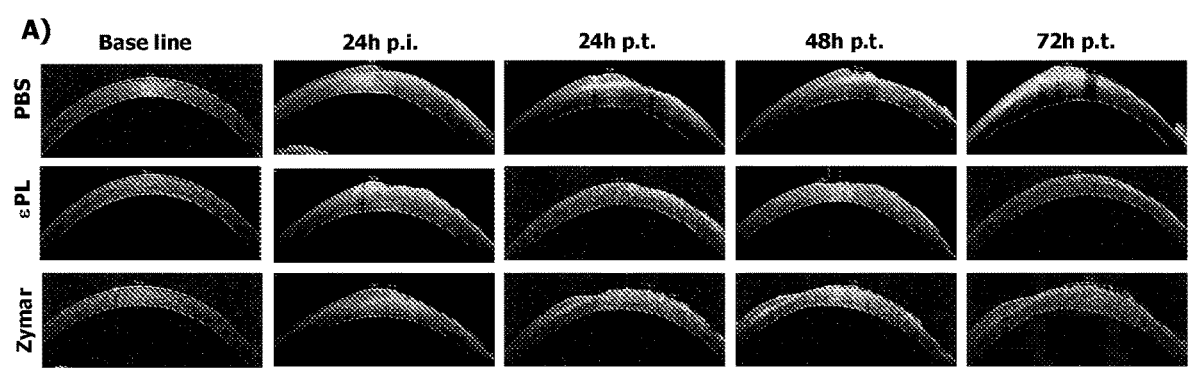
FIG. 8 shows comparison of epsilon-polylysine and zymar treatment on rabbit cornea.
Figure 8:
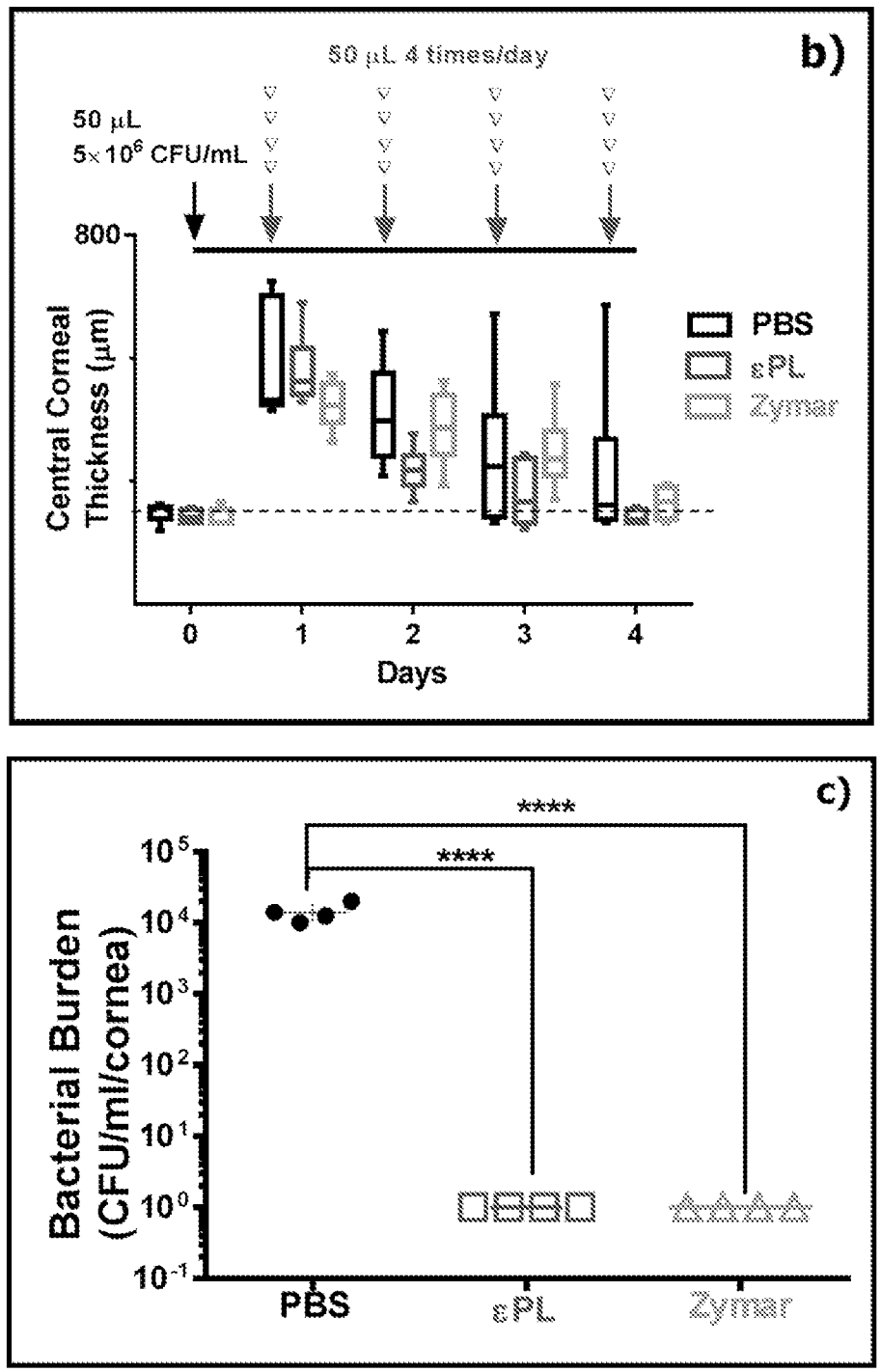

Example 5: Antimicrobial Potency of εPL in a Rabbit Model of Infectious Keratitis The in vivo efficacy of εPL (0.3% w/v) in PBS in a rabbit model of *S. aureus* keratitis was examined. The rabbits were anaesthetized prior and corneal infection was induced by applying 50 ml of *S. aureus* ATCC 29213 ($5 \times 10^6$ CFU/ml) strains. After 24 h post infection, 50 µL of the polymer or PBS were applied topically to the infected eyes at 4 times/day. For a comparison Zymar® eye drops was used as a positive control. Eyes were examined by slit lamp biomicroscopy and anterior segment optical coherence tomography which monitored the changes in corneal thickness after infection and treatment. SL examination of the eyes treated with εPL displayed significant decrease in chemosis and discharge, corneal haze and conjunctival redness in comparison to other groups (FIG. 7). An anterior segment OCT (AS-OCT) examination was carried out to infer the morphological changes in the cornea before and after infection/treatment. AS-OCT images demonstrated significant increase in corneal edema and irregular surface after infection and hyperreflective areas beneath the corneal epithelium at 24 h p.i. Treatment of infected eyes with topical 0.3% εPL resulted in significant decrease in the corneal thickness and the hyperreflective areas at 24 h p.t. After 48 h p.t., considerable decrease in corneal edema was observed and approached the baseline values at 48 h p.t. Complete recovery of baseline corneal thickness could be achieved at 72 h p.t. The AS-OCT images also indicated that εPL treated eyes displayed significant decrease in edema at 24 h p.t. in comparison to Zymar® or PBS treated eyes (FIGS. 8A and B). At the end of 3 days p.t., bacterial viability was enumerated. Both εPL and Zymar treated cornea did not show the presence of viable bacteria whereas PBS treated cornea contained $4.1 \pm 0.13$ $\log_{10}$ CFU/ml (FIG. 8C).

Next, the efficacy of εPL in a rabbit model of *P. aeruginosa* keratitis was examined. The infection and treatment protocols were maintained as before for the *S. aureus* keratitis model. After 24 h p.i., cornea infected with *P. aeruginosa* ATCC 9027 strains appeared hazy, edematous and significant presence of infiltrates. A considerable decrease in the chemosis and haze was observed after topical application of 0.3% εPL at 24 h p.t. A progressive decrease in the conjunctival redness, chemosis and haze was observed with increasing treatment regimen (FIG. 9A). AS-OCT images further demonstrated that the presurgical corneal thickness increased from $370 \pm 8$ µm to $570 \pm 49$ at 24 h p.i. After 1-3 day after treatment with εPL, a progressive decrease in the corneal thickness was observed (FIG. 9B). After 3 days p.t. with εPL, a substantial decrease in the hyperrefelective areas and corneal roughness was observed, confirming the potency of εPL in clearing *P. aeruginosa* infections. Microbiological enumeration of bacterial viability indicated no detection of viable bacteria in 5/6 corneas after εPL treatment whereas in one cornea a viability of $3.4 \pm 0.12$ $\log_{10}$ CFU was observed (FIG. 9C). However, PBS treated cornea contained $5.1 \pm 0.7$ $\log_{10}$ CFU, suggesting substantial decrease in the bacterial burden after εPL treatment. Together with in vitro microbiological studies, these results demonstrated excellent antimicrobial properties of εPL for topical applications.

Example 6: εPL Attenuates the Adverse Effect of *Pseudomonas aeruginosa* and *Staphylococcus aureus* on Human Dermal Fibroblasts (hDFs)

*P. aeruginosa* is responsible for increased mortality in patients with systemic and chronic wounds. The opportunistic pathogen enters nonphagocytic cells and the proteolytic activity of the enzymes produced by the bacteria plays a critical role in tissue penetration. To determine the morphological changes in hDF, the cells were exposed to green fluorescent protein-labeled PAO1 (PAO1_gfp) strains for 4 h. Considerable changes in host cell phenotype was evident at 4 h, as cell rounding and significant loss of actin filaments could be observed at 4 h post infection (p.i., FIGS. 15A and B). hDFs treated with εPL (1 mg/ml) prior to (prevention) or 2 h after infection (regression) prevented the adverse effect of the bacteria as well as its invasion efficiency as no intracellular bacteria could be observed (FIGS. 15C and D). A similar effect was observed against *S. aureus* infections as well, establishing potent antimicrobial properties of the polymer in averting adverse effects of pathogenic bacteria to mammalian cells.

Example 7: εPL Attenuates the LPS-Induced Inflammation

To determine if εPL binds to lipopolysaccharide (LPS), a key component of the outer membrane of the bacteria, THP1-Blue™ NF-κB reporter assay was performed. The results indicated substantial inhibition of LPS-induced inflammation of the monocytic cells at 1 mg/ml, confirming that the polymer binding to LPS attenuates adverse effect of the endotoxin (FIG. 16).

Figure 17:
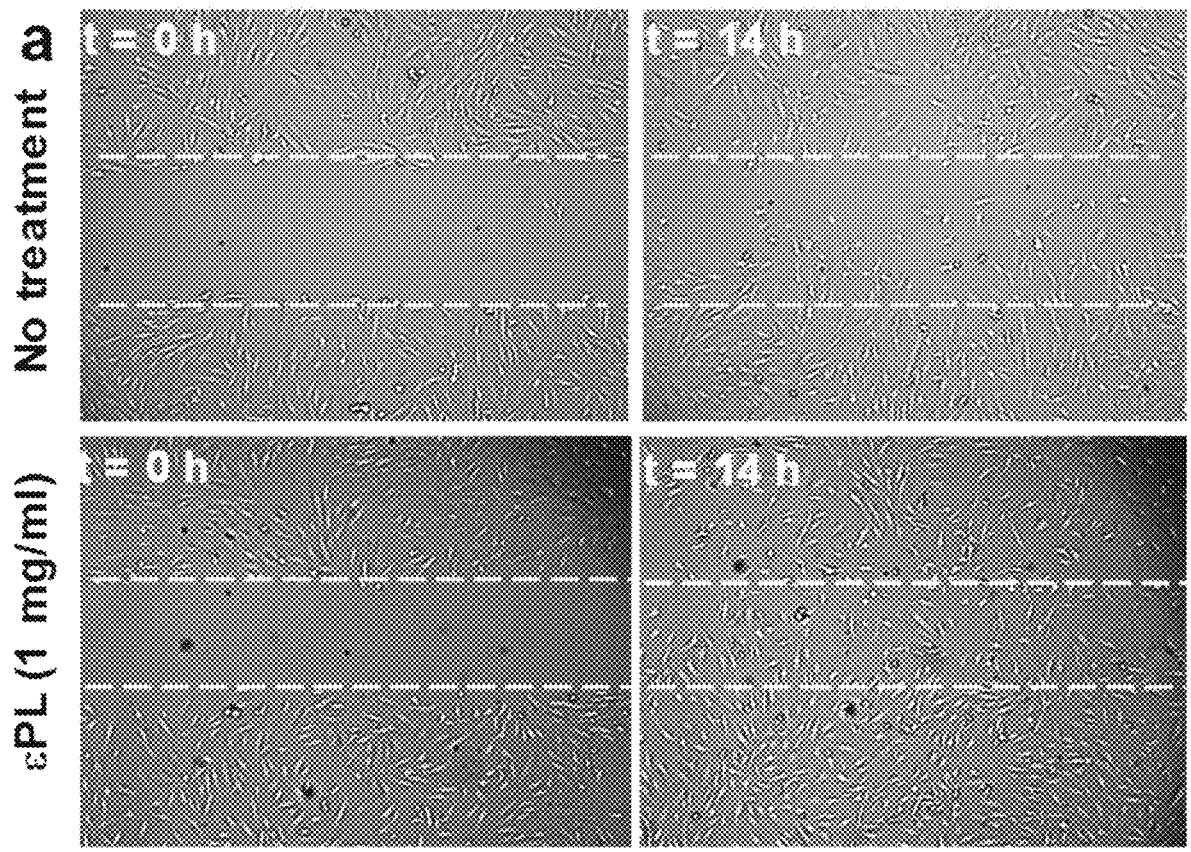
FIG. 17 shows effect of epsilon-polylysine on cell migration of human Dermal Fibroblasts (hDFs) under various conditions in a scratch wound assay model.
Figure 17:
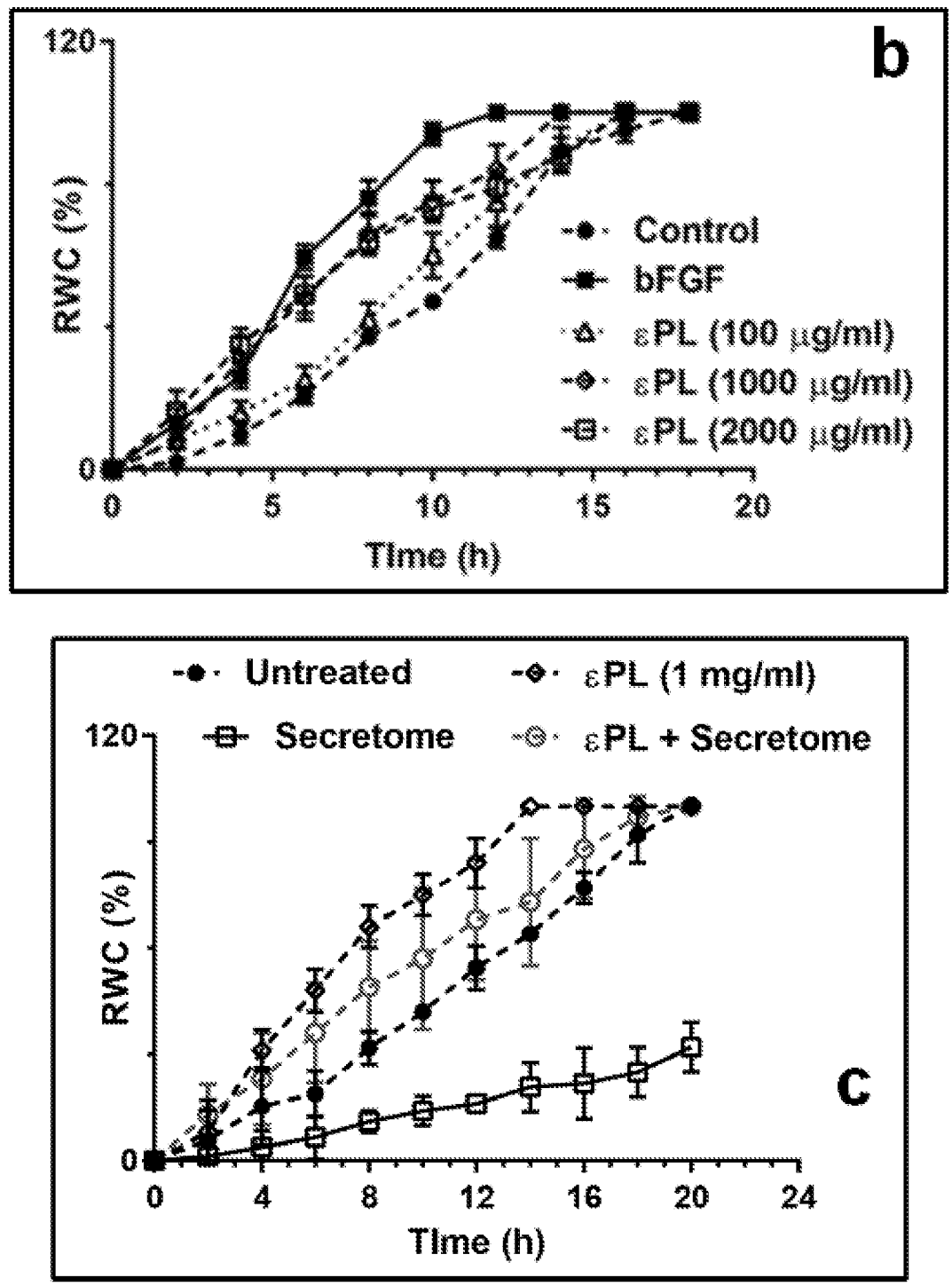

Example 8: εPL Promotes hDFs Cell Migration and Abrogates the Inhibitory Effect of Bacterial Secretomes It has been shown that opportunistic ocular pathogens *Serratia marcescenes*, *P. aeruginosa* and *S. aureus* derived factors (secretomes) inhibit the epithelial cell migration, thus contributing to the delayed corneal wound healing. Since εPL reduced the bacterial bioburden and corneal edema in a rabbit model of keratitis and was non-cytotoxic for hDFs even at elevated concentrations of the polymer, the fact whether the polymer interferes with fibroblasts migration was investigated. In vitro cell migration assay (scratch wound) of hDFs was used to assess if the polymer interfered with the cell migration. The results suggest that the polymer at 1 mg/ml increased the relative wound closure (RWC) and the initial rate was similar to that of recombinant fibroblasts growth factor (FIGS. 17A and B).

Next, it was assessed whether the bacterial secretomes which contain secreted and shredded molecules inhibit the hDF migration. Addition of 25-50% (v/v) of *S. aureus* secretome was non-cytotoxic for hDFs but inhibited the migration of hDFs (data not shown). However, in the presence of εPL (1 mg/ml), a spontaneous recovery was observed suggesting that the polymer abrogates the deleterious effect of bacterial secretomes (FIG. 17C). It has been reported that the commercially available wound cleanser and topical antiseptics prevent the fibroblasts migration and proliferation. Together, these observations demonstrate that εPL is biocompatible, promotes hDFs migration in vitro and averts the adverse effects of bacterial secreted products.

Example 9: Ocular Toxicity of εPL

The ocular toxicity of εPL at elevated concentrations (1.5%, w/v in PBS) was determined. The results indicated that the polymer, though a slight delay was observed after 3 days post injury in comparison to injured cornea treated with PBS or 0.3% εPL (w/v in PBS), the polymer did not impair the wound closure of the injured cornea (FIGS. 18A and B). These results establish the excellent biocompatibility of the polymer.

Figure 19:
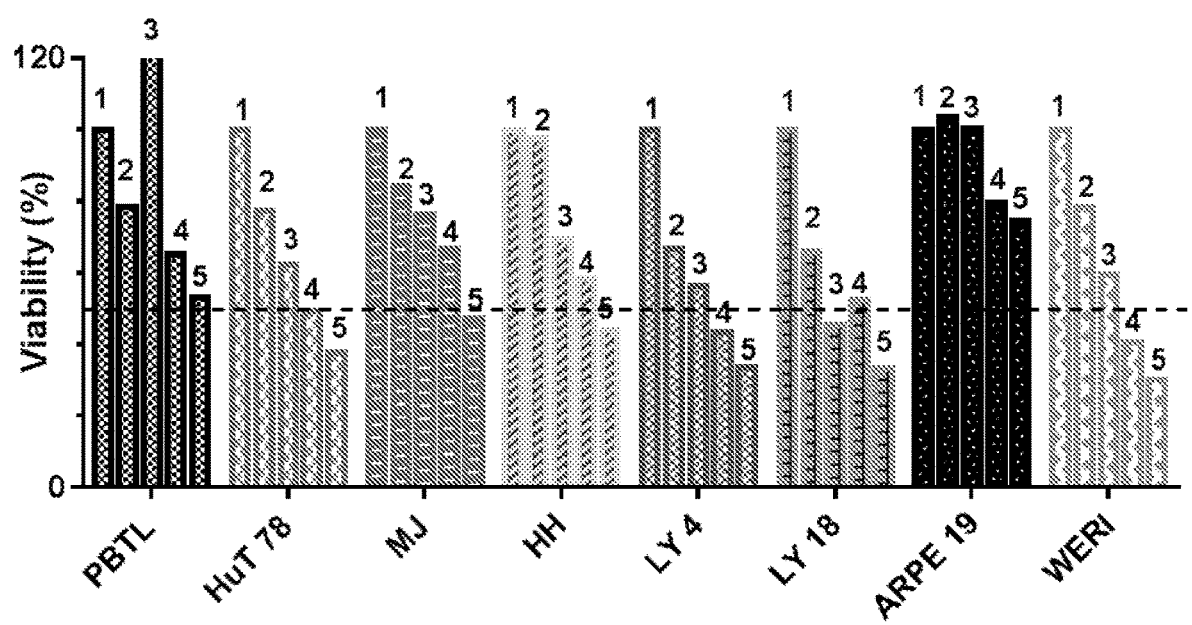
FIG. 19 shows a bar graph depicting anticancer properties of εPL against T-/B-cell lymphoma and retina blastoma cell lines. The numbers in figure indicates concentration of the polymer: 1—Untreated control (0 µg/ml); 2—62.5 µg/ml; 3—125 µg/ml; 4—125 µg/ml; 5—250 µg/ml. The horizontal dotted lines represent 50% cell viability. Thus.

Example 10: Anti-Cancer Properties of εPL

εPL displayed potent anticancer activity against T-cell lymphoma, B-cell lymphoma and retinoblastoma cell lines (FIG. 19). When compared to peripheral blood T-cells (PBTL) or retinal pigment epithelial cell lines (ARPE 19), a higher loss of viability was observed for the cancer cells exposed to various concentration of the polymer.

Example 11: Design of εPL Mimetic Peptides

Figure 10:
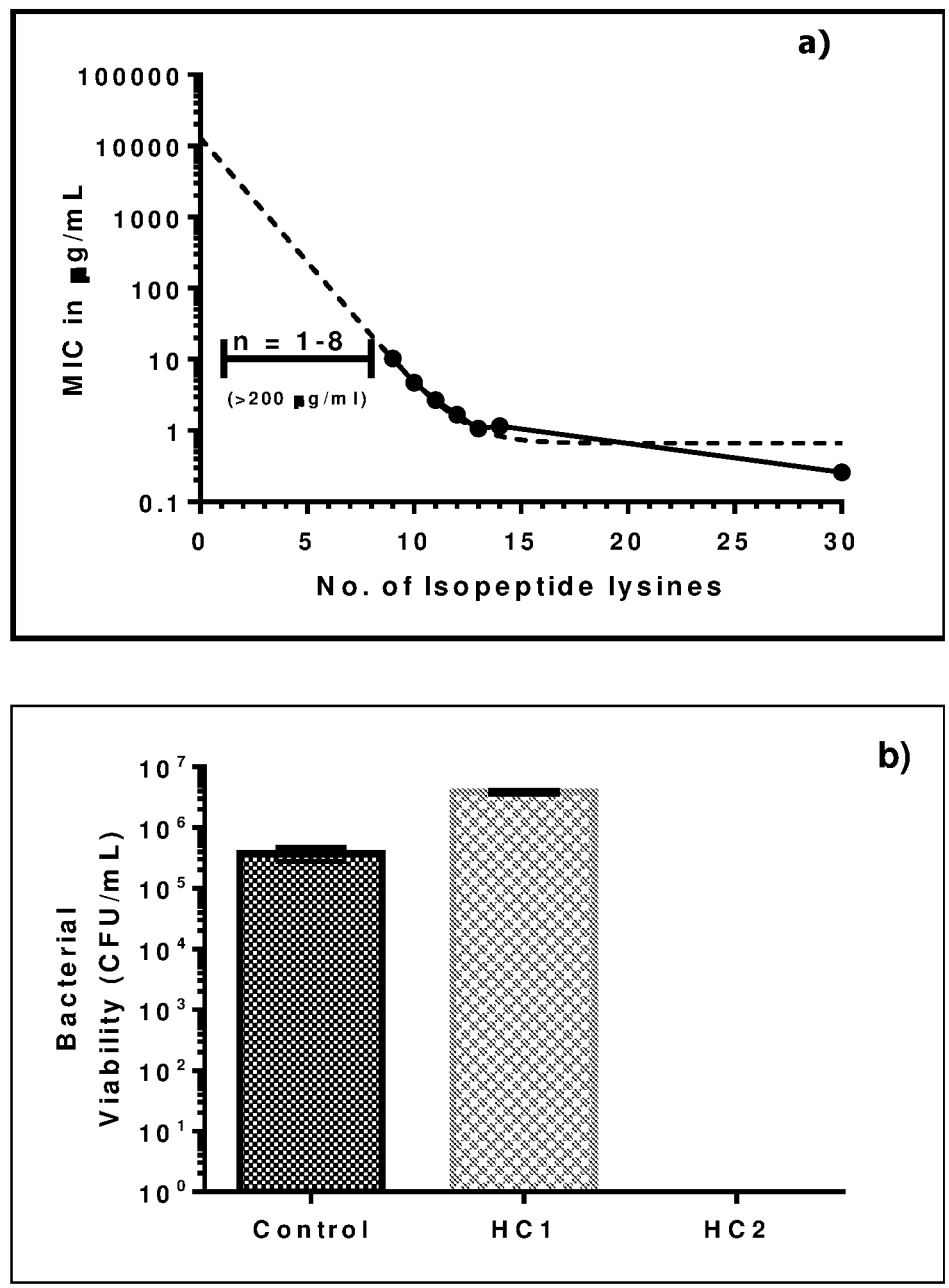
FIG. 10 shows the antimicrobial effect of epsilon-lysine residue in a peptide.

From the above results, the presence of ε-lysyl bond had superior selectivity for targeting prokaryotic cells than α-lysyl bonds was hypothesized. In addition, the presence of ε-lysyl bond may increase proteoltyic stability of the peptides as well. In a systematic study, Shima et al had shown that a minimum of 9 isopeptide linkage was necessary to impart minimal antimicrobial activity. As the number of repeats increased to ≥12, a plateau was observed. These results suggested that a minimum of 12 cationic residues were necessary to obtain a reasonably good antimicrobial activities based on MIC values (FIG. 10A). Based on this, 12 residue peptides which contained 6 lysine and arginine pairs in sequence were synthesized. The types of the amino acid residues used (either D- or L-amino acid) and the linkage between each amino acid residues (either α or ε linkage) were shown on FIG. 21. The peptides displayed broadspectrum antimicrobial against wide range of pathogens (Table 3). To check if the peptides retained the antimicrobial activity, their antimicrobial properties in the presence of trypsin were assessed. As shown in FIG. 10B, a complete loss of activity was observed for HC1 whereas HC2 retained the antimicrobial activity even after incubation with trypsin for 1 h.

TABLE 3

MIC of εPL mimetic peptides against panel of pathogens.

| | MIC in μg/ml of | | | |
|---|---|---|---|---|
| Strains | HC1 (SEQ ID NO: 3) | HC2 (SEQ ID NO: 17) | HC4 (SEQ ID NO: 18) | HC6 (SEQ ID NO: 19) |
| P. aeruginosa (n = 22) | 32-128 | 32-128 | 16-64 | 32-64 |
| K. pneumonia (n = 4) | 64 | 16-32 | 16-128 | 32-128 |
| E. coli (n = 3) | 16 | 8-16 | 16 | 16 |

TABLE 3-continued

MIC of εPL mimetic peptides against panel of pathogens.

| | MIC in μg/ml of | | | |
|---|---|---|---|---|
| Strains | HC1 (SEQ ID NO: 3) | HC2 (SEQ ID NO: 17) | HC4 (SEQ ID NO: 18) | HC6 (SEQ ID NO: 19) |
| E. clocae complex (n = 4) | 64-128 | 16-32 | 64-128 | 64-128 |
| A. baumanii (n = 3) | 64-128 | 32 | 16-32 | 16-64 |
| CRE strains (n = 4) | 64-128 | 64-128 | 64-128 | 64-128 |
| S. aureus (n = 6) | 32-64 | 32-128 | 32 | 32-64 |
| MRSA (n = 9) | 16-64 | 16-32 | 16-64 | 16-32 |
| VRE (n = 3) | 16-32 | 16 | 16 | 16 |
| C. albicans (n = 5) | 64-128 | 16-32 | 16-32 | 16-32 |

The number of strains used is indicated in parenthesis.
n.d. indicates not determined.

To confirm the overall objective that the presence of ε-lysyl peptide bond(s) will improve the selectivity, mellittin was chosen. Mellitin was a naturally occurring host defense peptide from bee venom (Apis mellifera) with well-known pore forming properties in both mammalian and microbial cells. The peptide displayed potent antimicrobial, antitumor and hemolytic activity, thus reducing its therapeutic potential. Mellittin contains 3 lysine residues (at $7^{th}$, $21^{st}$ and $23^{rd}$) connected by α-peptide bond. Each α-lysine residues individually and all the three residues simultaneously were replaced by ε-lysine residues and the antimicrobial activity and cytotoxicity of the designed peptides (Table 4) were examined. Replacing $Lys^{23}$ (Peptide 1) and $Lys^{21}$ (Peptide 2) did not alter the MIC values of the peptides against S. aureus, P. aeruginosa and C. albicans strains. As shown in Table 4, no apparent increase in the grand-mean MIC (GM-MIC) values was observed upon replacing $Lys^{21}$ and $Lys^{23}$. However, the conversion of $Lys^7$ to ε-lysine (Peptide 3) resulted in a significant increase in the GM-MIC values against S. aureus strains, a moderate increase in the values against P. aeruginosa and no significant increase or decrease against C. albicans. Replacement of all three residues (Peptide 4), however, completely abrogated the anti-S. aureus activity as indicated by 4-32 fold increase in the MIC values, 3 fold increase in GM-MIC against P. aeruginosa strains and did not alter the GM-MIC against C. albicans strains. These results highlighted that α-lysine residue at $7^{th}$ position was key to the antibacterial properties of melittin. Since Peptides 3 and 4 showed superior selectivity over microbial cells (see below), their antimicrobial activities against other Gram-positive strains and a panel of drug resistant pathogens such as carbapenam-resistant Enterobacter (CRE), vancomycin-resistant Enterococcus (VRE), polymyxin B-resistant E. cloacae complex were compared. As shown in Table 5, a moderate increase in the MIC values was observed for Peptides 3 and 4 against the drug-resistant strains in comparison to melittin.

TABLE 4

Amino acid sequence and therapeutic index values of melittin and modified peptides 1 to 4 against bacteria and yeast strains. ε-lysyl residue is indicated in italics and is underlined.

| | | MIC in µg/ml against | | | |
|---|---|---|---|---|---|
| Peptides | Amino acid sequence | P. aeruginosa (n = 5) | S. aureus or MRSA (n = 5) | C. albicans (n = 5) | Cytotoxicity (in µg/ml) for HDFs[1] |
| Melittin (SEQ ID NO: 2) | GIGAVLKVLTTGLPAL ISWIKRKRQQ | 4-16 (1.8)[2] | 4-8 (2.4) | 2-4 (3.7) | 16 |
| Peptide 1 (SEQ ID NO: 11) | GIGAVLKVLTTGLPAL ISWIKR*K*RQQ[3] | 4-16 (4) | 4-8 (5.4) | 4-8 (6.3) | 32 |
| Peptide 2 (SEQ ID NO: 12) | GIGAVLKVLTTGLPAL ISWI*K*RKRQQ | 4-16 (4) | 4-8 (4.6) | 4-8 (6.3) | 32 |
| Peptide 3 (SEQ ID NO: 13) | GIGAVL*K*VLTTGLPAL ISWIKRKRQQ | 16-32 (18.75) | 8-32 (14.0) | 4-8 (50) | 250 |
| Peptide 4 (SEQ ID NO: 14) | GIGAVL*K*VLTTGLPAL ISWI*K*RKRQQ | 16-64 (37.5) | 32-128 (15.6) | 4-8 (200) | 1000 |

[1] Concentration at which complete cytotoxicity was observed in MTS and HCA.
[2] Numbers in parenthesis indicates average therapeutic index (= +8 cytotoxicity+9 /MIC).
[3] ε-lysyl residue is denoted as "*K*"

Figure 11:
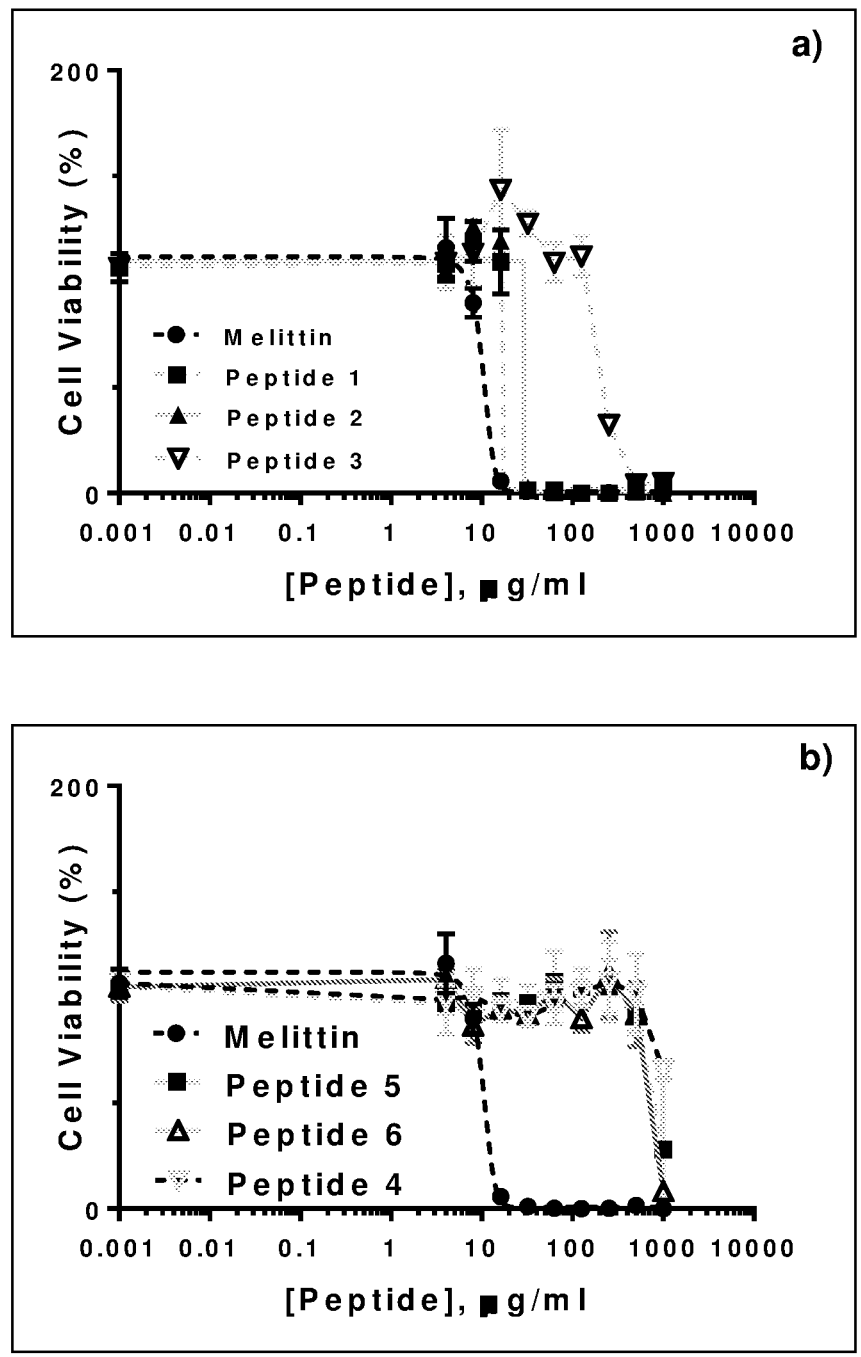
FIG. 11 shows the MTS cytotoxicity assay for a series of melittin peptide analogues carrying various number of ε-lysine residues for HDFs.

MTS assay confirmed that Peptides 1 and 2 displayed lower cytotoxic effect on HDFs than melittin. Interestingly, a profound decrease in the cytotoxicity of Peptide 3 was observed for HDFs suggesting that transformation the conversion of $Lys^7$ to ε-lysine enhanced the selectivity (FIG. 11). More pronounced decrease in the cytotoxicity was observed upon replacing all three α-lysines to ε-lysines. Interestingly, peptides 5 and 6 also showed lower cytotoxicity than melittin or peptide 3, suggesting greater cell selectivity of peptides 5 and 6. Analysis of the important cell health parameters from HCA further confirmed that Peptides 4-6 (FIG. 11) did not alter the cell morphology, cytoskeletal and nuclear components. Thus, it was concluded that ε-lysinylation of α-lysines in mellitin may amiolerate the selectivity of pore forming melittin, thereby enhancing the therapeutic potential.

The cell selectivity of two new peptides which carry two ε-lysyl residues was also assessed based on the above observations that replacing N-terminal lysine ($Lys^7$) improves the therapeutic index significantly over C-terminal α-lysine residues ($Lys^{21}$ and $Lys^{23}$). The antimicrobial and cytotoxicity of the newly designed peptides are shown in Table 5.

TABLE 5

MIC (or the antimicrobial properties) of melittin, peptides 3, 4, 5 and 6 were determined against a panel of drug-resistant bacteria and against other pathogenic yeast strains. The results indicated peptide 4 and 6 were potent amongst the other peptides.

| | MIC values in µg/ml | | | | |
|---|---|---|---|---|---|
| Strains | Melittin (SEQ ID NO: 2) | Peptide 3 (SEQ ID NO: 13) | Peptide 5 (SEQ ID NO: 15) | Peptide 6 (SEQ ID NO: 16) | Peptide 4 (SEQ ID NO: 14) |
| B. subtilis ATCC 6633 | 32 | 8 | 16 | 16 | 8 |
| B. cereus ATCC 11778 | 8 | 4 | 32 | 8 | 4 |
| S. epidermidis 12228 | 4 | 4 | 16 | 8 | 4 |
| VRE (n = 21 strains) | 0.5-8 ($MIC_{90}$ = 8)[2] | 4-8 ($MIC_{90}$ = 8) | 4-16 ($MIC_{90}$ = 8) | 4-16 ($MIC_{90}$ = 8) | 4-16 ($MIC_{90}$ = 8) |
| CRE (n = 19 strains) | 8-32 ($MIC_{50}$ = 8)[2] | 8-64 ($MIC_{50}$ = 8) | 4-64 ($MIC_{50}$ = 8) | 4-128 ($MIC_{50}$ = 16) | 8-64 ($MIC_{50}$ = 16) |

TABLE 5-continued

MIC (or the antimicrobial properties) of melittin, peptides 3, 4, 5 and 6 were determined against a panel of drug-resistant bacteria and against other pathogenic yeast strains. The results indicated peptide 4 and 6 were potent amongst the other peptides.

| Strains | MIC values in µg/ml | | | | |
|---|---|---|---|---|---|
| | Melittin (SEQ ID NO: 2) | Peptide 3 (SEQ ID NO: 13) | Peptide 5 (SEQ ID NO: 15) | Peptide 6 (SEQ ID NO: 16) | Peptide 4 (SEQ ID NO: 14) |
| *A. baumannii* (n = 10) | 2-4 (MIC$_{90}$ = 4)[2] | 2-4 (MIC$_{90}$ = 4) | 2-4 (MIC$_{90}$ = 4) | 4-8 (MIC$_{90}$ = 8) | 4-8 (MIC$_{90}$ = 8) |
| *E. cloacae* complex 44095 | 8 | 8 | 8 | 8 | 8 |
| *E. cloacae* complex 6780 | 8 | 4 | 8 | 16 | 4 |
| *C. albicans* (n = 5) | 2-4 | 4-8 | n.d. | 16-32 | 4-8 |
| *C. parpsilosis* (n = 9) | 16-64 | 16-64 | | 8-64 | 8-64 |
| *C. tropicalis* (n = 9) | 8-64 | 1-32 | | 2-32 | 1-32 |
| Cytotoxicity for primary human dermal fibroblasts | 16 | 250 | 1000 | 1000 | 1000 |

[1]Peptide 5 - two lysyl residues (Lys$^7$ and Lys$^{21}$) are replaced with ε-lysine - GIGAVL*K*VLTTGLPALISWIKRKRQQ (SEQ ID NO: 15); Peptide 6 - Lys$^7$ and Lys$^{23}$ GIGAVL*K*VLTTGLPALISWIKRKRQQ (SEQ ID NO: 16) are replaced with ε-lysine; all three lysine (Lys$^7$, Lys$^{21}$ and Lys$^{23}$) residues are replaced with ε-lysyl residues.
[2]MIC$_{90}$ and MIC$_{50}$ indicate the susceptibility of 90% of VRE or *A. baumannii* and 50% of CRE strains, respectively, at ≤ the indicated concentration.

TABLE 6

Comparison of various chemical modifications of melittin peptide to improve membrane selectivity.

| Peptide[b] | MIC[c] | Haemolytic activity | Reference |
|---|---|---|---|
| *Replacement with D-amino acids* | | | |
| Unmodified parent peptide: GIGAVLKVLTTGLPALISWIKRKRQQ | 0.2 - 3 µM at 4 × 10$^5$ CFU/mL | 100% at 4 µM | 4 |
| Modified peptide: GIGAVLKVLTTGLPALISWIKRKRQQ | 0.1 - 2 µM at 4 × 10$^5$ CFU/mL | 100% at 2 µM | |
| Unmodified parent peptide: GIGAVLKVLTTGLPALISWIKRKRQQ-NH2 | 0.3 - 20 µM at 5 × 10$^5$ CFU/mL | 100% at <10 µM | 5 |
| Modified peptide: GIGA*V*L*K*VLTTGLPAL*I*SW*IK*RKRQQ-NH2 | 0.8 - 12 µM at 5 × 10$^5$ CFU/mL | <25% at 50 µM | |
| *Introduction of peptoid residues* | | | |
| Unmodified parent peptide: GIGAVLKVLTTGLPALISWIKRKRQQ | 0.5 - 8 µM at 1 × 10$^6$ CFU/mL | >80% at 10 µM | 6 |
| Modified peptide: GIGAV*K*KVLTTG*K*PALISWKKRKRQQ | 2 - 8 µM at 1 × 10$^6$ CFU/mL | <10% at 100 µM | |
| *Cyclisation of linear peptides* | | | |
| Unmodified parent peptide: CGIGAVLKVLTTGLPALISWIKRKRQQC (linear) | 2 - 32 µM at 5 × 10$^5$ CFU/mL | Complete haemolytic activity at 10 µM | 7 |
| Modified peptide: CGIGAVLKVLTTGLPALISWIKRKRQQC (cyclised) | 0.8 - 10 µM at 5 × 10$^5$ CFU/mL | ~50% at 10 µM | |
| *Replacement with another amino acid residue* | | | |
| Unmodified parent peptide: GIGAVLKVLTTGLPALISWIKRKRQQ | 3.9 - 31.3 µM at 7.5 × 10$^5$ CFU/mL | 50% at 5 µM | 8 |
| Modified peptide: GIGAVLKVLTTGL*C*ALISWIKRKRQQ Succinylation of lysine molecules[d] | 62.5 - >125 µM at 7.5 × 10$^5$ CFU/mL | 50% at 2.5 µM | |

TABLE 6-continued

Comparison of various chemical modifications of melittin peptide to improve membrane selectivity.

| Peptide[b] | MIC[c] | Haemolytic activity | Reference |
|---|---|---|---|
| Modified peptide: GIGAVLKVLTTGLPALISWIKRKRQQ | Loss of peptide action | Loss of peptide action | 9 |

[a]Where available, the MIC and haemolysis data of the unmodified parent peptide is provided as basis of comparison.
[b]Associated modifications made to the mutant peptides are bolded and underlined.
[c]Range of minimum inhibitory concentrations (MIC) against a number of micro-organisms tested.
[d]Data corresponding to unmodified parent peptide is not available.

REFERENCES

4—D. Wade, A. Boman, B. Wåhlin, C. Drain, D. Andreu, H. G. Boman, R. B. Merrifield, *Proc. Natl. Acad. Sci. U S. A.* 1990, 87, 4761-4765.
5—Z. Oren, Y. Shai, *Biochemistry* 1997, 36, 1826-1835.
6—W. L. Zhu, Y. M. Song, Y. Park, K. H. Park, S.-T. Yang, J. I. Kim, I.-S. Park, K.-S. Hahm, S. Y. Shin, *Biochim. Biophys. Acta* 2007, 1768, 1506-1517.
7—T. Unger, Z. Oren, Y. Shai, *Biochemistry* 2001, 40, 6388-6397.
8—E. Jamasbi, S. Batinovic, R. A. Sharples, M.-A. Sani, R. M. Robins-Browne, J. D. Wade, F. Separovic, M. A. Hossain, *Amino acids* 2014, 46, 2759-2766.
9—R. Kini, H. J. EVANS, *Int. J. Pept. Protein Res.* 1989, 34, 277-286.

Example 12: Immunogenicity of Peptides 3 and 4

Figure 12:
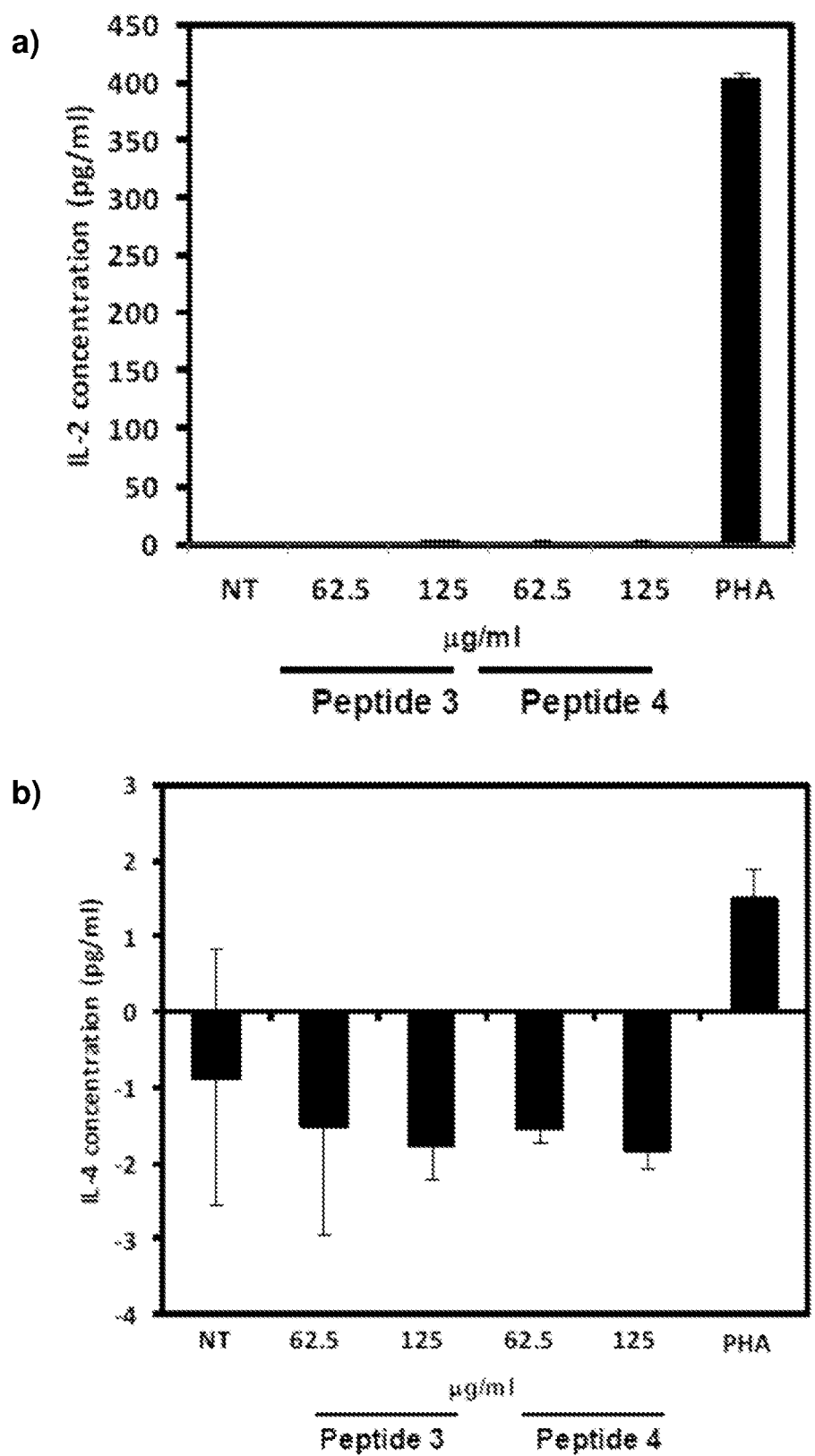
FIG. 12 shows a set of bar graphs representing the quantitative determination of cytokines from human primary blood T-cell lymphocytes (PBTL) exposed to peptides 3 and 4 after 24 h. The cytokines that are quantified are Interleukin-2 (IL-2; as shown on FIG. 12A), Interleukin-4 (IL-4; as shown on FIG. 12B), Interleukin-5 (IL-5; as shown on FIG. 12C), and Interferon-gamma (IFN-γ; as shown on FIG. 12D). Mitogenic plant lectin phytohaemagglutinin (PHA) was used as a positive control. Thus.
Figure 12:
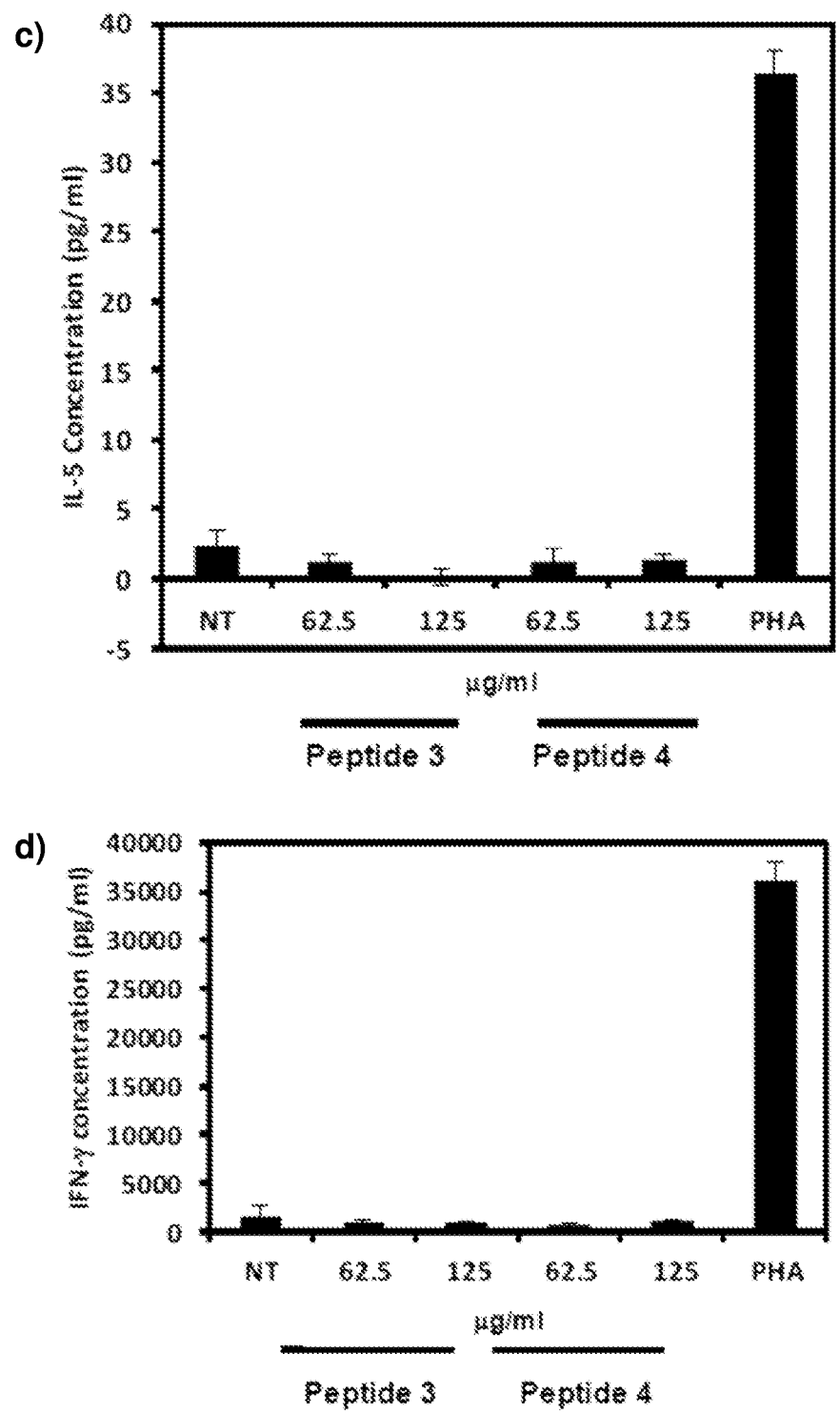

To understand if the peptides 3 and 4 did not cause adverse immunogenic reactions upon exposure to mammalian cells, their immunogenicity for human primary blood T-cell lymphocytes (PBTL) were determined. The cells were exposed to peptides (62.5 and 125 μg/ml) and the amounts of Interleukins-2, -4 and 5 (IL-2, IL-4 and IL-5) and Interferon γ (IFNγ) were quantitatively determined by Enzyme-linked immunosorbent assay (ELISA). Mitogenic plant lectin phytohaemagglutinin (PHA) was used as a positive controls. FIG. 12 A-D showed the quantitative determination of cytokines from PBTL after addition of peptides 3 and 4. The results indicated no apparent induction of cytokine production from PBTLs, thus confirming non-immunogenic nature of the peptides.

Example 13: ε-Lysylation Attenuated the Interaction with Mammalian Membrane

Figure 13:
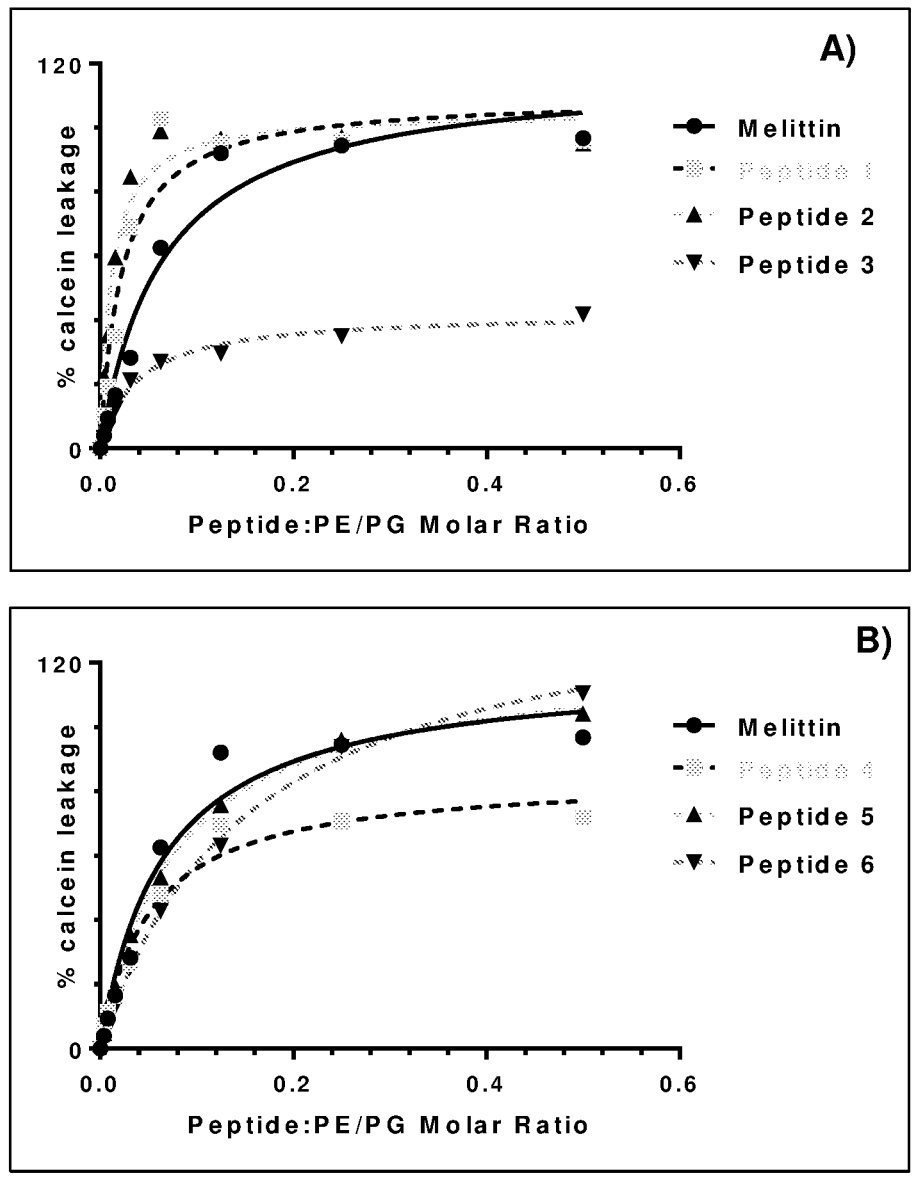
FIG. 13 shows a comparison of the fluorescent calcein dye leakage upon addition of peptides to microbial and mammalian model large unilamellar vesicles (LUVs).
Figure 13:
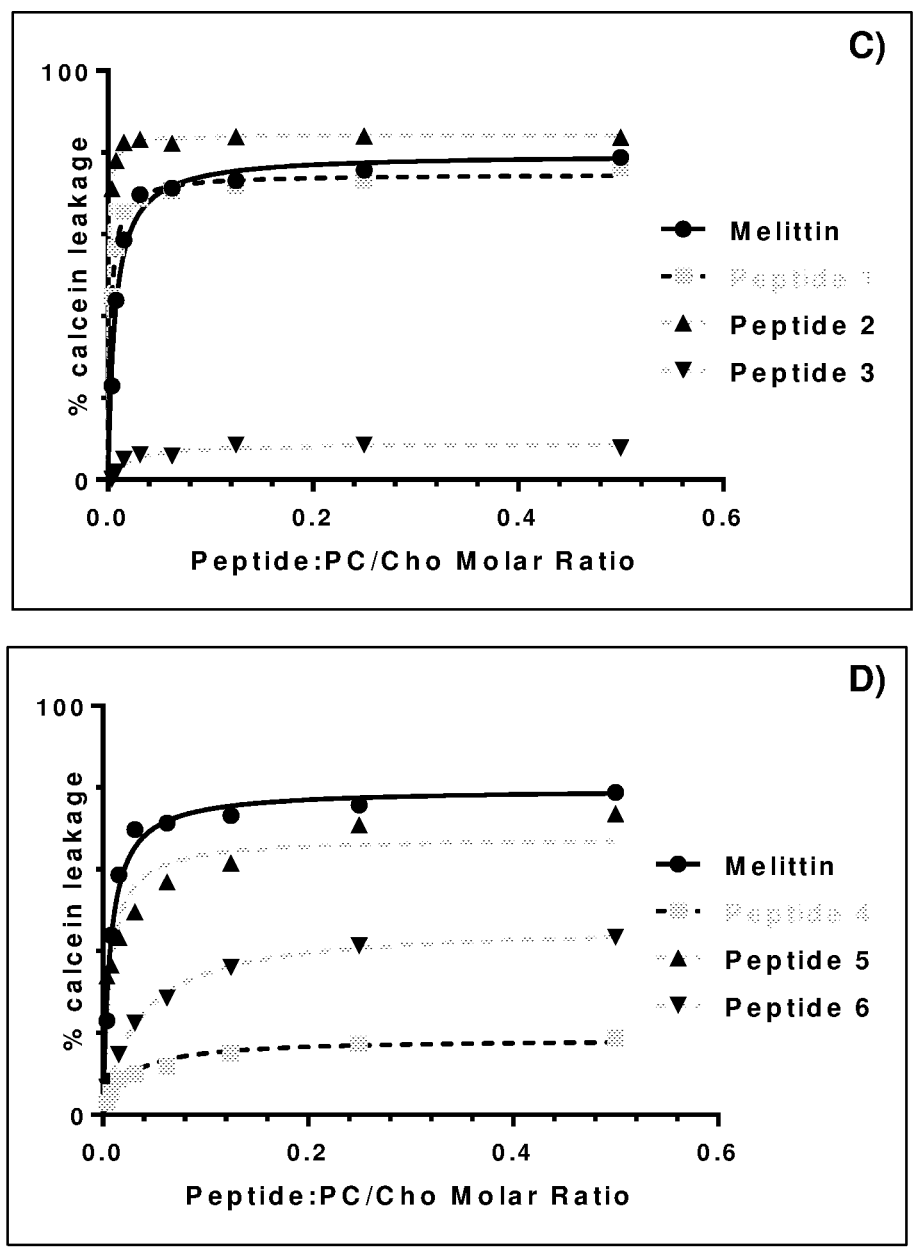

To obtain an insight into the mechanism of membrane discrimination, large unilamellar vesicles (LUVs) which mimic the cytoplasmic membrane of mammalian (PC/Cholesterol) and microbial (PE:PG) cells were used. Melittin, Peptide 1 and Peptide 2 displayed rapid and concentration-dependent release of the fluorescent probe (>90%) from negatively charged PE:PG LUVs whereas Peptide 3 displayed only a moderate increase in the dye leakage, achieving ~40% dye release (FIG. 13A). Peptides 4-6, however, displayed ~>70% dye release, with peptides 5 and 6 displaying similar membrane permeabilizing properties as melittin whereas a weaker was observed for Peptide 4 (FIG. 13B). More dramatic results were observed when the experiments were carried out on PC/Cholesterol LUVs. Melittin, Peptide 1 and Peptide 2 showed maximum dye release from the mammalian model LUVS, achieving ~70% dye leakage even at low (0.0625) peptide:lipid ratio (FIG. 13C). However, Peptide 3 did not show significant dye leakage (<20%) even at the highest (0.5) peptide:lipid ratio. These results clearly demonstrated that substitution of N-terminal α-lysine ($Lys^7$) by ε-lysine in melittin sequence increased the membrane selectivity. Among the peptides which carry multiple ε-lysine residues, peptide 4 displayed weaker interaction with mammalian model membrane than peptide 5 and 6.

Example 14: Multiple ε-Lysylation Modifies Poreforming Properties but Did not Affect the Bactericidal Properties To discern the pore-forming ability of modified peptide in comparison with melittin, the SYTOX green (SG) uptake assay was performed upon exposure of the peptides and their bactericidal properties were determined. SG is a membrane-impermeable dye which binds to genomic nucleic acids when cell membrane integrity is compromised and the DNA-SG complex displays significant increase in fluorescence intensity. Therefore the fluorescence intensity is taken to be proportional to the degree of cell membrane disruption caused by test peptides. FIG. 20A shows a representative SG uptake curves when melittin was added to VRE 1002 strains. Bacterial cells exposed to melittin at 1× and 2×MIC values, resulted in a burst and significant increase in SG uptake (79.2% at 1×MIC and 89.7% at 2×MIC). However, for Peptide 5 and Peptide 6 under the same conditions, a decreased SG uptake was observed (FIG. 20B). Similarly, against the *A. baumannii* strains melittin displayed higher SG uptake than Peptide 5 and Peptide 6 peptides at 2×MIC (FIG. 20C). These results confirm that ε-lysylation decreased the pore-forming properties of melittin. When comparing the SG uptake results with bacterial viability assay, however, indicated no apparent correlation, suggesting that the pore formation (i.e., SG uptake) and bactericidal properties are not coupled (FIG. 20D). These results highlight that though the modified peptides have poorer pore-forming properties than melittin, their bacterial lethality was similar to melittin.

Example 15: Antimicrobial Activity and Cytotoxicity of Mastoparans Peptides

Mastoparans were a family of pore-forming peptides from wasp venom which also form amphipathic helical structure in membrane-like environments. For this study Mastoparans B (MB, LKLKSIVSWAKKVL), which contained 4 lysine residues was investigated and 4 analogues (MB-1 to MB-4) wherein each α-lysine residue is replaced with ε-lysine residues were synthesized. The MIC against various VREs and CREs and cytotoxicity was determined. The results indicated position sensitive changes in the antimicrobial activities against both the drug-resistant strains. Against VREs, substitution of N-terminal α-lysines did not alter the $MIC_{50}$ values whereas replacing the C-terminal lysines resulted in 16-fold increase in the $MIC_{50}$ values (Table 7). Similarly, 8-16 fold increase in $MIC_{50}$ values was observed upon replacing the N-terminal α-lysine to ε-lysine against CRE strains (Table 7). Peptides MB3 and MB4 displayed clear MIC values against 14 and 11 strains only and the values increased to >256 for other CREs.

did not show any cytotoxic effect even at 1000 μg/m. Together with antimicrobial assays, these results demonstrated the ε-lysine substitution was position sensitive in mastoparan B peptides, as was observed for the Melittin peptides.

Example 16: Protocol for Assessing the Cytotoxicity by MTS Assay

Human dermal fibroblast cells were seeded in 96-well plates ($2\times10^3$ cells/well) and incubated for 24 h at 37° C. and 5% $CO_2$. Cells were then treated with various concentrations of polymers or peptides (62.5 μg/ml-1 mg/ml. At the end of the treatment period (after 24 h), 20 or 50 μl of MTS tetrazolium solution was added into 96-well or 12-well

TABLE 7

MIC of mastoparans peptides against Vancomycin-resistant enterococcus (VREs), Carbapenem-resistant enterobacteriaceae (CREs), A. baumannii and other drug resistant bacteria and fungi. The number of strains used is indicated in parenthesis. n.d. indicates not determined. MIC values are given in ranges. MIC50 indicates concentration at which 50% of the strains are susceptible. ε-lysyl residue is indicated in italics and is underlined.

| | MIC of Peptides in μg/ml | | | | |
|---|---|---|---|---|---|
| Strains | Mastoparan B (LKLKSIVS WAKKVL) (SEQ ID NO: 1) | MB-1 (L*K*LKSIV SWAKKV L) (SEQ ID NO: 7) | MB-2 (LKL*K*SIV SWAKKV L) (SEQ ID NO: 8) | MB-3 (LKLKSIV SWA*KK*V L) (SEQ ID NO: 9) | MB-4 (LKLKSI VSWAK*K* VL) (SEQ ID NO: 10) |
| B. subtilis ATCC 6633 | 64 | 8 | 4 | 32 | 94 |
| B. cereus ATCC 11778 | 8 | 32 | 128 | >256 | >256 |
| S. epidermidis 12228 | 4 | 4 | 8 | 64 | 64 |
| VRE (n = 21) | 1-8 ($MIC_{90}$ = 4)[1] | 1-8 ($MIC_{90}$ = 8) | 2-16 ($MIC_{90}$ = 8) | 4-128 ($MIC_{90}$ = 128) | 4-128 ($MIC_{90}$ = 128) |
| CRE (n = 19) | 2-32 ($MIC_{50}$ = 4) | 2-128 ($MIC_{50}$ = 32) | 4-256 ($MIC_{50}$ = 64) | 16->256 ($MIC_{50}$ = 64) | 32->256 ($MIC_{50}$ = 64) |
| A. baumanii (n = 10) | 1-2 ($MIC_{90}$ = 2) | 2-8 ($MIC_{90}$ = 8) | 4-8 ($MIC_{90}$ = 8) | n.d. | n.d. |
| E. cloacae complex 44095 | 2 | 4 | 8 | 64 | 64 |
| E. cloacae complex 6780 | 2 | 4 | 8 | 64 | 64 |
| C. albicans (n = 5) | 1-4 | 1-4 | 1-4 | n.d. | n.d. |
| C. parpsilosis (n = 9) | 1-8 | 2-16 | 4-32 | | |
| C. tropicalis (n = 9) | 0.5-2.0 | 0.5-4.0 | 0.5-4.0 | | |
| Cytotoxicity for HDFs μg/ml) | 125 | 250 | 1000 | 1000 | >1000 |

[1]$MIC_{90}$ and $MIC_{50}$ indicate the susceptibility of 90% of VRE or A. baumannii and 50% of CRE strains, respectively, at ≤ the indicated concentration. n.d. indicates not determined.

Figure 14:
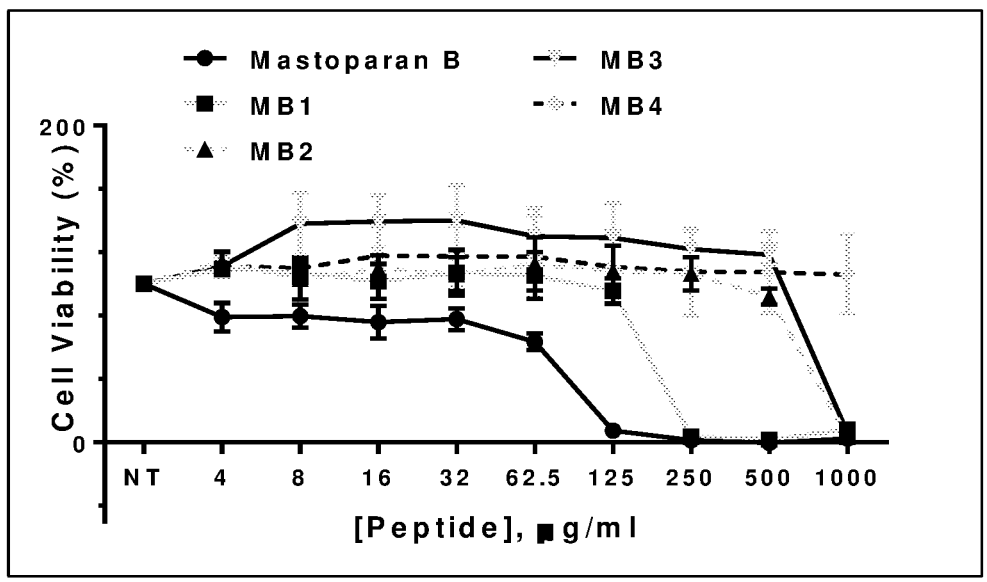
FIG. 14 shows a line graph representing the cytotoxicity of mastoparan B analogues MB-1 to MB-4 toward primary human dermal fibroblasts (HDF) cells assessed by MTT assay. Thus.

MTS assays indicated that mastoparan B was cytotoxic to primary human fibroblasts cells as the concentration exceeded 62.5 μg/ml (FIG. 14). Peptide concentration of 250 and 1000 μg/ml, respectively were required for MB1 and MB2/MB3 in order to impart cytotoxic effect. Peptide MB4 plates and further incubated for 2 h at 37° C. Subsequently, the absorbance was measured at 490 nm using a microplate reader (Infinite M200 Pro, Tecan, Switzerland) and the relative cell viability was calculated. Each treatment was performed in two triplicates and reported.

Example 17: Assessment of Cytotoxicity of Cationic Peptides and Polymers

The cytotoxicity of peptides and polymers were determined using CellTier 96® Aqueous One solution cell proliferation assay kit according to the manufacturer's instruction (Promega Corporation, Madison, Wis.). This assay evaluates mitochondrial function by measuring ability of viable cells to reduce MTS ((3-(4,5-dimethylthiazol-2-yl)-5-(3-carboxymethoxyphenyl)-2-(4-sulfophenyl)-2H-tetrazolium)) into a quantifiable blue, insoluble formazan product. HDFs were seeded in 96-well plates ($2 \times 10^3$ cells/well) and incubated for 24 h at 37° C. and 5% $CO_2$. Cells were then treated with a concentrated stock solution of polymers (final concentration 62.5-2000 μg/ml in the well) or peptides (final concentration 4-1000 μg/ml in the well). After 24 h, 20 μl of MTS tetrazolium solution was added into 96-well well plates and further incubated for 2 h at 37° C. Subsequently, the absorbance was measured at 490 nm using a microplate reader (Infinite M200 Pro, Tecan, Switzerland) and the relative cell viability was calculated relative to untreated control (10 mM PBS, pH 7.0). Each treatment was performed in two triplicates and reported. For the calculation of therapeutic index, the peptide or polymer concentration at which a complete loss of viability of HDFs was observed and was divided by the MIC values.

Example 18: Antimicrobial Susceptibility Testing

MICs of polymers/antibiotics were determined using the microdilution method in 96 well microtitre plates (SPL Life Sciences Co., Ltd, Korea), following the guidelines of Clinical and Laboratory Standards Institute (CLSI) document M100-S18. Briefly, polymers (1-512 μg/ml) or antibiotics were dissolved in appropriate media (Mueller Hinton broth, MHB for bacteria; Sabaroud's Dextrose (SD) broth for yeasts and RPMI buffer for *Fusarium* strains) and 100 μl of this was then mixed with an equal volume of microbial inoculum ($OD_{600}$=~0.08) in the same media and shaken in a closed incubator. After 24 h (for bacteria) or 48 h (for fungus) MIC was determined as the concentration where a complete inhibition (by visual observations as well as $OD_{600}$ readings) was observed. For peptides, 2× concentration of the peptides (2-256 μg/ml) in MilliQ water was mixed with the microbial inoculum and the MIC was determined as before.

Example 19: Therapeutic Index

The experimental data derived from MTS and antimicrobial assays were used to determine TI values, which is defined as the ratio of the lowest concentration at which complete cytotoxicity was observed over minimum inhibitory concentration. The average values of each strains for which the TI were calculated were reported in Table 4.

Example 20: Antimicrobial Activity of the Peptides in Trypsin

To determine the antimicrobial activity of the peptides in the presence of proteases, 1 mg/ml of HC1 and HC2 were incubated with trypsin enzyme:peptide weight ratio 1:100) for 1 h at 37° C. After this, a 20 μl aliquot of this solution was mixed 180 μl of bacterial inoculum (*P. aeruginosa* ATCC 9027, $10^5$ CFU/ml in MHB) and incubated at room temperature for 6 h. 100 μL aliquots of the suspension was diluted serially (10-fold) in 10 mM PBS solution and pour plated on MH agar plates and incubated at 37° C. for 48 h and colony forming units per ml (CFU/ml) are enumerated.

Example 21: Anticancer Properties of Hypercharged Peptides

Figure 22:
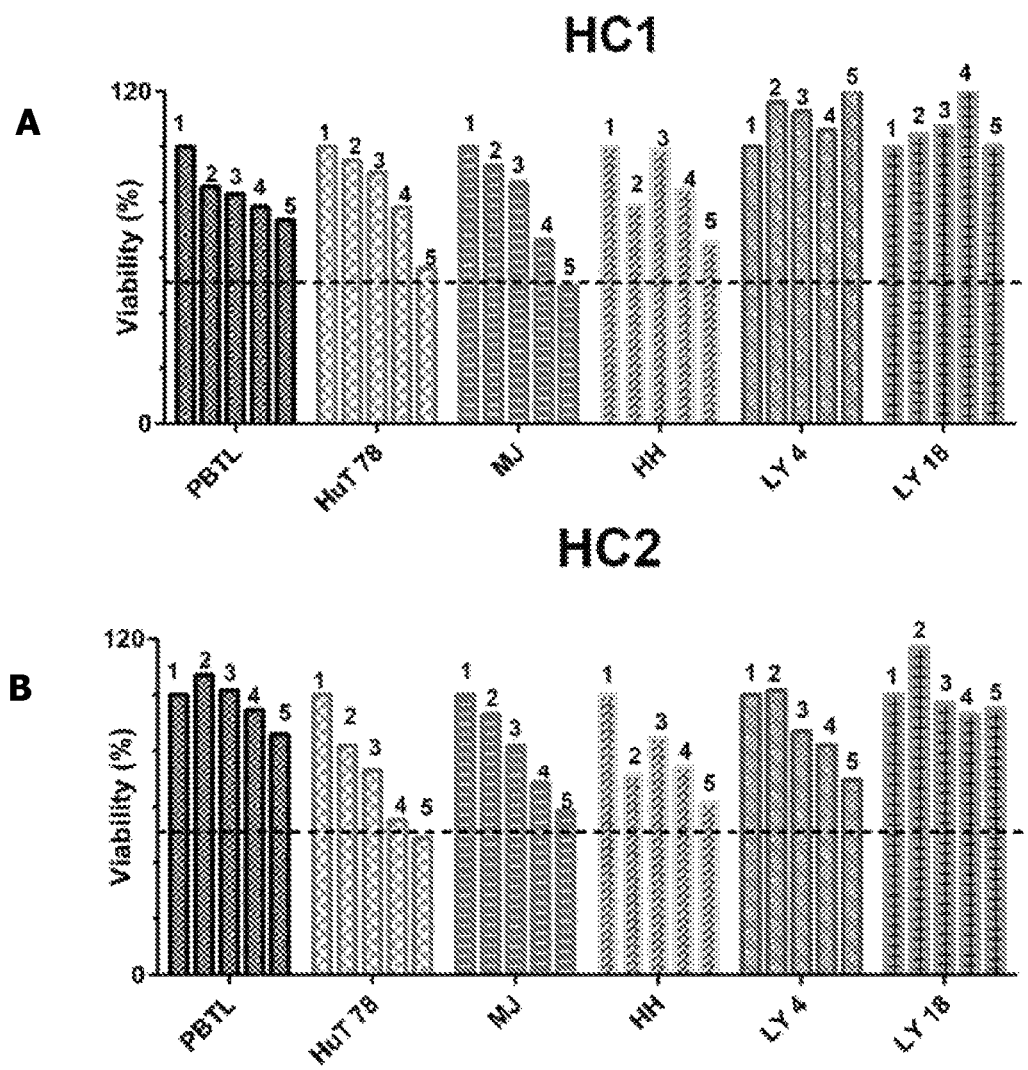
FIG. 22 shows a set of bar graphs depicting anticancer properties of hyper charged peptides HC1 (FIG. 22A), HC2 (FIG. 22B), HC4 (FIG. 22C), and HC6 (FIG. 22D) against T-/B-cell lymphoma cell lines. The numbers in figure indicates concentration of the polymer: 1—Untreated control (0 µg/ml); 2—62.5 µg/ml; 3—125 µg/ml; 4—250 µg/ml; 5—500 µg/ml. The horizontal dotted lines represent 50% cell viability. Thus.

The hyper-charged peptides were screened for their anticancer properties using cell lines derived from patients with various forms of cutaneous lymphomas, including T-cell lymphomas (HuT78, MJ, HH) and B-cell lymphomas (Ly-4 and Ly-18). The relative cytotoxicity of these peptides was also assessed in healthy primary peripheral blood lymphocyte (PBL) T-cells. Cytotoxicity was measured as the mitochondrial function by metabolic reduction of MTS. For this purpose, cells were treated with 4 different concentrations (62.5, 125, 250 or 500 μg/ml) of the peptides; untreated cells were used as a control. Cell viability data showed that all the modified peptides as well as εPL displayed varying degrees of cell killing in lymphoma cell lines in a dose dependent manner (FIG. 22). Interestingly, PBL T-cells were less sensitive to these peptides compared to the lymphoma cell lines.

The invention claimed is:

1. An isolated peptide comprising the amino acid sequence of LKLKSIVSWAKKVL (SEQ ID NO: 1), wherein at least one of the lysine residues (K) is an epsilon-lysine residue.

2. The peptide of claim 1, wherein when the peptide comprises one epsilon-lysine residue, the epsilon-lysine residue is located at
   position 2 (SEQ ID NO: 7), or
   position 4 (SEQ ID NO: 8), or
   position 11 (SEQ ID NO: 9), or
   position 12 (SEQ ID NO: 10).

3. A pharmaceutical composition comprising one or more peptide(s) as claimed in claim 1.

4. An ophthalmic preparation comprising one or more peptide(s) as claimed in claim 1.

5. An isolated peptide comprising the amino acid sequence of GIGAVLKVLTTGLPALISWIKRKRQQ (SEQ ID NO: 2), wherein at least one of the lysine residues is an epsilon-lysine residue.

6. The peptide of claim 5, wherein when the peptide comprises
   (i) one epsilon-lysine residue, the epsilon-lysine residue is located
      at position 7 (SEQ ID NO: 13), or
      at position 21 (SEQ ID NO: 12), or
      at position 23 (SEQ ID NO: 11);
      or
   (ii) two epsilon-lysine residues, the epsilon-lysine residues are located
      at position 7 and position 21 (SEQ ID NO: 15), or
      at position 7 and position 23 (SEQ ID NO: 16);
      or
   (iii) three epsilon-lysine residues, the three epsilon-lysine residues are located at position 7, position 21, and position 23 (SEQ ID NO: 14).

7. A pharmaceutical composition comprising one or more peptide(s) as claimed in claim 5.

8. An ophthalmic preparation comprising one or more peptide(s) as claimed in claim 5.

9. An isolated peptide comprising the amino acid sequence of KRKRKRKRKRKR (SEQ ID NO: 3), wherein at least one of the lysine residues is an epsilon-lysine residue.

10. The peptide of claim 9, wherein when the peptide comprises six epsilon-lysine residues, the six epsilon-lysine residues are located at position 1, position 3, position 5, position 7, position 9, and position 11 (SEQ ID NO: 17, or SEQ ID NO: 18, or SEQ ID NO: 19).

11. A pharmaceutical composition comprising one or more peptide(s) as claimed in claim 9.

12. An ophthalmic preparation comprising one or more peptide(s) as claimed in claim 9.

* * * * *

UNITED STATES PATENT AND TRADEMARK OFFICE
CERTIFICATE OF CORRECTION

PATENT NO. : 11,396,531 B2
APPLICATION NO. : 16/346808
DATED : July 26, 2022
INVENTOR(S) : Rajamani et al.

It is certified that error appears in the above-identified patent and that said Letters Patent is hereby corrected as shown below:

In the Specification

Columns 45 and 46, Table 6: Please delete Table 6 and replace with the following:

| Peptide[b] | MIC [c] | Haemolytic activity | Reference |
|---|---|---|---|
| *Replacement with D-amino acids* | | | |
| Unmodified parent peptide: GIGAVLKVLTTGLPALISWIKRKRQQ (SEQ ID NO: 2) | 0.2 – 3 µM at 1 – 4 × $10^5$ CFU/mL | 100% at 4 µM | 4 |
| Modified peptide: GIGAVLKVLTTGLPALISWIKRKRQQ (SEQ ID NO: 20) | 0.1 – 2 µM at 1 – 4 × $10^5$ CFU/mL | 100% at 2 µM | |
| Unmodified parent peptide: GIGAVLKVLTTGLPALISWIKRKRQQ-NH₂ (SEQ ID NO: 2) | 0.3 – 20 µM at 5 × $10^5$ CFU/mL | 100% at <10 µM | 5 |
| Modified peptide: GIGAVLKVLTTGLPALISWIKRKRQQ-NH2 (SEQ ID NO: 21) | 0.8 – 12 µM at 5 × 105 CFU/mL | <25% at 50 µM | |
| *Introduction of peptoid residues* | | | |
| Unmodified parent peptide: GIGAVLKVLTTGLPALISWIKRKRQQ (SEQ ID NO: 2) | 0.5 – 8 µM at 1 × $10^6$ CFU/mL | >80% at 10 µM | 6 |

Signed and Sealed this
Twentieth Day of December, 2022

Katherine Kelly Vidal
*Director of the United States Patent and Trademark Office*

| Modified peptide: GIGAVKKVLTTGKPALISWKKRKRQQ (SEQ ID NO: 22) | 2 – 8 μM at 1 × 10⁶ CFU/mL | <10% at 100 μM | |
|---|---|---|---|
| *Cyclisation of linear peptides* | | | |
| Unmodified parent peptide: CGIGAVLKVLTTGLPALISWIKRKRQQC (linear; SEQ ID NO: 23) | 2 – 32 μM at 5 × 10⁵ CFU/mL | Complete haemolytic activity at 10 μM | 7 |
| Modified peptide: CGIGAVLKVLTTGLPALISWIKRKRQQC (cyclised; SEQ ID NO: 23) | 0.8 – 10 μM at 5 × 10⁵ CFU/mL | ~50% at 10 μM | |
| *Replacement with another amino acid residue* | | | |
| Unmodified parent peptide: | 3.9 – 31.3 μM at 7.5 × 10⁵ CFU/mL | 50% at 5 μM | 8 |

Columns 49 and 50, Table 7, heading: Please correct "MIC50" to read --$MIC_{50}$--